(12) United States Patent
Jenkins et al.

(10) Patent No.: US 8,825,133 B2
(45) Date of Patent: *Sep. 2, 2014

(54) MRI-GUIDED CATHETERS

(71) Applicant: MRI Interventions, Inc., Memphis, TN (US)

(72) Inventors: Kimble L. Jenkins, Memphis, TN (US); Peter Piferi, Orange, CA (US); Kamal Vij, Chandler, AZ (US); Daniele Ghidoli, Laguna Hills, CA (US); Jesse Flores, Perris, CA (US); Parag V. Karmarkar, Columbia, MD (US); Rajesh Pandey, Raleigh, NC (US)

(73) Assignee: MRI Interventions, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/749,351

(22) Filed: Jan. 24, 2013

(65) Prior Publication Data

US 2013/0131496 A1 May 23, 2013

Related U.S. Application Data

(63) Continuation-in-part of application No. 12/816,803, filed on Jun. 16, 2010, now Pat. No. 8,369,930, and a continuation-in-part of application No. PCT/US2012/026468, filed on Feb. 24, 2012.

(60) Provisional application No. 61/187,323, filed on Jun. 16, 2009, provisional application No. 61/219,638, filed on Jun. 23, 2009, provisional application No. 61/261,103, filed on Nov. 13, 2009, provisional application No. 61/446,329, filed on Feb. 24, 2011.

(51) Int. Cl.

| | | |
|---|---|---|
| *A61B 5/05* | (2006.01) | |
| *A61B 5/00* | (2006.01) | |
| *A61B 5/06* | (2006.01) | |
| *A61B 18/18* | (2006.01) | |
| *A61B 5/053* | (2006.01) | |
| *G01R 33/28* | (2006.01) | |
| *A61M 5/00* | (2006.01) | |
| *A61B 5/042* | (2006.01) | |
| *A61B 5/055* | (2006.01) | |
| *A61B 18/02* | (2006.01) | |
| *A61M 25/06* | (2006.01) | |
| *A61B 19/00* | (2006.01) | |
| *A61M 25/00* | (2006.01) | |
| *A61M 29/00* | (2006.01) | |
| *A61M 25/01* | (2006.01) | |
| *A61M 25/09* | (2006.01) | |

(52) U.S. Cl.
CPC ............... *A61B 5/062* (2013.01); *A61B 5/0044* (2013.01); *A61B 5/065* (2013.01); *A61B 18/18* (2013.01); *A61M 2025/0681* (2013.01); *A61B 5/053* (2013.01); *A61B 5/415* (2013.01); *A61B 2019/5236* (2013.01); *A61M 2025/0089* (2013.01); *G01R 33/287* (2013.01); *A61M 29/00* (2013.01); *A61M 5/00* (2013.01); *A61B 2019/5291* (2013.01); *A61B 5/0422* (2013.01); *A61M 2025/0166* (2013.01); *A61M 2025/09175* (2013.01); *A61B 5/055* (2013.01); *A61M 25/0127* (2013.01); *G01R 33/286* (2013.01); *A61M 25/01* (2013.01); *A61B 2019/5454* (2013.01); *A61B 18/02* (2013.01); *A61B 5/042* (2013.01); *A61B 5/418* (2013.01)
USPC ............................ 600/423; 600/410; 600/424

(58) Field of Classification Search
CPC .. G01R 33/285; G01R 33/286; G01R 33/287; G01R 33/34038; G01R 33/34046; G01R 33/34084; G01R 33/34092; A61B 19/20; A61B 19/2203
USPC .......... 600/407–429, 473–480; 607/119–123; 324/307–309, 318
See application file for complete search history.

(56) References Cited

U.S. PATENT DOCUMENTS

| | | |
|---|---|---|
| 3,499,435 A | 3/1970 | Rockwell et al. |
| 3,661,158 A | 5/1972 | Berkovits |
| 4,295,467 A | 10/1981 | Mann et al. |
| 4,431,005 A | 2/1984 | McCormick |
| 4,445,501 A | 5/1984 | Bresler |
| 4,572,198 A | 2/1986 | Codrington |
| 4,612,930 A | 9/1986 | Bremer |
| 4,639,365 A | 1/1987 | Sherry |
| 4,643,186 A | 2/1987 | Rosen et al. |
| 4,672,972 A | 6/1987 | Berke |
| 4,754,752 A | 7/1988 | Ginsburg et al. |
| 4,757,820 A | 7/1988 | Itoh |
| 4,766,381 A | 8/1988 | Conturo et al. |
| 4,791,934 A | 12/1988 | Brunnett |
| 4,793,359 A | 12/1988 | Sharrow |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,859,950 A | 8/1989 | Keren |
| 4,932,411 A | 6/1990 | Fritschy et al. |
| 4,951,672 A | 8/1990 | Buchwald et al. |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,078,140 A | 1/1992 | Kwoh |
| 5,095,911 A | 3/1992 | Pomeranz |
| 5,099,208 A | 3/1992 | Fitzpatrick et al. |
| 5,125,896 A | 6/1992 | Hojeibane |
| 5,151,856 A | 9/1992 | Halmann et al. |
| 5,154,179 A | 10/1992 | Ratner |
| 5,156,151 A | 10/1992 | Imran |
| 5,167,233 A | 12/1992 | Eberle et al. |
| 5,170,789 A | 12/1992 | Narayan et al. |
| 5,178,618 A | 1/1993 | Kandarpa |
| 5,190,046 A | 3/1993 | Shturman |
| 5,190,528 A | 3/1993 | Fonger et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,218,025 A | 6/1993 | Kurimoto et al. |
| 5,230,338 A | 7/1993 | Allen et al. |
| 5,246,438 A | 9/1993 | Langberg |
| 5,251,120 A | 10/1993 | Smith |
| 5,251,635 A | 10/1993 | Dumoulin et al. |
| 5,255,680 A | 10/1993 | Darrow et al. |
| 5,263,485 A | 11/1993 | Hickey |
| 5,271,400 A | 12/1993 | Dumoulin et al. |
| 5,275,163 A | 1/1994 | McKimmon et al. |
| 5,276,927 A | 1/1994 | Day |
| 5,284,144 A | 2/1994 | Delannoy et al. |
| 5,290,266 A | 3/1994 | Rohling et al. |
| 5,293,868 A | 3/1994 | Nardella |
| 5,297,549 A | 3/1994 | Beatty et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa |
| 5,347,221 A | 9/1994 | Rubinson |
| 5,348,010 A | 9/1994 | Schnall et al. |
| 5,352,979 A | 10/1994 | Conturo |
| 5,353,795 A | 10/1994 | Souza et al. |
| 5,355,087 A | 10/1994 | Claiborne et al. |
| 5,358,515 A | 10/1994 | Hurter et al. |
| 5,362,475 A | 11/1994 | Gries et al. |
| 5,365,928 A | 11/1994 | Rhinehart et al. |
| 5,370,644 A | 12/1994 | Langberg |
| 5,377,678 A | 1/1995 | Dumoulin et al. |
| 5,383,454 A | 1/1995 | Bucholz |
| 5,384,537 A | 1/1995 | Ito et al. |
| 5,389,101 A | 2/1995 | Heilbrun et al. |
| 5,391,199 A | 2/1995 | Ben-Haim |
| 5,394,873 A | 3/1995 | Kraemer et al. |
| 5,398,683 A | 3/1995 | Edwards et al. |
| 5,398,692 A | 3/1995 | Hickey |
| 5,405,346 A | 4/1995 | Grundy et al. |
| 5,409,008 A | 4/1995 | Svenson et al. |
| 5,413,104 A | 5/1995 | Buijs et al. |
| 5,415,163 A | 5/1995 | Harms et al. |
| 5,422,576 A | 6/1995 | Kao et al. |
| 5,433,198 A | 7/1995 | Desai |
| 5,433,717 A | 7/1995 | Rubinsky et al. |
| 5,436,564 A | 7/1995 | Kreger et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,462,055 A | 10/1995 | Casey et al. |
| 5,480,422 A | 1/1996 | Ben-Haim |
| 5,507,743 A | 4/1996 | Edwards et al. |
| 5,512,825 A | 4/1996 | Atalar et al. |
| 5,529,068 A | 6/1996 | Hoenninger, III et al. |
| 5,531,227 A | 7/1996 | Schneider |
| 5,546,940 A | 8/1996 | Panescu et al. |
| 5,546,951 A | 8/1996 | Ben-Haim |
| 5,558,093 A | 9/1996 | Pomeranz |
| 5,568,809 A | 10/1996 | Ben-Haim |
| 5,569,266 A | 10/1996 | Siczek |
| 5,577,502 A | 11/1996 | Darrow et al. |
| 5,588,432 A | 12/1996 | Crowley |
| 5,590,657 A | 1/1997 | Cain et al. |
| 5,617,026 A | 4/1997 | Yoshino et al. |
| 5,622,170 A | 4/1997 | Schulz |
| 5,634,467 A | 6/1997 | Nevo |
| 5,643,255 A | 7/1997 | Organ |
| 5,644,234 A | 7/1997 | Rasche et al. |
| 5,647,361 A | 7/1997 | Damadian |
| 5,657,755 A | 8/1997 | Desai |
| 5,662,108 A | 9/1997 | Budd et al. |
| 5,671,739 A | 9/1997 | Darrow et al. |
| 5,682,886 A | 11/1997 | Delp et al. |
| 5,682,897 A | 11/1997 | Pomeranz |
| 5,685,878 A | 11/1997 | Falwell et al. |
| 5,687,725 A | 11/1997 | Wendt |
| 5,694,945 A | 12/1997 | Ben-Haim |
| 5,706,823 A | 1/1998 | Wodlinger |
| 5,713,357 A | 2/1998 | Meulenbrugge et al. |
| 5,713,946 A | 2/1998 | Ben-Haim |
| 5,715,822 A | 2/1998 | Watkins et al. |
| 5,722,402 A | 3/1998 | Swanson et al. |
| 5,728,079 A | 3/1998 | Weber et al. |
| 5,738,096 A | 4/1998 | Ben-Haim |
| 5,739,691 A | 4/1998 | Hoenninger, III |
| 5,740,808 A | 4/1998 | Panescu et al. |
| 5,744,958 A | 4/1998 | Werne |
| 5,749,835 A | 5/1998 | Glantz |
| 5,754,085 A | 5/1998 | Danby et al. |
| 5,769,846 A | 6/1998 | Edwards et al. |
| 5,782,764 A | 7/1998 | Werne |
| 5,792,055 A | 8/1998 | McKinnon |
| 5,797,849 A | 8/1998 | Vesely et al. |
| 5,800,352 A | 9/1998 | Ferre et al. |
| 5,810,728 A | 9/1998 | Kuhn |
| 5,817,130 A | 10/1998 | Cox et al. |
| 5,820,580 A | 10/1998 | Edwards et al. |
| 5,833,608 A | 11/1998 | Acker |
| 5,836,874 A | 11/1998 | Swanson et al. |
| 5,840,025 A | 11/1998 | Ben-Haim |
| 5,840,031 A | 11/1998 | Crowley |
| 5,864,234 A | 1/1999 | Ludeke |
| 5,868,674 A | 2/1999 | Glowinski et al. |
| 5,882,304 A | 3/1999 | Ehnholm et al. |
| 5,891,047 A | 4/1999 | Lander et al. |
| 5,916,162 A | 6/1999 | Snelten et al. |
| 5,928,145 A | 7/1999 | Ocali et al. |
| 5,938,599 A | 8/1999 | Rasche et al. |
| 5,938,609 A | 8/1999 | Pomeranz |
| 5,944,022 A | 8/1999 | Nardella et al. |
| 5,951,472 A | 9/1999 | Van Vaals et al. |
| 5,961,528 A | 10/1999 | Birk et al. |
| 5,964,705 A | 10/1999 | Truwit et al. |
| 5,964,753 A | 10/1999 | Edwards |
| 5,978,696 A | 11/1999 | VomLehn et al. |

| | | |
|---|---|---|
| 6,004,269 A | 12/1999 | Crowley et al. |
| 6,014,579 A | 1/2000 | Pomeranz et al. |
| 6,014,581 A | 1/2000 | Whayne et al. |
| 6,019,725 A | 2/2000 | Vesely et al. |
| 6,023,165 A | 2/2000 | Damadian et al. |
| 6,023,636 A | 2/2000 | Wendt et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,045,553 A | 4/2000 | Iversen et al. |
| 6,052,614 A | 4/2000 | Morris, Sr. et al. |
| 6,052,618 A | 4/2000 | Dahlke et al. |
| 6,066,136 A | 5/2000 | Geistert |
| 6,067,371 A | 5/2000 | Gouge et al. |
| 6,070,094 A | 5/2000 | Swanson et al. |
| 6,071,281 A | 6/2000 | Burnside et al. |
| 6,073,039 A | 6/2000 | Berson |
| 6,076,007 A | 6/2000 | England et al. |
| 6,095,150 A | 8/2000 | Panescu et al. |
| 6,119,032 A | 9/2000 | Martin et al. |
| 6,128,522 A | 10/2000 | Acker et al. |
| 6,129,670 A | 10/2000 | Burdette et al. |
| 6,167,296 A | 12/2000 | Shahidi |
| 6,171,240 B1 | 1/2001 | Young et al. |
| 6,171,241 B1 | 1/2001 | McVeigh et al. |
| 6,179,833 B1 | 1/2001 | Taylor |
| 6,188,219 B1 | 2/2001 | Reeder et al. |
| 6,190,353 B1 | 2/2001 | Makower et al. |
| 6,192,144 B1 | 2/2001 | Holz |
| 6,201,394 B1 | 3/2001 | Danby et al. |
| 6,216,029 B1 | 4/2001 | Paltieli |
| 6,224,553 B1 | 5/2001 | Nevo |
| 6,226,542 B1 | 5/2001 | Reisfeld |
| 6,226,545 B1 | 5/2001 | Gilderdale |
| 6,231,570 B1 | 5/2001 | Tu et al. |
| 6,233,474 B1 | 5/2001 | Lemelson |
| 6,234,970 B1 | 5/2001 | Nevo et al. |
| 6,236,205 B1 | 5/2001 | Lüdeke et al. |
| 6,238,390 B1 | 5/2001 | Tu et al. |
| 6,241,725 B1 | 6/2001 | Cosman |
| 6,246,896 B1 * | 6/2001 | Dumoulin et al. ............. 600/411 |
| 6,256,529 B1 | 7/2001 | Holupka et al. |
| 6,263,229 B1 | 7/2001 | Atalar et al. |
| 6,272,370 B1 | 8/2001 | Gillies et al. |
| 6,272,371 B1 | 8/2001 | Shlomo |
| 6,280,385 B1 | 8/2001 | Melzer et al. |
| 6,284,970 B1 | 9/2001 | Buskmiller et al. |
| 6,284,971 B1 | 9/2001 | Atalar et al. |
| 6,289,233 B1 | 9/2001 | Dumoulin et al. |
| 6,301,496 B1 | 10/2001 | Reisfeld |
| 6,317,619 B1 | 11/2001 | Boernert et al. |
| 6,322,558 B1 | 11/2001 | Taylor et al. |
| 6,332,089 B1 | 12/2001 | Acker et al. |
| 6,368,285 B1 | 4/2002 | Osadchy et al. |
| 6,370,434 B1 | 4/2002 | Zhang et al. |
| 6,375,606 B1 | 4/2002 | Garibaldi et al. |
| 6,385,472 B1 | 5/2002 | Hall et al. |
| 6,385,476 B1 | 5/2002 | Osadchy et al. |
| 6,393,314 B1 | 5/2002 | Watkins et al. |
| 6,408,202 B1 | 6/2002 | Lima et al. |
| 6,422,748 B1 | 7/2002 | Shepherd et al. |
| 6,428,537 B1 | 8/2002 | Swanson et al. |
| 6,430,429 B1 | 8/2002 | Van Vaals |
| 6,431,173 B1 | 8/2002 | Hoffmann |
| 6,456,867 B2 | 9/2002 | Reisfeld |
| 6,470,204 B1 | 10/2002 | Uzgiris et al. |
| 6,475,223 B1 | 11/2002 | Werp et al. |
| 6,487,431 B1 | 11/2002 | Iwano et al. |
| 6,487,437 B1 | 11/2002 | Viswanathan et al. |
| 6,490,473 B1 | 12/2002 | Katznelson et al. |
| 6,506,189 B1 | 1/2003 | Rittman, II et al. |
| 6,516,213 B1 | 2/2003 | Nevo |
| 6,522,913 B2 | 2/2003 | Panescu et al. |
| 6,529,758 B2 | 3/2003 | Shahidi |
| 6,529,764 B1 | 3/2003 | Kato et al. |
| 6,534,982 B1 | 3/2003 | Jakab |
| 6,535,755 B2 | 3/2003 | Ehnholm |
| 6,546,273 B2 | 4/2003 | Suzuki et al. |
| 6,546,279 B1 | 4/2003 | Bova et al. |
| 6,549,800 B1 | 4/2003 | Atalar et al. |
| 6,556,009 B2 | 4/2003 | Kellman et al. |
| 6,556,695 B1 | 4/2003 | Packer et al. |
| 6,558,333 B2 | 5/2003 | Gilboa et al. |
| 6,558,382 B2 | 5/2003 | Jahns et al. |
| 6,575,969 B1 | 6/2003 | Rittman, II et al. |
| 6,591,128 B1 | 7/2003 | Wu et al. |
| 6,591,130 B2 | 7/2003 | Shahidi |
| 6,593,884 B1 | 7/2003 | Gilboa et al. |
| 6,594,517 B1 | 7/2003 | Nevo |
| 6,597,935 B2 | 7/2003 | Prince et al. |
| 6,600,319 B2 | 7/2003 | Golan |
| 6,603,997 B2 | 8/2003 | Doody |
| 6,606,513 B2 * | 8/2003 | Lardo et al. ................. 600/411 |
| 6,626,902 B1 | 9/2003 | Kucharczyk et al. |
| 6,628,980 B2 | 9/2003 | Atalar et al. |
| 6,633,773 B1 | 10/2003 | Reisfeld |
| 6,640,126 B2 | 10/2003 | Chang |
| 6,643,535 B2 | 11/2003 | Eum et al. |
| 6,650,923 B1 | 11/2003 | Lesh et al. |
| 6,650,927 B1 | 11/2003 | Keidar |
| 6,654,628 B1 | 11/2003 | Silber et al. |
| 6,668,184 B1 | 12/2003 | Kleiman |
| 6,675,033 B1 | 1/2004 | Lardo et al. |
| 6,675,037 B1 | 1/2004 | Tsekos |
| 6,687,530 B2 | 2/2004 | Dumoulin |
| 6,690,963 B2 | 2/2004 | Ben-Haim et al. |
| 6,701,176 B1 * | 3/2004 | Halperin et al. ............. 600/411 |
| 6,702,835 B2 | 3/2004 | Ginn |
| 6,711,429 B1 | 3/2004 | Gilboa et al. |
| 6,714,809 B2 | 3/2004 | Lee et al. |
| 6,725,079 B2 * | 4/2004 | Zuk et al. ...................... 600/414 |
| 6,740,883 B1 | 5/2004 | Stodilka et al. |
| 6,741,879 B2 | 5/2004 | Chang |
| 6,741,882 B2 | 5/2004 | Schäffter et al. |
| 6,743,248 B2 | 6/2004 | Edwards et al. |
| 6,771,067 B2 | 8/2004 | Kellman et al. |
| 6,780,183 B2 | 8/2004 | Jimenez, Jr. et al. |
| 6,785,572 B2 | 8/2004 | Yanof et al. |
| 6,788,062 B2 | 9/2004 | Schweikard et al. |
| 6,788,967 B2 | 9/2004 | Ben-Haim et al. |
| 6,793,664 B2 | 9/2004 | Mazzocchi et al. |
| 6,794,872 B2 | 9/2004 | Meyer et al. |
| 6,813,512 B2 | 11/2004 | Aldefeld et al. |
| 6,829,509 B1 | 12/2004 | MacDonald et al. |
| 6,847,210 B1 | 1/2005 | Eydelman et al. |
| 6,847,837 B1 | 1/2005 | Melzer et al. |
| 6,853,856 B2 | 2/2005 | Yanof et al. |
| 6,871,086 B2 | 3/2005 | Nevo et al. |
| 6,879,160 B2 | 4/2005 | Jakab |
| 6,892,090 B2 | 5/2005 | Verard et al. |
| 6,892,091 B1 | 5/2005 | Ben-Haim et al. |
| 6,896,678 B2 | 5/2005 | Tweardy |
| 6,898,302 B1 | 5/2005 | Brummer |
| 6,898,454 B2 | 5/2005 | Atalar et al. |
| 6,904,307 B2 * | 6/2005 | Karmarkar et al. ........... 600/423 |
| 6,920,347 B2 | 7/2005 | Simon et al. |
| 6,941,166 B2 | 9/2005 | MacAdam et al. |
| 6,949,929 B2 | 9/2005 | Gray et al. |
| 6,950,543 B2 | 9/2005 | King et al. |
| 6,958,035 B2 | 10/2005 | Friedman et al. |
| 6,961,602 B2 | 11/2005 | Fuimaono et al. |
| 6,961,608 B2 * | 11/2005 | Hoshino et al. ............... 600/423 |
| 6,975,896 B2 | 12/2005 | Ehnholm et al. |
| 6,980,865 B1 | 12/2005 | Wang et al. |
| 6,985,775 B2 | 1/2006 | Reinke et al. |
| 6,988,001 B2 | 1/2006 | Greatbatch et al. |
| 6,994,094 B2 | 2/2006 | Schwartz |
| 6,996,430 B1 | 2/2006 | Gilboa et al. |
| 7,001,383 B2 | 2/2006 | Keidar |
| 7,011,647 B2 | 3/2006 | Purdy et al. |
| 7,020,312 B2 | 3/2006 | Desmedt et al. |
| 7,027,851 B2 | 4/2006 | Mejia |
| 7,027,854 B2 | 4/2006 | Fuderer et al. |
| 7,047,060 B1 | 5/2006 | Wu |
| 7,048,716 B1 | 5/2006 | Kucharczyk et al. |
| 7,056,294 B2 | 6/2006 | Khairkhahan et al. |
| 7,081,748 B2 | 7/2006 | Jakab |

| Patent | Type | Date | Inventors | Class |
|---|---|---|---|---|
| 7,082,325 | B2 | 7/2006 | Hashimshony et al. | |
| 7,089,045 | B2 | 8/2006 | Fuimaono et al. | |
| 7,095,890 | B2 | 8/2006 | Paragios et al. | |
| 7,096,057 | B2 | 8/2006 | Hockett et al. | |
| 7,099,712 | B2 | 8/2006 | Fuimaono et al. | |
| 7,123,013 | B2 | 10/2006 | Gray | |
| 7,133,714 | B2 | 11/2006 | Karmarkar et al. | |
| 7,134,438 | B2 | 11/2006 | Makower et al. | |
| 7,154,498 | B2 | 12/2006 | Cowan et al. | |
| 7,155,271 | B2 | 12/2006 | Halperin et al. | |
| 7,162,293 | B2 | 1/2007 | Weiss | |
| 7,187,964 | B2 | 3/2007 | Khoury | |
| 7,204,840 | B2 | 4/2007 | Skakoon | |
| 7,205,768 | B2 | 4/2007 | Schulz et al. | |
| 7,209,777 | B2 | 4/2007 | Saranathan | |
| 7,211,082 | B2 | 5/2007 | Hall et al | |
| 7,220,265 | B2 | 5/2007 | Chanduszko et al. | |
| 7,225,012 | B1 | 5/2007 | Susil et al. | |
| 7,228,164 | B2 | 6/2007 | Fuimaono et al. | |
| 7,236,816 | B2* | 6/2007 | Kumar et al. | 600/411 |
| 7,239,400 | B2 | 7/2007 | Bock | |
| 7,241,283 | B2 | 7/2007 | Putz | |
| 7,255,691 | B2 | 8/2007 | Tolkoff et al. | |
| 7,263,397 | B2 | 8/2007 | Hauck et al. | |
| 7,276,905 | B2 | 10/2007 | Tamaroff et al. | |
| 7,280,863 | B2 | 10/2007 | Shachar | |
| 7,285,119 | B2 | 10/2007 | Stewart | |
| 7,289,843 | B2 | 10/2007 | Beatty et al. | |
| 7,302,285 | B2 | 11/2007 | Fuimaono et al. | |
| 7,306,593 | B2 | 12/2007 | Keidar et al. | |
| 7,307,420 | B2 | 12/2007 | Dumoulin | |
| 7,308,299 | B2 | 12/2007 | Burrell et al. | |
| 7,311,705 | B2 | 12/2007 | Sra | |
| 7,320,695 | B2 | 1/2008 | Carroll | |
| 7,343,195 | B2 | 3/2008 | Strommer et al. | |
| 7,347,829 | B2 | 3/2008 | Mark et al. | |
| 7,363,090 | B2 | 4/2008 | Halperin et al. | |
| 7,386,339 | B2 | 6/2008 | Strommer et al. | |
| 7,398,116 | B2 | 7/2008 | Edwards | |
| 7,412,276 | B2 | 8/2008 | Halperin et al. | |
| 7,415,301 | B2 | 8/2008 | Hareyama et al. | |
| 7,418,289 | B2 | 8/2008 | Hyde et al. | |
| 7,422,568 | B2 | 9/2008 | Yang et al. | |
| 7,440,792 | B2 | 10/2008 | Eggers | |
| 7,463,920 | B2 | 12/2008 | Purdy | |
| 7,473,843 | B2 | 1/2009 | Wang et al. | |
| 7,474,913 | B2 | 1/2009 | Durlak | |
| 7,477,054 | B2 | 1/2009 | Hoogenraad et al. | |
| 7,480,398 | B2 | 1/2009 | Kleen et al. | |
| 7,483,732 | B2 | 1/2009 | Zhong et al. | |
| 7,495,438 | B2 | 2/2009 | Prince et al. | |
| 7,499,743 | B2 | 3/2009 | Vass et al. | |
| 7,505,808 | B2 | 3/2009 | Anderson et al. | |
| 7,505,809 | B2 | 3/2009 | Strommer et al. | |
| 7,505,810 | B2 | 3/2009 | Harlev et al. | |
| 7,542,793 | B2 | 6/2009 | Wu et al. | |
| 7,551,953 | B2 | 6/2009 | Lardo et al. | |
| 7,561,906 | B2 | 7/2009 | Atalar et al. | |
| 7,587,234 | B2 | 9/2009 | Owens et al. | |
| 7,593,558 | B2 | 9/2009 | Boese | |
| 7,599,730 | B2 | 10/2009 | Hunter et al. | |
| 7,602,190 | B2 | 10/2009 | Piferi et al. | |
| 7,606,611 | B2 | 10/2009 | Speier | |
| 7,609,862 | B2 | 10/2009 | Black | |
| 7,623,903 | B2 | 11/2009 | Wacker | |
| 7,632,265 | B2 | 12/2009 | Hauck et al. | |
| 7,660,623 | B2 | 2/2010 | Hunter et al. | |
| 7,689,264 | B2 | 3/2010 | Nauerth | |
| 7,697,972 | B2 | 4/2010 | Verard et al. | |
| 7,720,520 | B2 | 5/2010 | Willis | |
| 7,725,157 | B2 | 5/2010 | Dumoulin et al. | |
| 7,725,160 | B2 | 5/2010 | Weber | |
| 7,725,161 | B2 | 5/2010 | Karmarkar et al. | |
| 7,726,708 | B2 | 6/2010 | Bourrieres | |
| 7,751,865 | B2 | 7/2010 | Jascob et al. | |
| 7,769,427 | B2 | 8/2010 | Shachar | |
| 7,777,485 | B2* | 8/2010 | Dumoulin et al. | 324/309 |
| 7,787,935 | B2 | 8/2010 | Dumoulin et al. | |
| 7,811,294 | B2 | 10/2010 | Strommer et al. | |
| 7,815,623 | B2 | 10/2010 | Bankiewicz | |
| 7,822,460 | B2 | 10/2010 | Halperin et al. | |
| 7,840,253 | B2* | 11/2010 | Tremblay et al. | 600/424 |
| 7,841,986 | B2 | 11/2010 | He | |
| 7,844,319 | B2* | 11/2010 | Susil et al. | 600/411 |
| 7,844,320 | B2 | 11/2010 | Shahidi | |
| 7,853,332 | B2 | 12/2010 | Olsen | |
| 7,881,769 | B2 | 2/2011 | Sobe | |
| 7,894,877 | B2 | 2/2011 | Lewin et al. | |
| 7,920,911 | B2* | 4/2011 | Hoshino et al. | 600/423 |
| 7,999,547 | B2 | 8/2011 | Green et al. | |
| 8,010,177 | B2 | 8/2011 | Csavoy et al. | |
| 8,016,857 | B2* | 9/2011 | Sater et al. | 606/213 |
| 8,221,442 | B2 | 7/2012 | Domb et al. | |
| 8,521,257 | B2 | 8/2013 | Whitcomb et al. | |
| 8,532,742 | B2 | 9/2013 | Unal et al. | |
| 2001/0025142 | A1 | 9/2001 | Wessels et al. | |
| 2002/0019629 | A1 | 2/2002 | Dietz et al. | |
| 2002/0019644 | A1 | 2/2002 | Hastings et al. | |
| 2002/0055678 | A1 | 5/2002 | Scott et al. | |
| 2002/0058868 | A1* | 5/2002 | Hoshino et al. | 600/423 |
| 2002/0072712 | A1* | 6/2002 | Nool et al. | 604/167.01 |
| 2002/0103430 | A1 | 8/2002 | Hastings et al. | |
| 2002/0169371 | A1 | 11/2002 | Gilderdale | |
| 2002/0177771 | A1 | 11/2002 | Guttman et al. | |
| 2003/0028095 | A1* | 2/2003 | Tulley et al. | 600/422 |
| 2003/0050557 | A1* | 3/2003 | Susil et al. | 600/424 |
| 2003/0055332 | A1 | 3/2003 | Daum et al. | |
| 2003/0078494 | A1 | 4/2003 | Panescu et al. | |
| 2003/0088181 | A1 | 5/2003 | Gleich et al. | |
| 2003/0093067 | A1 | 5/2003 | Panescu | |
| 2003/0097149 | A1* | 5/2003 | Edwards et al. | 606/214 |
| 2003/0100829 | A1 | 5/2003 | Zhong et al. | |
| 2003/0130577 | A1 | 7/2003 | Purdy et al. | |
| 2003/0158477 | A1 | 8/2003 | Panescu | |
| 2003/0208252 | A1 | 11/2003 | O'Boyle et al. | |
| 2003/0216642 | A1 | 11/2003 | Pepin et al. | |
| 2004/0006268 | A1 | 1/2004 | Gilboa et al. | |
| 2004/0015075 | A1* | 1/2004 | Kimchy et al. | 600/424 |
| 2004/0024308 | A1 | 2/2004 | Wickline et al. | |
| 2004/0030244 | A1 | 2/2004 | Garibaldi et al. | |
| 2004/0034297 | A1 | 2/2004 | Darrow et al. | |
| 2004/0046557 | A1* | 3/2004 | Karmarkar et al. | 324/322 |
| 2004/0049121 | A1 | 3/2004 | Yaron | |
| 2004/0054279 | A1 | 3/2004 | Hanley | |
| 2004/0064148 | A1 | 4/2004 | Daum et al. | |
| 2004/0073088 | A1 | 4/2004 | Friedman et al. | |
| 2004/0082948 | A1* | 4/2004 | Stewart et al. | 606/41 |
| 2004/0092813 | A1 | 5/2004 | Takizawa et al. | |
| 2004/0111022 | A1 | 6/2004 | Grabek et al. | |
| 2004/0116800 | A1 | 6/2004 | Helfer et al. | |
| 2004/0124838 | A1* | 7/2004 | Duerk et al. | 324/304 |
| 2004/0143180 | A1 | 7/2004 | Zhong et al. | |
| 2004/0152968 | A1 | 8/2004 | Iversen et al. | |
| 2004/0152974 | A1 | 8/2004 | Solomon | |
| 2004/0171934 | A1 | 9/2004 | Khan et al. | |
| 2004/0181160 | A1 | 9/2004 | Rudy | |
| 2004/0181177 | A1 | 9/2004 | Lee | |
| 2004/0199072 | A1 | 10/2004 | Sprouse et al. | |
| 2004/0220470 | A1* | 11/2004 | Karmarkar et al. | 600/423 |
| 2004/0225213 | A1 | 11/2004 | Wang et al. | |
| 2005/0010105 | A1 | 1/2005 | Sra | |
| 2005/0014995 | A1 | 1/2005 | Amundson | |
| 2005/0033164 | A1 | 2/2005 | Yatsuo et al. | |
| 2005/0054910 | A1 | 3/2005 | Tremblay et al. | |
| 2005/0054913 | A1 | 3/2005 | Duerk et al. | |
| 2005/0113874 | A1 | 5/2005 | Connelly | |
| 2005/0119556 | A1 | 6/2005 | Gillies et al. | |
| 2005/0143651 | A1 | 6/2005 | Verard et al. | |
| 2005/0154279 | A1 | 7/2005 | Li et al. | |
| 2005/0154281 | A1 | 7/2005 | Xue et al. | |
| 2005/0154282 | A1 | 7/2005 | Li et al. | |
| 2005/0165301 | A1 | 7/2005 | Smith et al. | |
| 2005/0171427 | A1 | 8/2005 | Nevo et al. | |
| 2005/0215886 | A1 | 9/2005 | Schmidt | |
| 2005/0222509 | A1 | 10/2005 | Neason | |
| 2005/0228252 | A1 | 10/2005 | Neason | |
| 2005/0256398 | A1 | 11/2005 | Hastings et al. | |
| 2005/0288599 | A1 | 12/2005 | MacAdam et al. | |

| | | |
|---|---|---|
| 2006/0009756 A1 | 1/2006 | Francischelli et al. |
| 2006/0025677 A1 | 2/2006 | Verard et al. |
| 2006/0052706 A1 | 3/2006 | Hynynen |
| 2006/0084867 A1 | 4/2006 | Tremblay et al. |
| 2006/0089624 A1 | 4/2006 | Voegele et al. |
| 2006/0100506 A1 | 5/2006 | Halperin et al. |
| 2006/0106303 A1 | 5/2006 | Karmarkar et al. |
| 2006/0116576 A1 | 6/2006 | McGee |
| 2006/0184011 A1 | 8/2006 | Macaulay et al. |
| 2006/0224062 A1 | 10/2006 | Aggarwal et al. |
| 2006/0241392 A1 | 10/2006 | Feinstein |
| 2006/0247521 A1 | 11/2006 | McGee |
| 2006/0247684 A1 | 11/2006 | Halperin et al. |
| 2006/0258934 A1 | 11/2006 | Zenge et al. |
| 2007/0049817 A1 | 3/2007 | Preiss |
| 2007/0055328 A1 | 3/2007 | Mayse et al. |
| 2007/0062547 A1 | 3/2007 | Pappone |
| 2007/0073135 A1 | 3/2007 | Lee |
| 2007/0073179 A1 | 3/2007 | Afonso |
| 2007/0083195 A1 | 4/2007 | Werneth |
| 2007/0088295 A1 | 4/2007 | Bankiewicz |
| 2007/0088416 A1 | 4/2007 | Atalar et al. |
| 2007/0100223 A1 | 5/2007 | Liao et al. |
| 2007/0100232 A1 | 5/2007 | Hiller et al. |
| 2007/0106148 A1 | 5/2007 | Dumoulin |
| 2007/0112398 A1 | 5/2007 | Stevenson |
| 2007/0156042 A1 | 7/2007 | Unal |
| 2007/0167726 A1 | 7/2007 | Unal et al. |
| 2007/0167736 A1 | 7/2007 | Dietz et al. |
| 2007/0167738 A1 | 7/2007 | Timinger et al. |
| 2007/0167745 A1 | 7/2007 | Case |
| 2007/0167801 A1 | 7/2007 | Webler et al. |
| 2007/0185485 A1 | 8/2007 | Hauck et al. |
| 2007/0208260 A1 | 9/2007 | Afonso |
| 2007/0233238 A1 | 10/2007 | Huynh et al. |
| 2007/0238970 A1 | 10/2007 | Kozerke et al. |
| 2007/0238978 A1 | 10/2007 | Kumar et al. |
| 2007/0238985 A1 | 10/2007 | Smith et al. |
| 2007/0249934 A1 | 10/2007 | Aksit et al. |
| 2007/0265521 A1 | 11/2007 | Redel et al. |
| 2007/0265642 A1 | 11/2007 | Chanduszko et al. |
| 2007/0270741 A1 | 11/2007 | Hassett et al. |
| 2007/0293724 A1 | 12/2007 | Saadat et al. |
| 2008/0009700 A1 | 1/2008 | Dumoulin et al. |
| 2008/0021336 A1 | 1/2008 | Dobak, III |
| 2008/0027696 A1 | 1/2008 | Pedain et al. |
| 2008/0032249 A1 | 2/2008 | Scommegna et al. |
| 2008/0033278 A1 | 2/2008 | Assif |
| 2008/0033281 A1 | 2/2008 | Kroeckel |
| 2008/0039897 A1 | 2/2008 | Kluge et al. |
| 2008/0049376 A1 | 2/2008 | Stevenson |
| 2008/0058635 A1 | 3/2008 | Halperin et al. |
| 2008/0097189 A1 | 4/2008 | Dumoulin et al. |
| 2008/0097191 A1 | 4/2008 | Dumoulin et al. |
| 2008/0119919 A1* | 5/2008 | Atalar et al. ............. 607/116 |
| 2008/0125802 A1 | 5/2008 | Carroll |
| 2008/0130965 A1 | 6/2008 | Avinash et al. |
| 2008/0139925 A1 | 6/2008 | Lubock et al. |
| 2008/0143459 A1 | 6/2008 | Vernickel et al. |
| 2008/0154253 A1 | 6/2008 | Damasco et al. |
| 2008/0171931 A1 | 7/2008 | Maschke |
| 2008/0177183 A1 | 7/2008 | Courtney et al. |
| 2008/0183070 A1 | 7/2008 | Unal et al. |
| 2008/0190438 A1 | 8/2008 | Harlev et al. |
| 2008/0214931 A1 | 9/2008 | Dickfeld |
| 2008/0215008 A1* | 9/2008 | Nance et al. ............. 604/164.03 |
| 2008/0231264 A1 | 9/2008 | Krueger et al. |
| 2008/0243081 A1* | 10/2008 | Nance et al. ............. 604/164.03 |
| 2008/0243218 A1 | 10/2008 | Bottomley et al. |
| 2008/0262584 A1 | 10/2008 | Bottomley et al. |
| 2008/0275395 A1 | 11/2008 | Asbury et al. |
| 2008/0287773 A1 | 11/2008 | Harvey et al. |
| 2008/0306375 A1 | 12/2008 | Sayler et al. |
| 2008/0306376 A1 | 12/2008 | Hyde et al. |
| 2009/0079431 A1 | 3/2009 | Piferi et al. |
| 2009/0082783 A1 | 3/2009 | Piferi |
| 2009/0088627 A1 | 4/2009 | Piferi et al. |
| 2009/0102479 A1 | 4/2009 | Smith et al. |
| 2009/0112082 A1 | 4/2009 | Piferi et al. |
| 2009/0112084 A1 | 4/2009 | Piferi et al. |
| 2009/0118610 A1 | 5/2009 | Karmarkar et al. |
| 2009/0118725 A1* | 5/2009 | Auth et al. ............. 606/33 |
| 2009/0118729 A1* | 5/2009 | Auth et al. ............. 606/42 |
| 2009/0131783 A1 | 5/2009 | Jenkins et al. |
| 2009/0143696 A1 | 6/2009 | Najafi et al. |
| 2009/0171184 A1 | 7/2009 | Jenkins et al. |
| 2009/0171421 A1 | 7/2009 | Atalar et al. |
| 2009/0306643 A1 | 12/2009 | Pappone et al. |
| 2010/0066371 A1 | 3/2010 | Vij |
| 2010/0198052 A1 | 8/2010 | Jenkins et al. |
| 2010/0286725 A1* | 11/2010 | Benjamin et al. ............. 606/213 |
| 2010/0312094 A1* | 12/2010 | Guttman et al. ............. 600/411 |
| 2010/0312095 A1* | 12/2010 | Jenkins et al. ............. 600/411 |
| 2010/0312096 A1* | 12/2010 | Guttman et al. ............. 600/411 |
| 2010/0317961 A1* | 12/2010 | Jenkins et al. ............. 600/411 |
| 2010/0317962 A1* | 12/2010 | Jenkins et al. ............. 600/411 |
| 2011/0040175 A1 | 2/2011 | Shahidi |
| 2011/0106131 A1* | 5/2011 | Argentine ............. 606/194 |
| 2011/0270192 A1* | 11/2011 | Anderson et al. ............. 604/164.1 |

FOREIGN PATENT DOCUMENTS

| | | |
|---|---|---|
| EP | 0466424 | 1/1992 |
| EP | 0498996 | 8/1992 |
| EP | 0557127 | 8/1993 |
| EP | 0673621 | 9/1995 |
| EP | 0701835 | 3/1996 |
| EP | 0701836 | 3/1996 |
| EP | 0702976 | 3/1996 |
| EP | 0732082 | 9/1996 |
| EP | 1 943 974 A1 | 7/2008 |
| JP | 62-16753 | 1/1987 |
| JP | 01-212569 | 8/1989 |
| JP | 2006-070902 | 3/1994 |
| JP | 09-094238 | 4/1997 |
| JP | 09-238924 | 9/1997 |
| JP | 09-299346 | 11/1997 |
| JP | 2001-238959 | 9/2001 |
| JP | 2003-325475 | 11/2003 |
| JP | 2004-113808 | 4/2004 |
| JP | 2006-296826 | 11/2006 |
| JP | 2006-334259 | 12/2006 |
| WO | WO/87/04080 | 7/1987 |
| WO | WO/92/10213 | 6/1992 |
| WO | WO/94/23782 | 10/1994 |
| WO | WO/95/04398 | 2/1995 |
| WO | WO/96/12972 | 5/1996 |
| WO | WO/97/29685 | 8/1997 |
| WO | WO/97/29710 | 8/1997 |
| WO | WO/97/40396 | 10/1997 |
| WO | WO/98/52461 | 11/1998 |
| WO | WO/98/55016 | 12/1998 |
| WO | WO/99/00052 | 1/1999 |
| WO | WO/99/16352 | 4/1999 |
| WO | WO/00/10456 | 3/2000 |
| WO | WO/00/25672 | 5/2000 |
| WO | WO/00/48512 | 8/2000 |
| WO | WO/00/57767 | 10/2000 |
| WO | WO/00/68637 | 11/2000 |
| WO | WO/01/01845 | 1/2001 |
| WO | WO/01/06925 | 2/2001 |
| WO | WO/01/12093 | 2/2001 |
| WO | WO/01/56469 A2 | 8/2001 |
| WO | WO 01/73461 A2 | 10/2001 |
| WO | WO/01/75465 | 10/2001 |
| WO | WO/01/87173 | 11/2001 |
| WO | WO/02/067202 | 8/2002 |
| WO | WO/02/083016 | 10/2002 |
| WO | WO/03/102614 | 12/2003 |
| WO | WO/2005/067563 | 7/2005 |
| WO | WO/2006/081409 | 8/2006 |
| WO | WO/2006/094156 | 9/2006 |
| WO | WO/2006/136029 | 12/2006 |
| WO | WO/2007/002541 | 1/2007 |
| WO | WO/2007/005367 | 1/2007 |
| WO | WO/ 2007/033240 A1 | 3/2007 |
| WO | WO/2007/066096 | 6/2007 |
| WO | WO/2008/015605 | 2/2008 |

| WO | WO/2008/023321 | 2/2008 |
| WO | WO/2008/082661 | 7/2008 |
| WO | WO/2008/129510 | 10/2008 |

OTHER PUBLICATIONS

Ackerman et al., "Rapid 3D Tracking of Small RF Coils [abstract]," Proceedings of the 5th Annual Meeting of ISMRM, Montreal, Canada pp. 1131-1132 (1986).
Atalar et al., "High Resolution Intravascular MRI and MRS using a Catheter Receiver Coil," MRM 36:596-605 (1996).
Bahnson, "Strategies to Minimize the Risk of Esophageal Injury During Catheter Ablation for Atrial Fibrillation: Catheter Ablation for AF Using a Combination of RF and Cryothermy Ablation—a Practical Approach," Pacing Clin. Electrophysiol. 32:248-260 (2009).
Bhakta et al., "Principles of Electroanatomic Mapping," Indian Pacing Electrophysiol. J. 8:32-50 (2008).
Biosense Webster, Inc., CARTO™ XP Electroanatomical Navigation System [Brochure] (2004) (accessed at www.biosensewebster.com/products/pdf/B0037Carto_V7_Bro_Fnl.pdf).
Bleier et al., "Real-time Magnetic Resonance Imaging of Laser Heat Deposition in Tissue," Mag. Reson. Med. 21:132-137 (1991).
Burke et al., "Integration of Cardiac Imaging and Electrophysiology During Catheter Ablation Procedures for Atrial Fibrillation," J. Electrocardiol. 39:S188-S192 (2006).
Chen et al., "Right Atrial Focal Fibrillation: Electrophysiologic Characteristics and Radiofrequency Catheter Ablation," J. Cardiovasc. Electrophysiol, 10:328-335 (1999).
Chorro et al., "Transcatheter ablation of the sinus node in dogs using high-frequency current," Eur Heart J 11:82-89 (1990).
Cummings et al., "Assessment of Temperature, Proximity, and Course of the Esophagus During Radiofrequency Ablation within the Left Atrium," Circulation 112:459-464 (2005).
Dick et al., "Magnetic Resonance Fluoroscopy Allows Targeted Delivery of Mesenchymal Stem Cells to Infarct Borders in Swine," Circulation, 108:2899-2904 (2003).
Dick et al., "Real-time MRI enables targeted injection of labeled stem cells to the border of recent porcine myocardial infarction based on functional and tissue characteristics," Proc. Intl. Soc. Mag. Reson. Med. 11, p. 365 (2003).
Dumoulin et al. "Real-Time Position Monitoring of Invasive Devices Using Magnetic Resonance," Mag. Reson. Med. 29:411-415 (1993).
Dumoulin et al., "Simultaneous Acquisition of Phase-Contrast Angiograms and Stationary-Tissue Images with Hadamard Encoding of Flow-induced Phase Shifts," JMRI 1:399-404 (1991).
Ector et al., Improved Efficiency in the EP Lab with syngo DynaCT Cardiac, AXIOM Innovations 26-32 (2008).
Edelman et al., "Magnetic Resonance Imaging," N. Engl. J. Med. 328:708-716 (1993).
Elgort et al., "Real-time Catheter Tracking and Adaptive Imaging," J. Magnetic Resonance Imaging 18:621-626 (2003).
Elgort, "Real-Time Catheter Tracking and Adaptive Imaging for Interventional Cardiovascular MRI," Case Western Reserve University student thesis (2005).
Fisher et al., "Atrial Fibrillation Ablation: Reaching the Mainstream: Methodology," Pacing Clin. Electrophysiol. 29:523-537 (2006).
Greenleaf et al., "Multidimensional Cardiac Imaging," Acoustical Imaging 20:403-411 (1993).
Grimson et al., "An Automatic Registration Method for Frameless Stereotaxy, Image Guided Surgery, and Enhanced Reality Visualization," IEEE Trans Med Imaging 15:129-140 (1996).
Guttman et al., "Imaging of Myocardial Infarction for Diagnosis and Intervention Using Real-Time Interactive MRI Without ECG-Gating or Breath-Holding," Mag. Reson. Med., 52:354-361 (2004).
Hamadeh et al., "Anatomy Based Multi-modal Medical Image Registration for Computer Integrated Surgery," SPIE 2355:178-188 (1994).
Hao and Hongo, "Use of Intracardiac Echocardiography During Catheter Ablation for Atrial Fibrillation: Maximizing Safety and Efficacy," EP Lab Digest 5(4) (2005).

Hillenbrand et al., "The Bazzoka Coil: A Novel Dual-Purpose Device for Active Visualization and Reduction of Cable Currents in Electrically Conductive Endovascular Instruments," Proc. Intl. Soc. Mag. Reson. Med. 13:197 (2005).
International Preliminary Report on Patentability Corresponding to International Application No. PCT/US2010/038816; Date of Mailing: Dec. 29, 2011; 5 pages.
International Preliminary Report on Patentability Corresponding to International Application No. PCT/US2010/038824; Date of Mailing: Dec. 29, 2011; 5 pages.
Jais et al., "Ablation Therapy for Atrial Fibrillation (AF): Past, Present and Future," Cardiovasc. Res. 54:337-346 (2002).
Jerwzewski et al., "Development of an MRI-Compatible Catheter for Pacing the Heart: Initial In Vitro and In Vivo Results," JMRI, ISHRM 6(6):948-949 (1996).
Jolesz et al., "MR Imaging of Laser-Tissue Interactions," Radiol. 168:249-253 (1988).
Kainz, "MR Heating Tests of MR Clinical Implants," J. Magnetic Resonance Imaging 26:450-451 (2007).
Kantor et al., "In vivo 31P Nuclear Magnetic Resonance Measurements in Canine Heart Using a Catheter-Coil," Circ. Res. 55:261-266 (1984).
Karmarkar, "An Active MRI Intramyocardial Injection Catheter," Proc. Intl. Soc. Mag. Reson. Med. 11:311 (2003).
Kerr et al,, "Real-time Interactive MRI on a Conventional Scanner," MRM 38:355-367 (1997).
Kumar, "MR Imaging with a Biopsy Needle," Proc. Intl. Sac, Mag. Reson. Med. 9:2148 (2001).
Lewin et al., "Needle localization in MR-guided biopsy and aspiration: effects of field strength, sequence design, and magnetic field orientation," Am. J. Roentgenol. 166:1337-1345 (1996).
Morady, "Mechanisms and Catheter Ablation Therapy of Atrial Fibrillation," Tex. Heart Inst. J. 32:199-201 (2005).
Nademanee et al., "A New Approach for Catheter Ablation of Atrial Fibrillation: Mapping of the Electrophysiologic Substrate," J. Am. Coll. Cardiol. 43:2044-2053 (2004).
Notification of Transmittal of the International Search Report and the Written Opinion of the International Searching Authority issued Jan. 25, 2011 by the Korean Intellectual Property Office for corresponding PCT Application No. PCT/US2010/038816.
Notification of Transmittal of the International Search Report and the Written Opinion of the International Searching Authority issued Jan. 25, 2011 by the Korean Intellectual Property Office for corresponding PCT Application No. PCT/US2010/038824.
Ocali et al., "Intravascular Magnetic Resonance Imaging Using a Loopless Catheter Antenna," Mag. Reson. Med. 37:112-118 (1997).
Oral et al., "A Tailored Approach to Catheter Ablation of Paroxysmal Atrial Fibrillation," Circulation 113:1824-1831 (2006).
Pfister, "Architectures for Real-Time Volume Rendering," Future Generations Computer Systems 15(1):1-9 (1999).
Pickens, "Magnetic Resonance Imaging," Handbook of Medical Imaging (Beutel, et al. eds.) 1:373-461 (2000).
Quick et al., "Endourethral MRI," Mag. Reson. Med. 45:138-146 (2001).
Ratnayaka et al., "Interventional cardiovascular magnetic resonance: still tantalizing," J. Cardiovasc. Mag. Reson.10:62 (2008).
Reddy et al., "Integration of Cardiac Magnetic Resonance Imaging with Three-Dimensional Electroanatomic Mapping to Guide Left Ventiruclar Catheter Manipulation: Feasibility in a Porcine Model of Healed Myocardial Infarction," J. Am. Coll. Cardiol. 44(11):2202-2213 (2004).
Robin Medical, Inc., "Sensors" Robin Medical Inc. (2009) (accessed at http://www.robinmedical.com/sensors.html).
Robin Medical, Inc., "The EndoScout® Tracking System" Robin Medical Inc. (2009) (accessed at http://www.robinmedical.com/endoscout.html).
Robin Medical, Inc., Endoscout® Tracking System for MRI [Brochure] (2009) (accessed at http://www.robinmedical.com/Robin_Medical_Brochure.pdf).
Schirra et al., "A View-sharing Compressed Sensing Technique for 3D Catheter Visualization from Bi-planar Views," Proc. Intl. Soc. Mag. Reson. Med, 17:68 (2009).

Siemens USA, "Siemens Medical Solutions Revolutionizes Electrophysiology with syngo® DynaCT Cardiac Enhancement 3D Visualization of the Left Atrium, Reducing the Need for Pre-Procedural CT or MR Imaging, and Facilitating Improved Workflow," Siemens USA (2007) (accessed at http://press.siemens.us/index.php?s=43&item=94).

Silverman et al., "Interactive MR-guided Biopsy in an Open Configuration MR Imaging System," Radiol. 197:175-181 (1995).

St. Jude Medical, Inc., "EnSite Array™ Catheter," St. Jude Medical (2011) (accessed at http://www.sjmprofessional.com/Products/Intl/Mapping-and-Visualization/EnSite-Array-Catheter.aspx).

St. Jude Medical, Inc., "EnSite Fusion™ Registration Module," St. Jude Medical (2011) (accessed at http://www.sjmprofessional.com/Products/US/Mapping-and-Visualization/EnSite-Fusion-Registration-Module.aspx).

St. Jude Medical, Inc., "EnSite NavX™ Navigation & Visualization Technology," St. Jude Medical (2011) (accessed at http://www.sjmprofessional.com/Products/US/Mapping-and-Visualization/EnSite-NavX-Navigation-and-Visualization-Technology.aspx).

St. Jude Medical, Inc., "EnSite Verismo™ Segmentation Tool," St. Jude Medical (2011) (accessed at http://www.sjmprofessional.com/Products/US/Mapping-and-Visualization/EnSite-Verismo-Segmentation-Tool.aspx).

St. Jude Medical, Inc., "EnSite™ System," St. Jude Medical (2011) (accessed at http://www.sjmprofessional.com/Products/US/Mapping-and-Visualization/EnSite-System.aspx).

St. Jude Medical, Inc., EnSite Fusion™ Registration Module Procedure Guide [Brochure] (2007) (accessed at http://www.ensitefusion.com/downloads/EnSiteFusionRegistrationModuleProcedureGuide.pdf).

Surgivision, Inc., "ClearTrace™ Cardiac Intervention System," Surgivision (2010) (accessed at http://www.surgivision.com/development).

Susil et al., "Multifunctional Interventional Devices for MRI: A Combined Electrophysiology/MRI Catheter," Mag. Reson. Med, 47:594-600 (2002).

Swain, "New MRI, Ultrasound Techniques Could Advance Breast Cancer Treatment," Medical Device & Diagnostic Industry Online (Apr. 1, 2004).

Torres et al,,"La cartografia electroanatomica (CARTO) en la ablacion de la fibrilacion auricular," Arch. Cardiol. Mex. 76(Supp 2):196-199 (2006).

Van Den Elsen et al., "Image Fusion Using Geometrical Features," SPIE 1808:172-186 (1992).

Weiss et al., "Transmission Line for Improved RF Safety of Interventional Devices," Mag. Reson. Med. 54:182-189 (2005).

Yang et al., "New Real-time Interactive Cardiac Magnetic Resonance Imaging System Complements Echocardiology," J. Am. Coll. Cardiol., 32:2049-2056 (1998).

Communication and extended European Search Report corresponding to European Patent Application No. EP 10 79 0114; Dated Apr. 19, 2013; 13 pages.

Office Action corresponding to Japanese Patent Application No. 2012-516263; Dispatch date: Feb. 18, 2014; 2 pages.

\* cited by examiner

*Primary Examiner* — Sanjay Cattungal

(74) *Attorney, Agent, or Firm* — Myers Bigel Sibley & Sajovec, P.A.

(57) ABSTRACT

An MRI-compatible catheter that reduces localized heating due to MR scanner-induced currents includes an elongated flexible shaft having a distal end portion and an opposite proximal end portion. A handle is attached to the proximal end portion and includes an electrical connector interface configured to be in electrical communication with an MRI scanner. One or more RF tracking coils are positioned adjacent the distal end portion of the shaft. Each RF tracking coil includes a conductive lead, such as a coaxial cable, that extends between the RF tracking coil and the electrical connector interface and electrically connects the RF tracking coil to an MRI scanner. In some embodiments of the present invention, the conductive lead has a length sufficient to define an odd harmonic/multiple of a quarter wavelength of the operational frequency of the MRI Scanner, and/or includes a series of pre-formed back and forth segments along its length.

19 Claims, 51 Drawing Sheets

"AUTO-VIEW" AUTOMATICALLY RECALLS PRESET SCAN PLANE AS AC NEARS TARGET

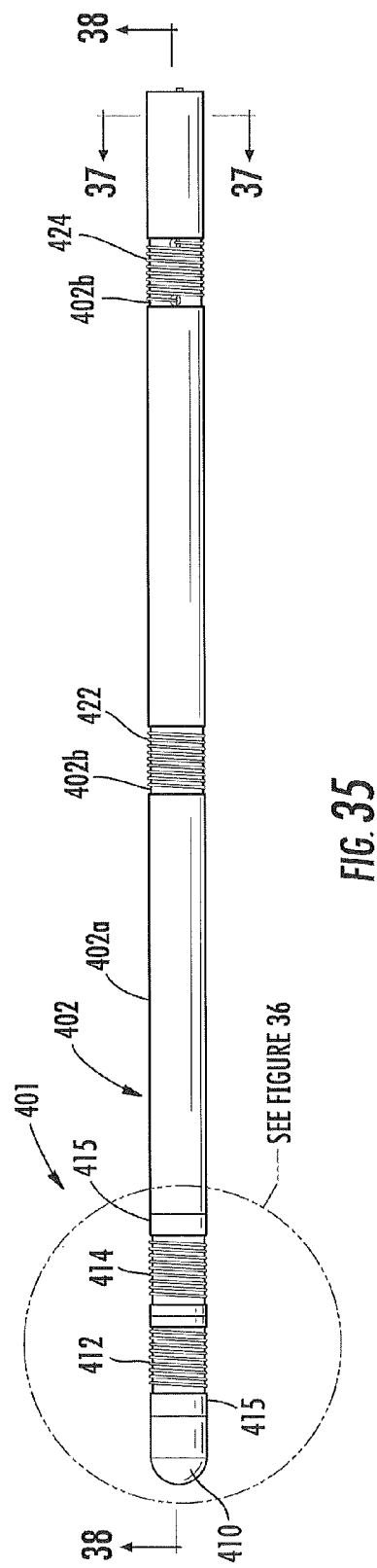
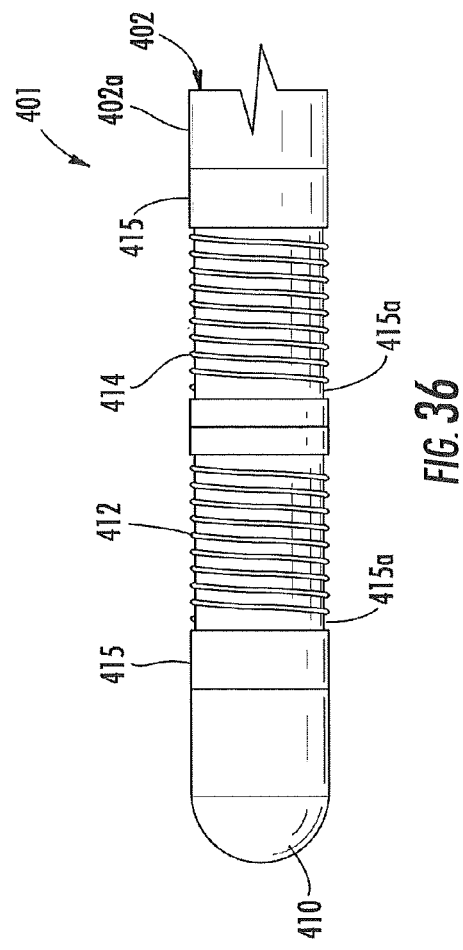
FIG. 35
FIG. 36

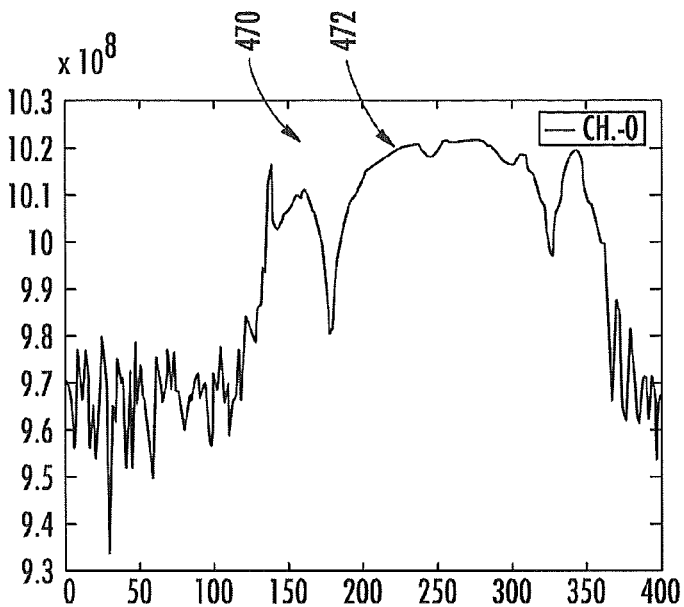
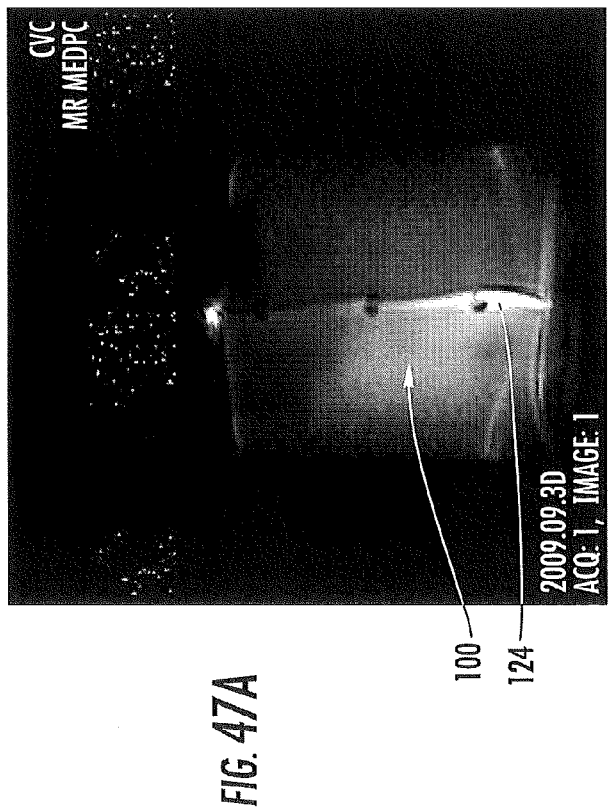
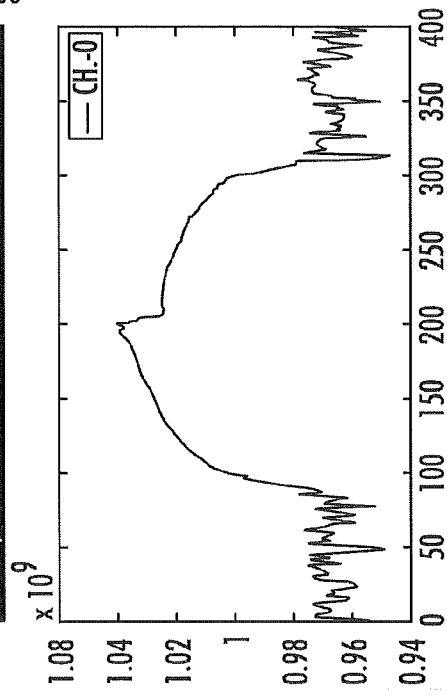
FIG. 47B
FIG. 47A
FIG. 47C

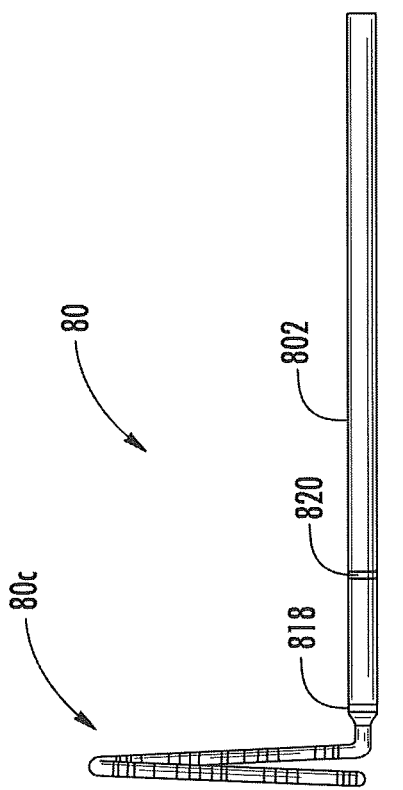
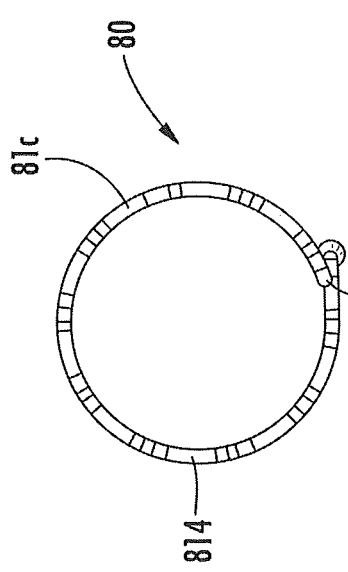
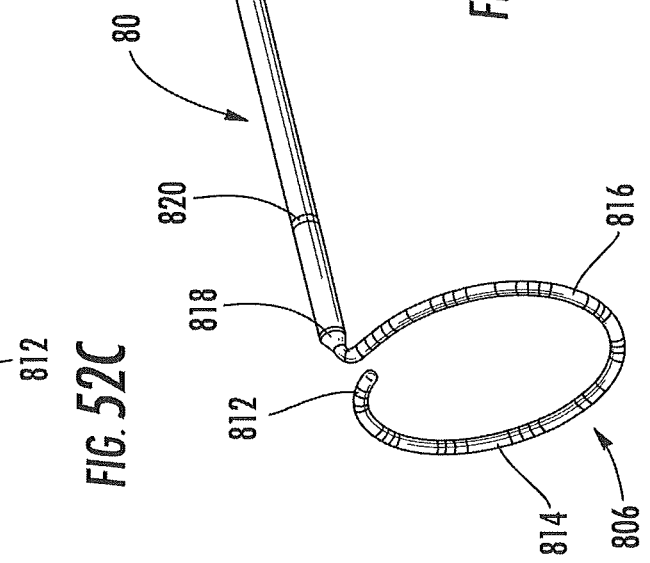
FIG. 52B
FIG. 52A
FIG. 52C

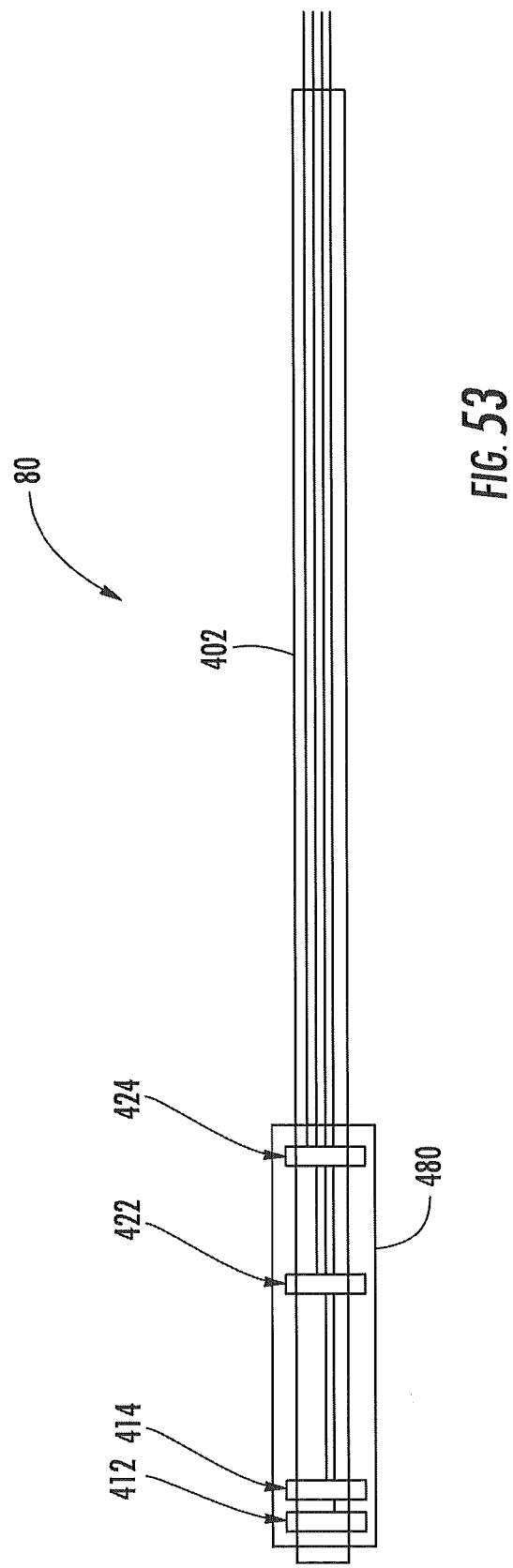

PEAK SNR COMPARISON 2 TURNS VS 4 TURN

|  | PEAK X PROJECTION | | PEAK Y PROJECTION | | PEAK Z PROJECTION | |
|---|---|---|---|---|---|---|
|  | 2 TURN | 4 TURN | 2 TURN | 4 TURN | 2 TURN | 4 TURN |
| TRACKING COIL #1 | 48 | 173 | 15 | 6 | 49 | 159 |
| TRACKING COIL #2 | 84 | 106 | 17 | 5 | 55 | 125 |
| TRACKING COIL #3 | 96 | 252 | 7 | 5 | 57 | 142 |
| TRACKING COIL #4 | 113 | 241 | 6 | 10 | 86 | 144 |

MRI-GUIDED CATHETERS

RELATED APPLICATIONS

This application is a continuation-in-part of U.S. patent application Ser. No. 12/816,803, filed Jun. 16, 2010, which claims the benefit of and priority to U.S. Provisional Patent Application No. 61/187,323 filed Jun. 16, 2009, to U.S. Provisional Patent Application No. 61/219,638 filed Jun. 23, 2009, and to U.S. Provisional Patent Application No. 61/261,103 filed Nov. 13, 2009, the disclosures of which are incorporated herein by reference as if set forth in their entireties. This application also is a continuation-in-part of International Patent Application No. PCT/US2012/026468, filed Feb. 24, 2012, which claims the benefit of and priority to U.S. Provisional Patent Application No. 61/446,329 filed Feb. 24, 2011.

FIELD OF THE INVENTION

The present invention relates to MRI-guided systems and may be particularly suitable for MRI-guided cardiac systems such as EP systems for treating Atrial Fibrillation (AFIB).

BACKGROUND

Heart rhythm disorders (arrhythmias) occur when there is a malfunction in the electrical impulses to the heart that coordinate how the heart beats. During arrhythmia, a heart may beat too fast, too slowly or irregularly. Catheter ablation is a widely used therapy for treating arrhythmias and involves threading a catheter through blood vessels of a patient and into the heart. In some embodiments, radio frequency (RF) energy may be applied through the catheter tip to destroy abnormal heart tissue causing the arrhythmia. In other embodiments a catheter tip may be configured to cryogenically ablate heart tissue.

Guiding the placement of a catheter during ablation therapy within the heart is important. Conventional catheter ablation procedures are conducted using X-ray and/or ultrasound imaging technology to facilitate catheter guidance and ablation of heart tissue. Conventional Cardiac EP (Electro-Physiology) Systems are X-ray based systems which use electroanatomical maps. Electroanatomical maps are virtual representations of the heart showing sensed electrical activity. Examples of such systems include the Carto® electroanatomic mapping system from Biosense Webster, Inc., Diamond Bar, Calif., and the EnSite NavX® system from Endocardial Solutions Inc., St. Paul, Minn.

Magnetic resonance imaging (MRI) has several distinct advantages over X-ray imaging technology, such as excellent soft-tissue contrast, the ability to define any tomographic plane, and the absence of ionizing radiation exposure. In addition, MRI offers several specific advantages that make it especially well suited for guiding various devices used in diagnostic and therapeutic procedures including: 1) real-time interactive imaging, 2) direct visualization of critical anatomic landmarks, 3) direct high resolution imaging, 4) visualization of a device-tissue interface, 5) the ability to actively track device position in three-dimensional space, and 6) elimination of radiation exposure.

Induced RF currents (referred to as RF coupling) on coaxial cables, electrical leads, guide wires, and other elongated devices utilized in MRI environments can be problematic. Such RF coupling may cause significant image artifacts, and may induce undesired heating and cause local tissue damage. To reduce the risk of tissue damage, it is desirable to reduce or prevent patient contact with cables and other conductive devices in an MRI environment. Such contact, however, may be unavoidable in some cases. For devices that are inserted inside the body, such as endorectal, esophageal, and intravascular devices, the risk of tissue damage may increase.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

In some embodiments of the present invention, an MRI-compatible ablation catheter includes an elongated flexible shaft having a distal end portion, an opposite proximal end portion, and at least one lumen extending between the proximal and distal end portions. A handle is attached to the proximal end portion, and includes a main body portion and an actuator (e.g., a lever, piston, thumb slider, knob, etc.) in communication with the shaft distal end portion and configured to articulate the shaft distal end portion. In some embodiments, the actuator is a piston that is movable between extended and retracted positions relative the handle main body portion. The handle includes an electrical connector interface configured to be in electrical communication with an MRI scanner.

The distal end portion of the shaft includes an ablation tip and at least one RF tracking coil positioned adjacent the ablation tip, and that includes a conductive lead, such as a coaxial cable, extending between the at least one RF tracking coil and the electrical connector interface and configured to electrically connect the at least one tracking coil to an MRI scanner. The conductive lead has a length sufficient to define an odd harmonic/multiple of a quarter wavelength of the operational frequency of the MRI Scanner. The at least one RF tracking coil also is electrically connected to a circuit that reduces coupling when the at least one RF tracking coil is exposed to an MRI environment. The shaft distal end portion also may include at least one sensing electrode configured to detect local electrical signals or properties, and a thermocouple for measuring temperature. In some embodiments, the at least one RF tracking coil at the distal end upstream of an ablation electrode on the tip of the catheter comprises a pair of RF tracking coils in adjacent spaced-apart relationship.

Each RF tracking coil can be about a 1-10 turn solenoid coil, and has a length in the longitudinal direction of the catheter of between about 0.25 mm and about 4 mm. In some embodiments, each RF tracking coil is recessed within the catheter shaft and a layer of MRI-compatible material overlies the RF tracking coil and is substantially flush with an outer surface of the catheter shaft. This MRI-compatible material can serve the function of a heat sink for reducing heating.

A pull wire can extend through a shaft lumen and has a distal end and an opposite proximal end. An exemplary pull wire is a Kevlar string/cable. The pull wire distal end is attached to the shaft distal end portion and the pull wire proximal end is attached to the piston. Movement of the piston causes articulation of the shaft distal end portion to facilitate positioning of the ablation tip during an ablation procedure. In some embodiments, the shaft distal end portion includes a biasing member that is configured to urge the shaft distal end portion to a non-articulated position.

In some embodiments, the shaft distal end portion includes at least one fluid exit port in fluid communication with an irrigation lumen that extends longitudinally through the catheter shaft lumen from the at least one exit port to the proximal end portion of the catheter shaft. The irrigation lumen is in fluid communication with a fluid/solution source at the proximal end portion of the catheter shaft.

In some embodiments of the present invention, an MRI-compatible mapping catheter includes an elongated flexible shaft having a distal end portion, an opposite proximal end portion, and at least one lumen extending between the proximal and distal end portions. A plurality of sensing electrodes are arranged in spaced-apart relationship at the shaft distal end portion, and at least one RF tracking coil is positioned at the shaft distal end portion and that includes a conductive lead configured to electrically connect the at least one tracking coil to an MRI scanner, wherein the conductive lead has a length sufficient to define an odd harmonic/multiple of a quarter wavelength of the operational frequency of the MRI Scanner. A handle attached to the proximal end portion and an actuator attached to the handle is in communication with the shaft distal end portion. Activation of the actuator causes articulation of the shaft distal end portion.

Each RF tracking coil can be about a 1-10 turn solenoid coil, and has a longitudinal length of between about 0.25 mm and about 4 mm. In some embodiments, each RF tracking coil is recessed within the catheter shaft and a layer of MRI-compatible material overlies the RF tracking coil and is substantially flush with an outer surface of the catheter shaft.

A pull wire can extend through a shaft lumen and has a distal end and an opposite proximal end. The pull wire distal end is attached to the shaft distal end portion and the pull wire proximal end is attached to the piston. Movement of the piston causes articulation of the shaft distal end portion to facilitate positioning of the ablation tip during an ablation procedure. In some embodiments, the shaft distal end portion includes a biasing member that is configured to urge the shaft distal end portion to a non-articulated position.

According to some embodiments of the present invention, an MRI guided interventional system includes at least one catheter configured to be introduced into a patient via a tortuous and/or natural lumen path, such as the ablation catheter and mapping catheter described above. The at least one catheter has an elongated flexible shaft with a distal end portion, an opposite proximal end portion, and at least one RF tracking coil connected to a channel of an MRI scanner. A circuit is adapted to communicate with and/or reside in the MRI Scanner, and is configured to: (a) obtain MR image data and generate a series of near real time (RT) MRI images of target anatomy of a patient during a surgical procedure using relevant anatomical scan planes associated with a 3-D MRI image space having a coordinate system; (b) identify coordinates associated with a location of at least a distal end portion of the at least one catheter using the coordinate system of the 3-D MRI image space; and (c) render near RT interactive visualizations of the at least one catheter in the 3-D image space with RT image data of target patient anatomical structure and a registered pre-acquired first volumetric model of the target anatomical structure of the patient, wherein the circuit illustrates the at least one catheter with a physical representation in the visualizations.

A display with a user interface in communication with the circuit is configured to display the visualizations during an MRI guided interventional procedure. The user interface is configured to allow a user to (a) rotate the visualizations and (b) alter a displayed visualization to include only a near RT image of the target anatomy, to include the near RT image of the anatomy and the registered model of the anatomical structure, or to include only the registered model of the anatomical structure. The MRI Scanner is configured to interleave signal acquisition of tracking signals from the at least one tracking coil with image data for the near RT MRI images, and the circuit is configured to electronically track the at least one catheter in the 3-D image space independent of scan planes used to obtain the MR image data so that the at least one catheter is not required to be in any of the relevant anatomical scan planes used to obtain MR image data for the at least one near RT MRI image, and wherein the distal end portion of the at least one catheter can take on a curvilinear shape. Also, the circuit is configured to calculate a device-tissue interface location proximate a tip location of the at least one catheter in the three dimensional image space, and is configured to project axially forward a defined distance beyond the tip to define the device-tissue interface. The calculated tissue interface location is used to automatically define at least one scan plane used to obtain the MR image data during and/or proximate in time to a procedure using the at least one catheter.

According to some embodiments of the present invention, an MRI-compatible catheter that reduces localized heating due to MR scanner-induced currents includes an elongated flexible shaft having a distal end portion and an opposite proximal end portion. A handle is attached to the proximal end portion and includes an electrical connector interface configured to be in electrical communication with an MRI scanner. One or more RF tracking coils are positioned adjacent the distal end portion of the shaft. Each RF tracking coil includes a conductive lead, such as a coaxial cable, that extends between the RF tracking coil and the electrical connector interface and electrically connects the RF tracking coil to an MRI scanner. In some embodiments of the present invention, the conductive lead has a length sufficient to define an odd harmonic/multiple of a quarter wavelength of the operational frequency of the MRI Scanner, and/or includes a series of pre-formed back and forth segments along its length. In some embodiments of the present invention, the conductive lead is a coaxial cable that includes a self-resonant cable trap, such as, for example, a 60-turn inductor.

In some embodiments of the present invention, the catheter includes one or more sensing electrodes at the shaft distal end portion. One or more of the sensing electrodes is electrically connected to a high impedance resistor, for example, a resistor having an impedance of, for example, at least about 5,000 ohms.

In some embodiments of the present invention, the catheter includes a tuning circuit that is configured to stabilize tracking signals generated by one or more RF tracking coils. The tuning circuit may be located within the handle of the catheter.

In some embodiments of the present invention, a sheath surrounds at least a portion of the elongated shaft and includes at least one RF shield coaxially disposed therewithin. Each RF shield includes elongated inner and outer tubular conductors. The inner and outer conductors each have respective opposite first and second end portions. An elongated tubular dielectric layer of MRI compatible material is sandwiched between the inner and outer conductors and surrounds the inner conductor. Only the respective first end portions of the inner and outer conductors are electrically connected. The second end portions are electrically isolated from each other. In some embodiments, the inner and outer conductors comprise conductive foil, conductive braid, or a film with a conductive surface. A plurality of RF shields may be disposed within the sheath in end-to-end spaced-apart relationship.

In some embodiments of the present invention, at least one RF shield coaxially disposed within the flexible shaft of the catheter. Each RF shield includes elongated inner and outer tubular conductors. The inner and outer conductors each have respective opposite first and second end portions. An elongated tubular dielectric layer of MRI compatible material is sandwiched between the inner and outer conductors and surrounds the inner conductor. Only the respective first end portions of the inner and outer conductors are electrically connected. The second end portions are electrically isolated from each other. In some embodiments, the inner and outer conductors comprise conductive foil, conductive braid, or a film with a conductive surface. A plurality of RF shields may be disposed within the flexible shaft of the catheter in end-to-end spaced-apart relationship.

According to some embodiments of the present invention, the catheter is an ablation catheter with an ablation tip at the shaft distal end portion. An RF conductor extends longitudinally within the shaft from the ablation tip to the electrical connector interface at the handle and connects the ablation tip to an RF generator. The RF conductor includes a series of pre-formed back and forth segments along its length.

According to some embodiments of the present invention, an MRI-compatible catheter that reduces localized heating due to MR scanner-induced currents includes an elongated flexible shaft having a distal end portion and an opposite proximal end portion. The catheter includes an electrical connector interface that is configured to be in electrical communication with an MRI scanner. The catheter also includes an ablation tip at the flexible shaft distal end portion, at least one RF tracking coil positioned adjacent the flexible shaft distal end portion, and at least one sensing electrode at the shaft distal end portion. An RF conductor extends longitudinally within the flexible shaft to the electrical connector interface and connects the ablation tip to an RF generator. In some embodiments, the RF conductor includes a series of back and forth segments along its length.

A conductive lead extends between the at least one RF tracking coil and the electrical connector interface and is configured to electrically connect the at least one tracking coil to the MRI scanner. In some embodiments, at least one self-resonant cable trap is in communication with the at least one RF tracking coil. An exemplary self-resonant cable trap includes an inductor having between about twenty (20) turns and about one-hundred (100) turns. In some embodiments, a self-resonant cable trap may include an inductor having about sixty (60) turns. In some embodiments, the conductive lead includes a series of pre-formed back and forth segments along its length. In some embodiments, the conductive lead is a coaxial cable. In some embodiments, the conductive lead has a length sufficient to define an odd harmonic/multiple of a quarter wavelength of an operational frequency of the MRI Scanner.

According to some embodiments of the present invention, the at least one RF tracking coil comprises a plurality of tracking coils, each attached to a separate conductive lead, and wherein each conductive lead includes a series of back and forth segments along its length. In some embodiments, each conductive lead may have a length sufficient to define an odd harmonic/multiple of a quarter wavelength of an operational frequency of the MRI Scanner.

In some embodiments of the present invention, the at least one RF tracking coil comprises between 1-10 coil turns and/or has a length along a longitudinal direction of the catheter of between about 0.25 mm and about 4 mm.

In some embodiments, at least one high impedance resistor is in communication with the at least one sensing electrode.

In some embodiments, the ablation tip comprises platinum.

In some embodiments, the catheter includes at least one fluid exit port at the flexible shaft distal end portion. The at least one fluid exit port is in fluid communication with an irrigation lumen that extends longitudinally through the flexible shaft from the at least one fluid exit port.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

FIG. 35 is a side view of the distal end portion of the ablation catheter of FIG. 31, according to some embodiments of the present invention.

FIG. 36 is an enlarged partial view of the tip portion of the ablation catheter of FIG. 35.

FIG. 47A is an MRI image of the ablation catheter of FIG. 31 in a 3.0 T MRI environment with the RF tracking coil circuit of FIG. 46 not being utilized with respective multiple RF tracking coils.

FIG. 47B illustrates MRI signal strength of the MRI image of FIG. 47A in the Z direction.

FIG. 47C illustrates MRI signal strength of the MRI image of FIG. 47A in the X direction.

FIG. 52A is a partial perspective view of the distal end of a loop catheter, according to some embodiments of the present invention.

FIG. 52B is a side view of the loop catheter of FIG. 52A.

FIG. 52C is an end view of the loop catheter of FIG. 52A.

FIG. 53 is a side view of the distal end of an ablation catheter, according to other embodiments of the present invention.

DETAILED DESCRIPTION

Figure 1:
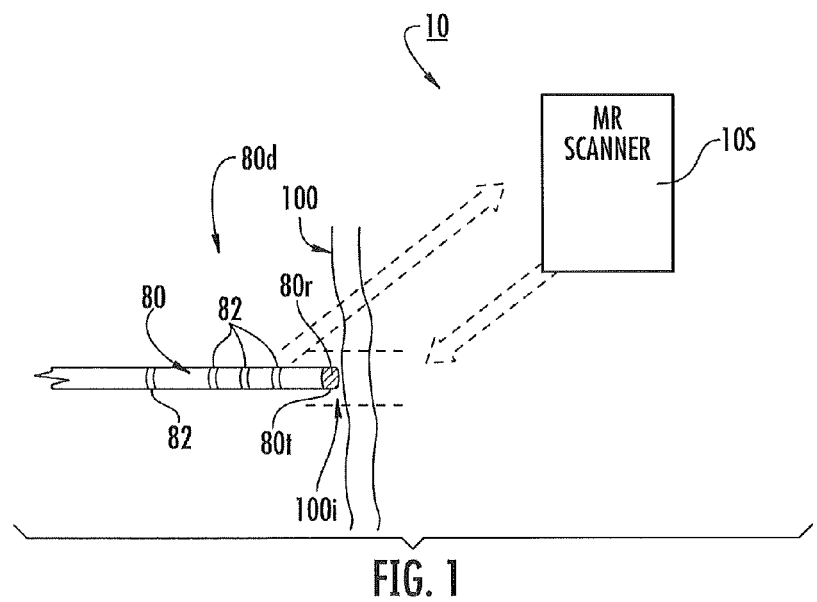
FIG. 1 is a schematic illustration of an MRI-guided system configured to show a device tissue interface using near RT MRI data according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "circuit" refers to an entirely software embodiment or an embodiment combining software and hardware aspects, features and/or components (including, for example, at least one processor and software associated therewith embedded therein and/or executable by and/or one or more Application Specific Integrated Circuits (ASICs), for programmatically directing and/or performing certain described actions or method steps). The circuit can reside in one location or multiple locations, it may be integrated into one component or may be distributed, e.g., it may reside entirely in an MR Scanner control cabinet, partially in the MR Scanner control cabinet, totally in a separate component or system such as a clinician workstation but communicate with MR Scanner electronics and/or in an interface therebetween, in a remote processor and combinations thereof.

The term "pre-set scan plane" refers to scan planes electronically (programmatically) defined for subsequent use by an MRI Scanner as being associated with a location of relevant anatomical tissue of a patient during a MRI guided therapeutic or diagnostic procedure. The pre-set scan planes can be defined based on a volumetric model or map of patient anatomical structure that is subsequently registered or aligned in 3-D imaging space and can be used to acquire near real-time MR image data of patient tissue. The actual pre-set scan planes are typically electronically defined after the model used to select a desired spatial location of a corresponding relevant scan plane is registered to the 3-D imaging space.

The term "map" is used interchangeably with the term "model" and refers to a volumetric rendering of a patient's target anatomy. The term "tissue characterization (or characteristic) map" refers to a rendered volumetric (typically 3-D, 4-D or 4-DMP) visualization and/or image of a target anatomical structure or portion thereof showing one or more selected tissue parameters, conditions, or behaviors of cardiac tissue using MR image data, e.g., the tissue characterization map is a rendered partial or global anatomical map that shows at least one defined tissue characteristic of the target anatomy, e.g., heart or portion thereof (for example, the left atrium) in a manner that illustrates relative degrees or measures of the tissue characteristic(s) of interest, typically in different colors, opacities and/or intensities. Notably, a tissue characterization map or model is to be contrasted with an electroanatomical (EA) map or model which is based on sensed electrical activity of different regions of the heart rather than on MR image data. In some embodiments, tissue data from an electroanatomical map and/or the tissue characteristic map can be selectively turned on and off (on a display) with respect to a pre-acquired model of the patient's anatomical structure (e.g., Left Atrium). A tissue characteristic map may be included with an EA model and/or two or more tissue characteristic maps may be merged into or shown as a composite map or may be shown overlying and aligned with one another. Thus, the visualizations can use one or both types of volumetric tissue maps, shown separately, overlaid on each other and/or integrated as a composite map.

The actual visualization can be shown on a screen or display so that the map of the anatomical structure is in a flat 2-D and/or in 2-D what appears to be 3-D volumetric images with data representing features or electrical output with different visual characteristics such as with differing intensity, opacity, color, texture and the like. A 4-D map can either illustrate a 3-D anatomical structure (e.g., heart) with movement (e.g., a beating heart and/or a heart with blood flow, breathing lungs or other moving structure) or show additional information over a 3-D anatomic model of the contours of the heart or portions thereof. The term "heart" can include adjacent vasculature, e.g., the branching of the pulmonary veins.

The term "4-D multiparametric visualization" (4-DMP) means a 4-D visualization image (e.g., a 3-D image of a beating heart) with functional spatially encoded or correlated information shown on the visualization. The 4-DMP visualization can be provided with fMRI data and/or one or more tools used to provide the spatially correlated functional data (e.g., electrical) data of the heart based on the 3-D model of the tool. Again, the 3-D, 4-D and/or 4-DMP visualizations are not merely an MRI image or MRI images of the patient during a procedure but are rendered visualizations that can combine multiple sources of data to provide a visualization of spatially encoded function with anatomical shape. Thus, the visualizations can comprise a rendered model of the patient's target anatomy with a rendered visualization of at least one medical device in an intrabody location with respect to the model and along with near RT MRI image data of the anatomical structure. The figures may include prophetic examples of screen shots of visualizations and the like and do not necessarily represent actual screen shots of a surgical system/display.

The term "close-up" means that the associated image is shown enlarged relative to a global image or typical navigation view to show local tissue. The term "high-resolution" means that the image data is obtained with higher resolution than normal image data (usually requiring longer scan times and/or using an internal antenna to increase SNR). For example, the local tissue ablation views may be shown in higher resolution than MRI images in the navigation view. The term en face refers to a view through a tissue wall (e.g., myocardial wall) and substantially parallel (tangent) to the surface.

The term "programmatically" means that the operation or step can be directed and/or carried out by a digital signal processor and/or computer program code. Similarly, the term "electronically" means that the step or operation can be carried out in an automated manner using electronic components rather than manually or using merely mental steps.

The term "target ablation path" describes a desired lesion pattern that is selected to create a desired electrical isolation in the cardiac tissue to treat the at-risk pathology/condition (e.g., AFIB). The target ablation path is not required to be followed in any particular direction or order. The path may include one or more continuous and/or contiguous lesion and/or several non-continuous or non-contiguous lesions. The lesions may be linear (whether straight or with a curvature such as circular or curvilinear). In any one interventional procedure, the physician can define one or more target paths to create the desired pattern/isolation. According to some embodiments, the target ablation path can be used to electronically define associated physical limits associated with the acceptable maximum boundary limits (e.g., width, perimeter and the like) of the target ablation path.

At least a portion of an intrabody medical device is tracked and its position identified in 3-D imaging space (e.g., X, Y, Z coordinates), according to embodiments of the present invention. Various location tracking means for the tool and/or registration means for the catheter to the imaging space can be employed. For example, the intrabody device can include fiducial markers or receive antennas combinations of same. The term "fiducial marker" refers to a marker that can be identified using electronic image recognition, electronic interrogation of MRI image data, or three-dimensional electrical signals to define a position and/or find the feature or component in 3-D space. The fiducial marker can be provided in any suitable manner, such as, but not limited to a geometric shape of a portion of the tool, a component on or in the tool, a coating or fluid-filled coating (or combinations of different types of fiducial markers) that makes the fiducial marker(s) MRI-visible that are active or passive (e.g., if passive, the marker does not provide MR signal) with sufficient intensity for identifying location and/or orientation information for the tool and/or components thereof in 3-D space. As will be discussed further below, in particular embodiments, the device comprises at least one tracking coil electrically connected to the MRI Scanner that generates signals that are detected (received) by the MR Scanner and used to identify respective locations of the coils in a 3-D coordinate system of the imaging space, and hence the device with such tracking coils, in the 3-D image space.

The terms "MRI or MR Scanner" are used interchangeably to refer to a Magnetic Resonance Imaging system and includes the magnet, the operating components, e.g., RF amplifier, gradient amplifiers and operational circuitry including, for example, processors (the latter of which may be held in a control cabinet) that direct the pulse sequences, select the scan planes and obtain MR data. Embodiments of the present invention can be utilized with any MRI Scanner including, but not limited to, GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio.

The term "RF safe" means that the catheter and any (conductive) lead is configured to operate safely when exposed to RF signals, particularly RF signals associated with MRI systems, without inducing unplanned current that inadvertently unduly heats local tissue or interferes with the planned therapy. The term "MRI visible" means that the device is visible, directly or indirectly, in an MRI image. The visibility may be indicated by the increased SNR of the MRI signal proximate the device. The device can act as an MRI receive antenna to collect signal from local tissue and/or the device actually generates MRI signal itself, such as via suitable medical grade hydro-based coatings, fluid (e.g., aqueous fluid) filled channels or lumens. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T, typically above 1.0 T, and more typically between about 1.5 T and 10 T. Embodiments of the invention may be particularly suitable for 1.5 T and/or 3.0 T systems.

Generally stated, advantageously, a system according to embodiments of the present invention can be configured so that the surgical space is the imaging space and the tracking is performed in the imaging space so that there is no requirement to employ a discrete tracking system that must then be registered to the imaging space. In some embodiments, the tracking is carried out in the same 3-D imaging space but the flexible intrabody medical device is tracked independent of the imaging scan planes used to obtain the MR image data for generating images of local anatomy and is shown as a physical representation in the visualization.

The term "near real time" refers to both low latency and high frame rate. Latency is generally measured as the time from when an event occurs to display of the event (total processing time). For tracking, the frame rate can range from between about 100 fps (frames per second) to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. For lesion imaging, a new image can be generated about every 1-7 s, depending on the sequence used. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., flexible catheter using the tracking coil data) and the near RT MR image(s) is generated.

In some embodiments, MR image data is obtained during an active treatment such as during an ablation, delivery of a drug or other material, valve repair or replacement, lining repair, and the like, and the resultant visualization(s) with the flexible intrabody device used for this treatment (e.g., catheter, needle and the like) along with one or more near RT MR images of local anatomy is substantially continuously generated. In some particular embodiments, the system is a cardiac EP system used to place a lesion pattern of transmural lesions that creates a desired electrical isolation in the cardiac tissue to treat the at-risk pathology/condition (e.g., AFIB). The ablations are not required to be followed in any particular direction or order. The ablation can be carried out to generate one or more continuous and/or contiguous lesions and/or several non-continuous or non-contiguous lesions. The lesions may be contiguous (whether straight or with a curvature such as circular or curvilinear).

The term "intrabody device" is used broadly to refer to any diagnostic or therapeutic medical device including, for example, catheters, needles (e.g., injection, suture, and biopsy), forceps (miniature), knives or other cutting members, ablation or stimulation probes, injection or other fluid delivery cannulas, mapping or optical probes or catheters, sheaths, guidewires, fiberscopes, dilators, scissors, implant material delivery cannulas or barrels, and the like, typically having a size that is between about 5 French to about 12 French, but other sizes may be appropriate.

The term "tracking member", as used herein, includes all types of components that are visible in an MRI image including miniature RF tracking coils, passive markers, and receive antennas. In some embodiments of the present invention a miniature RF tracking coil can be connected to a channel of an MRI Scanner. The MR Scanner can be configured to operate to interleave the data acquisition of the tracking coils with the image data acquisition. The tracking data is acquired in a 'tracking sequence block' which takes about 10 msec (or less). In some embodiments, the tracking sequence block can be executed between each acquisition of image data (the 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

MRI has several distinct advantages over X-ray imaging technology, such as: excellent soft-tissue contrast, the ability to define any tomographic plane, and the absence of ionizing radiation exposure. In addition, MRI offers several specific advantages that make it especially well suited for guiding transseptal puncture procedures including: 1) near real-time interactive imaging, 2) direct visualization of critical endocardial anatomic landmarks, 3) direct high resolution imaging of the septum, including the fossa ovalis, 4) visualization of the needle tip-tissue interface, 5) the ability to actively track needle position in three-dimensional space, and 6) elimination of radiation exposure.

Embodiments of the present invention can be configured to guide and/or place diagnostic or interventional devices in an MRI environment (e.g., interventional medical suite) to any desired internal region of a subject of interest, including, in some embodiments, to a cardiac location. The subject can be animal and/or human subjects.

Some embodiments of the invention provide systems that can be used to ablate tissue for treating cardiac arrhythmias, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

FIG. 1 illustrates an MRI interventional system 10 with a scanner 10S and a flexible intrabody medical device 80 (e.g., an ablation catheter, mapping catheter, etc.) proximate target tissue 100 at a device-tissue interface 100i. The system 10 can be configured to electronically track the 3-D location of the device 80 in the body and identify and/or "know" the location of the tip portion 80t of the device 80 (e.g., the ablation tip) in a coordinate system associated with the 3-D imaging space. As shown in FIG. 1, the device 80 can include a plurality of spaced apart tracking members 82 on a distal end portion thereof. In a particular embodiment, the device 80 can be an ablation catheter and the tip 80t can include an ablation electrode 80e (typically at least one at a distal end portion of the device). Where used, the electrode 80e can be both a sensing and ablation electrode.

Figure 2:
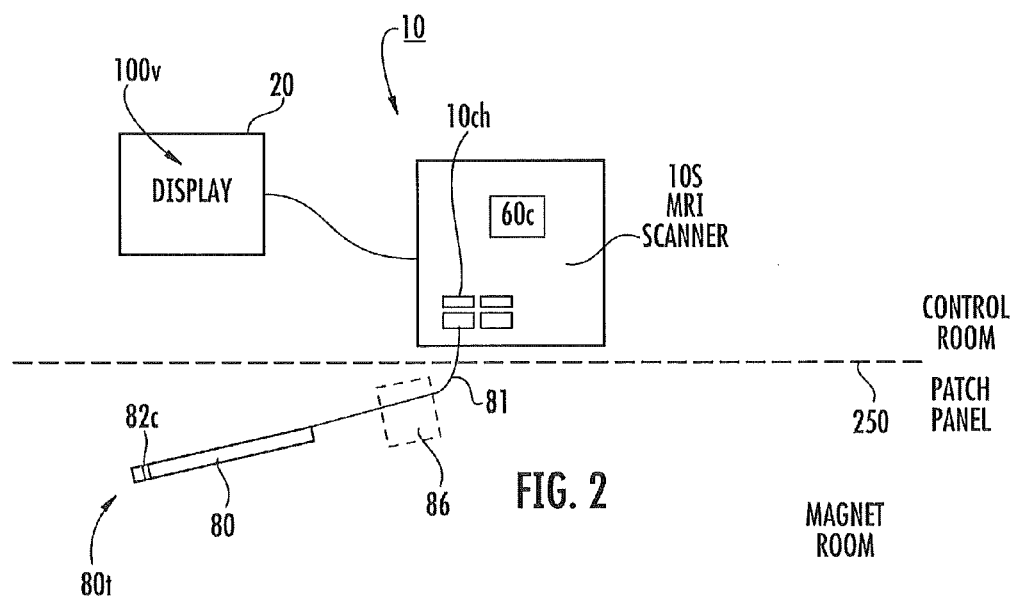
FIG. 2 is a schematic illustration of an intrabody device with a tracking coil electrically connected to a Scanner channel according to embodiments of the present invention.

The tracking members 82 can comprise miniature tracking coils, passive markers and/or a receive antenna. In a preferred embodiment, the tracking members 82 include at least one miniature tracking coil 82c that is connected to a channel 10ch of an MRI Scanner 10S (FIG. 2). The MR Scanner 10S can be configured to operate to interleave the data acquisition of the tracking coils 82c with the image data acquisition. The tracking data is typically acquired in a 'tracking sequence block' which takes about 10 msec (or less). In some embodiments, the tracking sequence block can be executed between each acquisition of image data (the latter can be referred to as an 'imaging sequence block'). So the tracking coil coordinates can be updated immediately before each image acquisition and at the same rate. As noted above, the tracking sequence can give the coordinates of all tracking coils simultaneously.

Embodiments of the present invention provide a new platform that can help facilitate clinical decisions during an MRI-guided procedure and can present real anatomical image data to the clinician in an interactive visualization 100v. The visualizations 100v (FIGS. 5A-5D) can be dynamically generated as the intrabody device 80 moves in the body into a target location, as a user rotates, crops or otherwise alters a displayed visualization or view and/or during an active therapy or diagnostic procedure step, e.g., while ablating at target lesion sites, with minimal latent time between serial MRI image data acquisitions, typically less than about 5 seconds, typically substantially continuously with a minimal latent time of about 1 second or less, such as between about 0.001 seconds and 1 second. Together, the system 10 can use the tracking signal(s) and image signal data to dynamically track the device 80 (which is typically a plurality of devices) and present visualizations of the anatomy and one or more intrabody devices 80 in near real-time.

The term "physical representation" means that a device is not actually imaged but rather rendered with a physical form in the visualizations. The physical representation may be of any form including, for example, a graphic with at least one geometric shape, icon and/or symbol. The physical representation can be in 3-dimensional form. In some particular embodiments, the physical representation may be a virtual graphic substantial replica substantially corresponding to an actual shape and configuration of the physical appearance and/or configuration of at least a portion (e.g., distal end portion) of the associated device (see, e.g., FIGS. 22A, 22B). The physical representation can be electronically generated based on a priori knowledge of the dimensions and configuration of the device 80. The tip and each tracking coil on a distal end of a particular device may be shown in a geometric shape (the same or different shapes, e.g., an arrow for the tip and a sphere or block or other (typically 3-D) shape for tracking coils, each in its real location in the 3-D space and in its relative position on the device and each may be rendered with the same or a different color. For example, the tip and each proximate tracking coil may be shown in a different color.

The term "tortuous" refers to a curvilinear pathway in the body, typically associated with a natural lumen such as vasculature. The term "dynamic visualizations" refers to a series of visualizations that show the movement of the device(s) in the body and can show a beating heart or movement based on respiratory cycle and the like.

The term "pre-acquired" means that the data used to generate the model or map of the actual patient anatomy was obtained prior to the start of an active therapeutic or diagnostic procedure and can include immediately prior to but during the same MRI session or at an earlier time than the procedure (typically days or weeks before).

Embodiments of the present invention can be configured to guide and/or place flexible intrabody diagnostic and/or interventional devices in an MRI environment (e.g., interventional medical suite) to any desired internal region of interest of a subject, typically via a natural lumen and/or tortuous path so that the intrabody devices can take on different non-linear configurations/shapes as it moves into position through a target pathway (which may be a natural lumen or cavity). The subjects can be animal and/or human subjects.

Some embodiments of the invention provide systems that can be used to facilitate ablation of tissue for treating cardiac arrhythmias, or to repair or replace cardiac valves, repair, flush or clean vasculature and/or place stents, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). The cardiac procedures can be carried out from an inside of the heart or from an outside of the heart. The system may also be suitable for delivering a therapeutic agent or carrying out another treatment or diagnostic evaluation for any intrabody location, including, for example, the brain, gastrointestinal system, genourinary system, spine (central canal, the subarachnoid space or other region), vasculature or other intrabody locations. Additional discussion of exemplary target regions can be found at the end of this document.

The system 10 and/or circuit 60c (FIGS. 2-3) can calculate the position of the tip of the device 80t as well as the shape and orientation of the flexible device based on a priori information on the dimensions and behavior of the device 80 (e.g., for a steerable device, the amount of curvature expected when a certain pull wire extension or retraction exists, distance to tip from different coils 82 and the like). Using the known information of the device 80 and because the tracking signals are spatially associated with the same X, Y, Z coordinate system as the MR image data, the circuit 60c can rapidly generate visualizations showing a physical representation of the location of a distal end portion of the device 80 with near RT MR images of the anatomy.

In some embodiments, the tracking signal data is obtained and the associated spatial coordinates are determined while a circuit 60c in the MRI Scanner 10S (FIG. 2) and/or in communication with the Scanner 10S (FIG. 3) obtains MR image data. The reverse operation can also be used. The circuit 60c can then rapidly render the resultant visualization(s) 100v (see, e.g., FIGS. 5A-5D) with the flexible device(s) 80 shown with a physical representation based on spatial coordinates of the devices in the 3-D imaging space identified using the associated tracking coil data and the near RT MR image(s).

Figure 3:
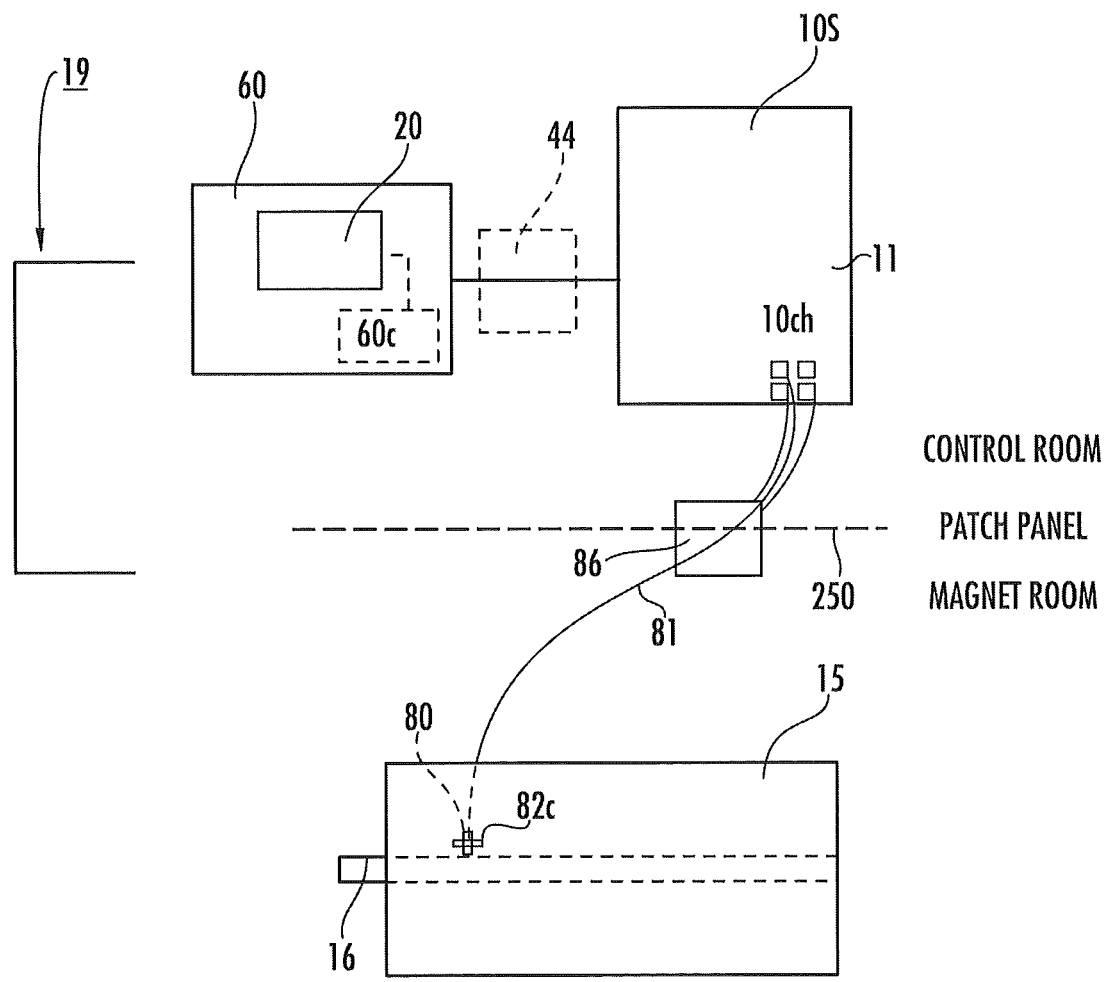
FIG. 3 is a schematic illustration of an MRI system with a workstation and display according to embodiments of the invention.

The circuit 60c can be totally integrated into the MR Scanner 10S (e.g., control cabinet), partially integrated into the MR Scanner 10S or be separate from the MR Scanner 10S but communicate therewith. If not totally integrated into the MR Scanner 10S, the circuit 60c may reside partially or totally in a workstation 60 and/or in remote or other local processor(s) and/or ASIC. FIG. 3 illustrates that a clinician workstation 60 can communicate with the MR Scanner 10S via an interface 44. Similarly, the device 80 in the magnet room can connect to the MR Scanner 10S via an interface box 86 which may optionally be integrated into the patch panel 250.

As shown in FIGS. 2 and 3, for example, the system 10 can include at least one (interactive) display 20 in communication with the circuit 60c and/or the Scanner 10S. The display 20 can be configured to display the interactive visualizations 100v. The visualizations 100v can be dynamic showing the movement of the device 80 relative to the intrabody anatomical structure shown by the displayed near-real time MRI image.

The system 10 can include a User Interface (UI) 25 with several UI controls 25c (FIG. 7), such as a graphic UI (GUI), in communication with the display 20 and may be configured to allow a user to select to show one or more pre-acquired or in situ generated maps and/or images 30 of target tissue including different tissue characterization maps and/or an optional EA map (or data from those maps) which can be shown in and/or with the visualization 100v. For example, the system 10 can be configured to allow a user to select to show a map of patient vasculature and/or fibrous tissue based on pre-acquired image data (such as segmented MRA (Magnetic Resonance Angiography or other image slices) with the map or data therefrom being registered to and overlaid onto or incorporated into at least one of the models 100M in the visualization and can be selectively turned on and off by a user. This information may help a clinician select a treatment site or avoid a treatment site or otherwise affect clinical choices. For example, for cardiac use, if vasculature with a relatively large blood flow is shown in a target lesion space in cardiac tissue and/or if fibrous tissue is shown, a clinician may choose another spot or may ablate longer to form a transmural lesion. Further examples of display options will be discussed further below.

In some embodiments, the system/circuit can employ interactive application of non-selective saturation to show the presence of a contrast agent in near real-time scanning. This option can help, for example, during image-guided catheter navigation to target tissue that borders scar regions. See, e.g., Dick et al., *Real Time MRI enables targeted injection of labeled stem cells to the border of recent porcine myocardial infarction based on functional and tissue characteristics*, Proc. Intl. Soc. Mag. Reson. Med. 11, p. 365 (2003); Guttman et al., *Imaging of Myocardial Infarction for Diagnosis and*

*Intervention Using Real-Time Interactive MRI Without ECG-Gating or Breath-Holding*, Mag. Reson. Med, 52: 354-361 (2004), and Dick and Guttman et al., *Magnetic Resonance Fluoroscopy Allows Targeted Delivery of Mesenchymal Stem Cells to Infarct Borders in Swine*, Circulation, 2003; 108: 2899-2904, which describe, inter alia, imaging techniques used to show regions of delayed enhancement in (near) real-time scans. The contents of these documents are hereby incorporated by reference as if recited in full herein.

FIG. 2 illustrates that the device 80 can include at least one conductor 81, such as a coaxial cable that connects a respective tracking coil 82c to a channel 10ch of the MR Scanner 10S. The MR Scanner 10S can include at least 16 separate channels, and typically more channels but may operate with less as well. Each device 80 can include between about 1-10 tracking coils, typically between about 1-4. The coils 82c on a particular device 80 can be arranged with different numbers of turns, different dimensional spacing between adjacent coils 82c (where more than one coil is used) and/or other configurations. The circuit 60c can be configured to generate the device renderings based on tracking coil locations/positions relative to one another on a known device with a known shape and/or geometry or predictable or known changeable (deflectable) shape or form (e.g., deflectable end portion). The circuit can identify or calculate the actual shape and orientation of the device for the renderings based on data from a CAD (computer aided design) model of the physical device. The circuit can include data regarding known or predictable shape behavior based on forces applied to the device by the body or by internal or external components and/or based on the positions of the different tracking coils in 3-D image space and known relative (dimensional) spacings.

As shown in FIG. 3, the display 20 can be provided in or associated with a clinician workstation 60 in communication with an MRI Scanner 10S. Other displays may be provided. The MRI Scanner 10S typically includes a magnet 15 in a shielded room and a control cabinet 11 (and other components) in a control room in communication with electronics in the magnet room. The MRI Scanner 10S can be any MRI Scanner as is well known to those of skill in the art.

Figure 4:
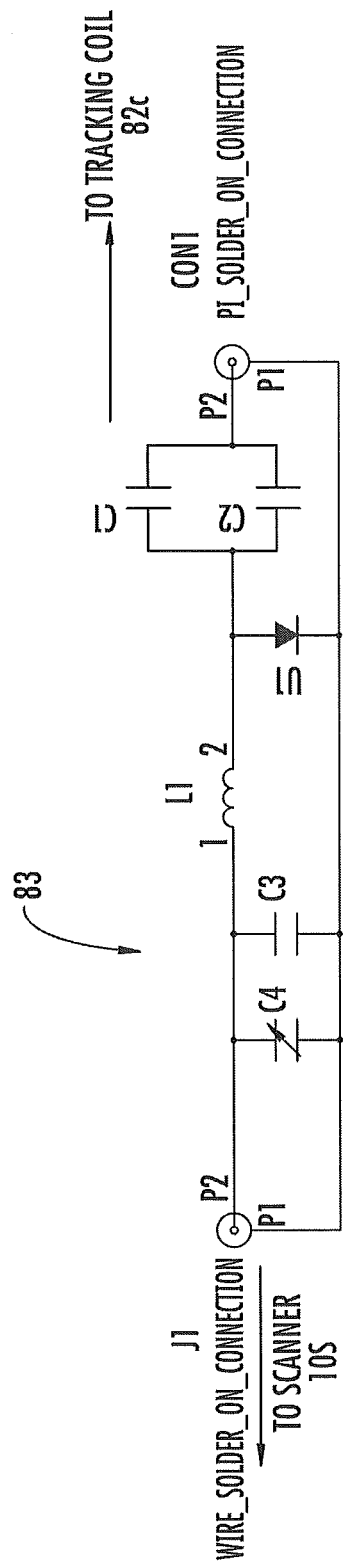
FIG. 4 is a circuit diagram of an exemplary tracking coil tuning circuit according to embodiments of the present invention.

The tracking coils 82c can each include a tuning circuit that can help stabilize the tracking signal for faster system identification of spatial coordinates. FIG. 4 illustrates an example of a tuning circuit 83 that may be particularly suitable for a tracking coil 82c. As shown, CON1 connects the coaxial cable 81 to the tracking coil 82c on a distal end portion of the device 80 while J1 connects to the MR Scanner channel 10ch. The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10ch. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle (e.g., 440, FIG. 31) or other external portion), in a connector that connects the coil 82c to the respective MRI scanner channel 10ch, in the Scanner 10S, in an interface box 86 (FIG. 2), a patch panel 250 and/or the circuit 83 can be distributed among two or more of these or other components.

In some embodiments, each tracking coil 82c can be connected to a coaxial cable 81 having a length to the diode via a proximal circuit board (which can hold the tuning circuit and/or a decoupling/matching circuit) sufficient to define a defined odd harmonic/multiple of a quarter wavelength at the operational frequency of the MRI Scanner 10S, e.g., $\lambda/4$, $3\lambda/4$, $5\lambda/4$, $7\lambda/4$ at about 123.3 MHz for a 3.0 T MRI Scanner. This length may also help stabilize the tracking signal for more precise and speedy localization. The tuned RF coils can provide stable tracking signals for precise localization, typically within about 1 mm or less. Where a plurality (e.g., two closely spaced) of adjacent tracking coils are fixed on a substantially rigid material, the tuned RF tracking coils can provide a substantially constant spatial difference with respect to the corresponding tracking position signals.

The tracking sequence used in the system 10 can intentionally dephase signal perpendicular to the read-out direction to attenuate unwanted signal from 1) bulk objects and 2) regions sensed by other signal sensitive parts of the catheter which couple to the tracking coil (e.g. the coaxial cable along the catheter shaft). This tends to leave only a sharp peak indicating the position of the tracking coil.

The tracking sequence block can include or consist of a plurality of (typically about three) repetitions of a small flip-angle excitation. Each repetition is designed to indicate the x, y or z component of the tracking coil coordinates in succession. Frequency encoding is used along the x-direction to obtain the x-coordinate, the y-direction for the y-coordinate, and the z-direction for the z-coordinate. When the frequency encoding is in the x-direction, the other two directions (y and z) are not spatially encoded, producing projection (spatially integrated) signals in those directions from all excitation regions. The dephasing gradient attempts to attenuate unwanted signal included in these projections. Once the tracking sequence block is complete, a spoiler gradient can be used to dephase any transverse signal remaining from the tracking before the imaging sequence block is executed.

The imaging sequence block obtains a portion, depending on the acceleration rate, of the data used to reconstruct an image of a single slice. If the acceleration rate is 1, then all of the data for an image is collected. If the acceleration rate is 2, then half is collected, etc. If multiple slices are activated, then each successive imaging block collects data for the next slice, in 'round robin' fashion. If any magnetization preparation (e.g., saturation pulses) is activated, these are executed after the tracking sequence block, immediately before the imaging sequence block.

Additional discussion of tracking means and ablation catheters can be found in U.S. Pat. No. 6,701,176, and U.S. Provisional Application Ser. No. 61/261,103, the contents of which are hereby incorporated by reference as if recited in full herein. Exemplary catheters will be discussed further below.

Referring now to FIGS. 5A-5D and 6, examples of visualizations 100v with a physical representation 80R of the intrabody device 80, a volumetric model 100M of target anatomical structure and a near real-time MRI image 100MRI. The circuit 60c/Scanner 10S is configured to present a 3-D volumetric model of at least a portion of the patient's target anatomy (shown as the heart) 100M in the visualization 100v with the model registered to the 3-D imaging space along with a physical representation of at least the distal end portion of the at least one intrabody device 80R in the imaging space. Optionally, the visualizations can be carried out to show the tracking coils in the physical representation of the distal end portion of the medical device in different colors using the identified location of the tracking coils and defined form factor and/or dimensional data regarding actual coil placement on the device.

The circuit 60c can be configured to generate the visualizations 100v with at least two visual reference planes 41, 42 (shown with a third intersecting plane 43) that are typically oblique or orthogonal to each other and extend through at least a major portion of the visualization 100v. The planes 41, 42 (and 43) can be transparent and/or translucent. They may be shown with different color perimeters that correspond to a respective two-dimensional image slice (which may be shown as thumbnails on the display also with a perimeter of similar or the same color).

The planes 41, 42 can move relative to each other in the imaging space or may be locked together, in any case they can be configured to move relative to the model 100M in the imaging space. As shown in FIGS. 5A-5D, a user can rotate and zoom the visualization 100v which automatically adjusts the visualization shown on the display. As also shown, the flexible device 80 is not required to be in any of the relevant anatomical scan planes used to obtain MR data for the at least one near RT MRI image 100MRI in the visualization and the distal end portion 80d of the flexible device 80 can take on a curvilinear shape and the tip 80t can be steered or guided into different target positions.

Figure 5A:
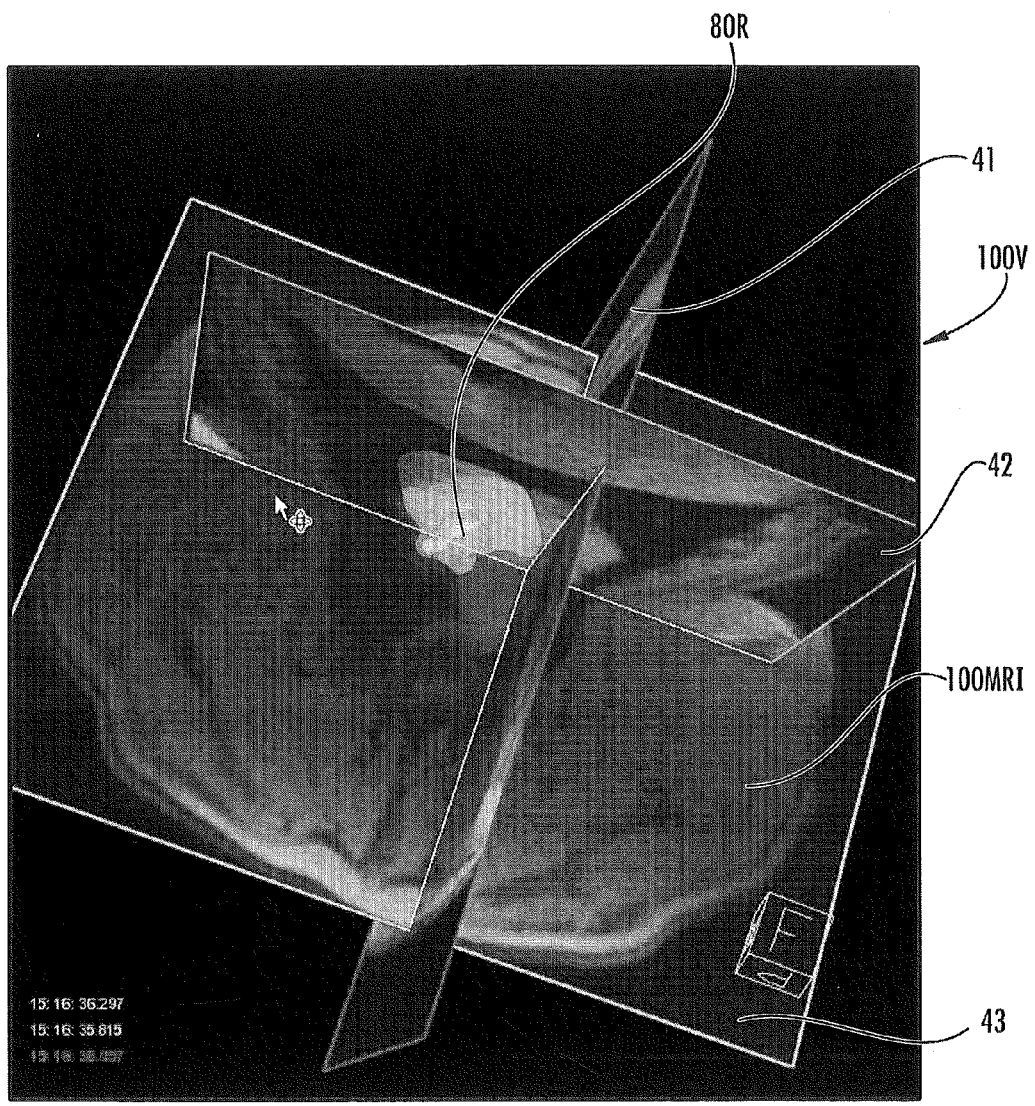
FIGS. 5A-5D are contemplated screen shots of exemplary interactive visualizations with a physical representation of an intrabody flexible medical device according to embodiments of the present invention.
Figure 5B:
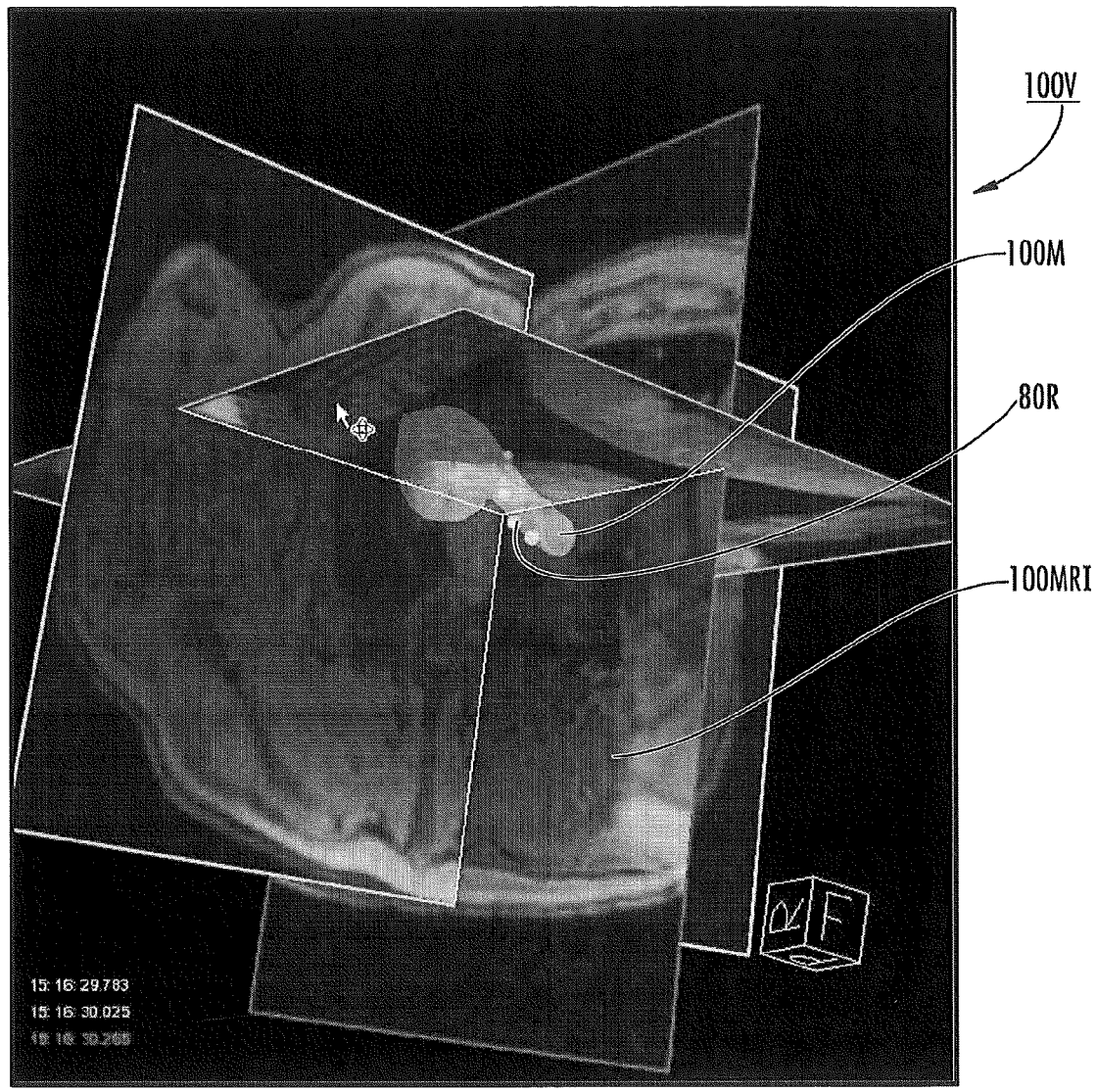
Figure 5C:
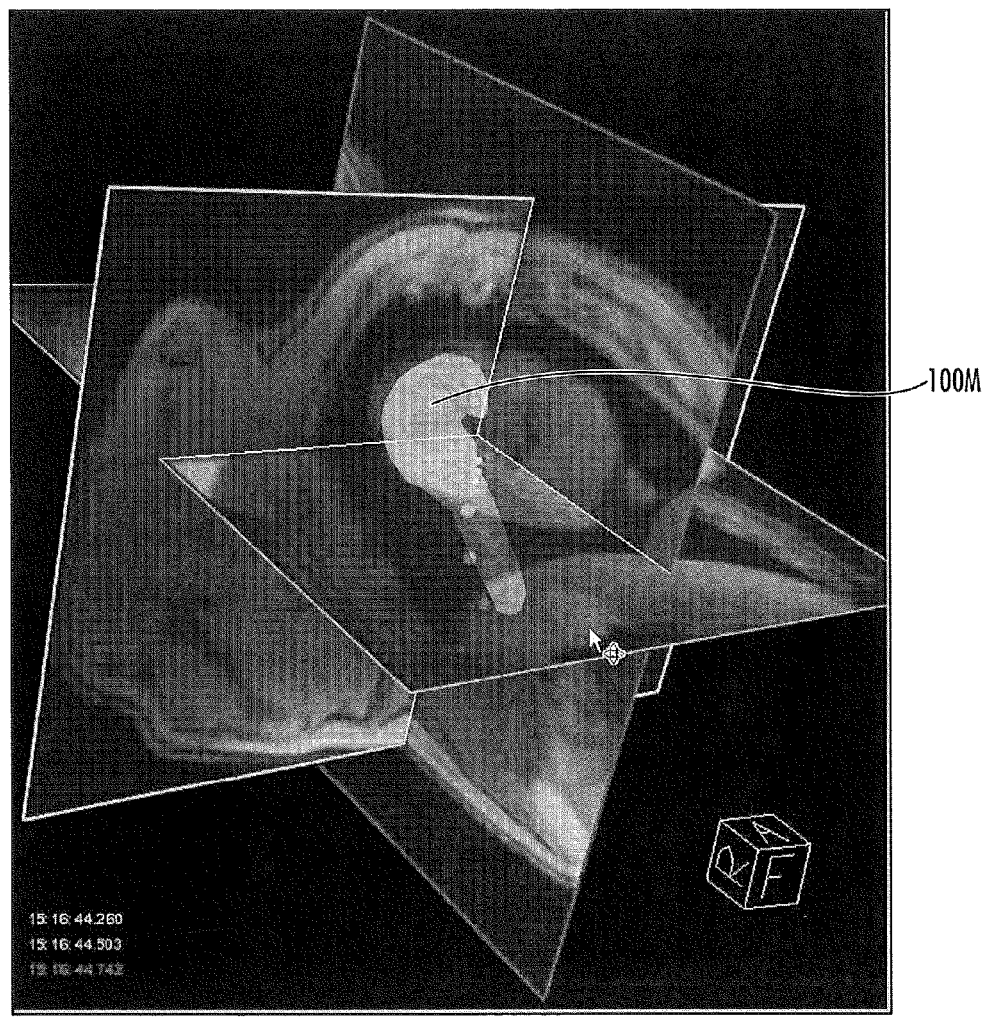
Figure 5D:
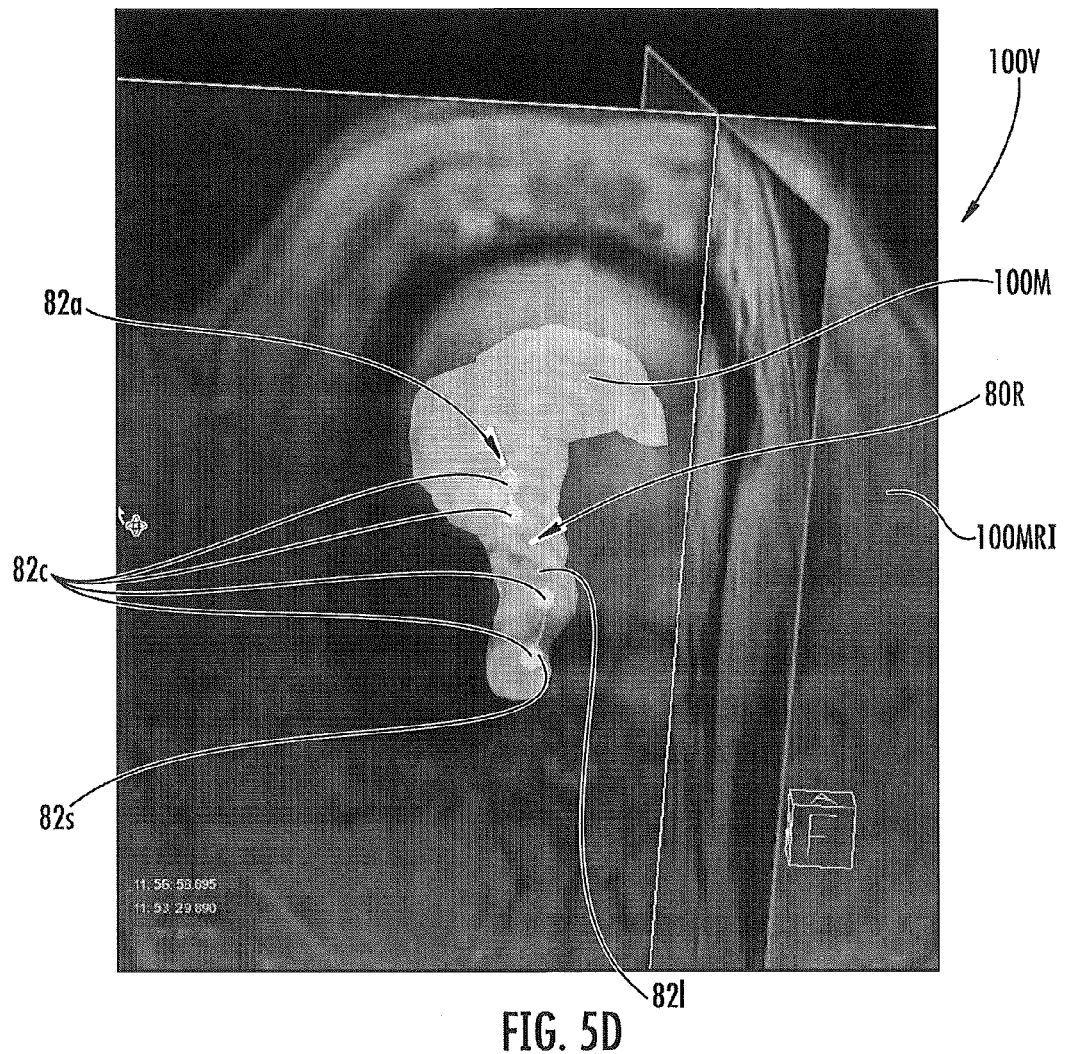

In some embodiments, as shown in FIG. 5D, the circuit 60c is configured to associate a tip location of the at least one device 80 with an arrow 82a or other visual feature and render the visualization so that each tracking coil 82 on the distal end portion 80d has a shape 82s with a color, with each tracking coil 82 having a respective different color from the other tracking coils, and with a line or spline 82l connecting the tip 82a and the coils 82c and the line 82l is able to flex, bend and move to reflect movement of the device 80 in the visualizations 100v. The system/circuit can be configured to display color-highlighted images generated using tracking coil data from the MR Scanner tracking coil channels so as to display the coils as color high-lighted features in the 3D rendering of the physical representation of the device (e.g., catheter).

Figure 6:
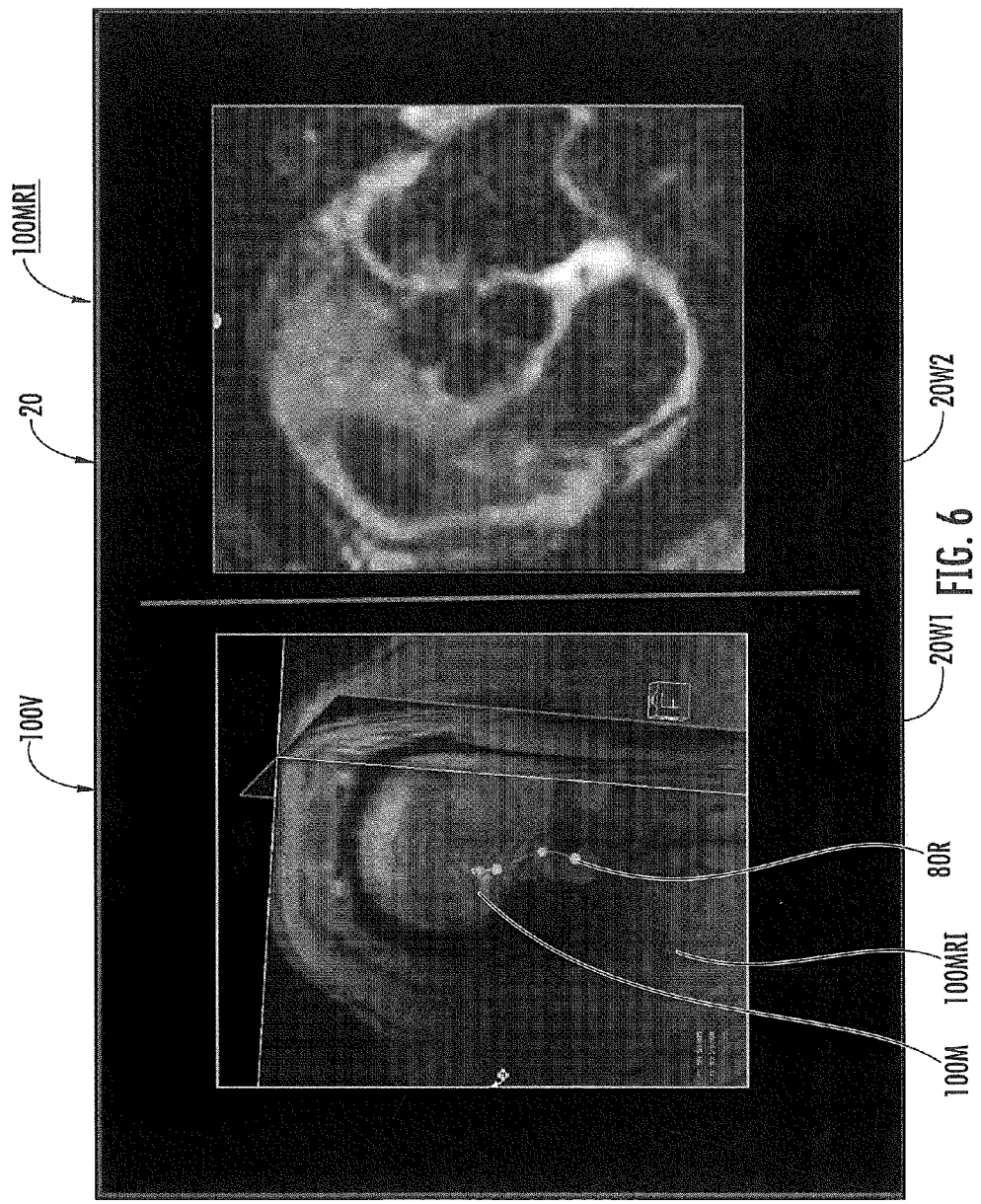
FIG. 6 is a schematic illustration of a display with two viewing windows, one showing an interactive visualization and the other showing at least one relevant near RT MRI image according to embodiments of the present invention.

FIG. 6 illustrates that the system 10 can be configured to show both the interactive visualization 100v in one viewing window 20w₁ and an MRI image 100MRI alone in a second viewing window 20w₂. The MRI image 100MRI in the second window 20w₂ is typically associated with the target anatomy location (identified by a user) in the interactive visualization 100v in the first viewing window 20w₁.

Figure 7:
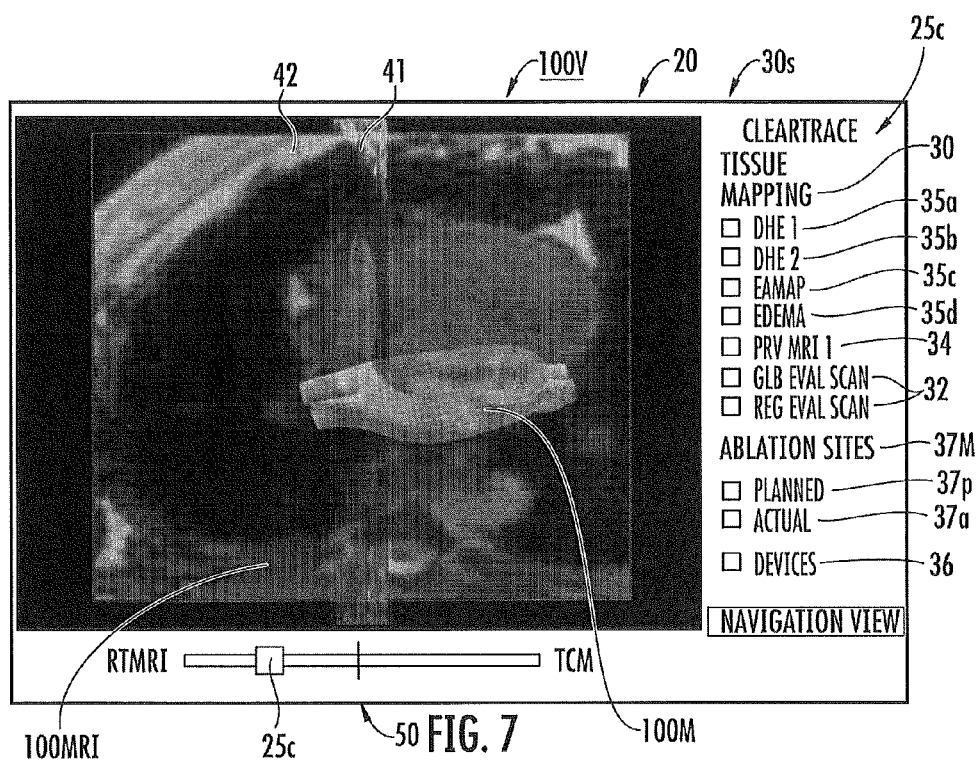
FIGS. 7-21 are contemplated screen shots of exemplary visualizations and images on a display and UI controls that can be generated to facilitate an MRI guided procedure according to embodiments of the present invention.

As shown in FIG. 7, the display 20 can have a UI 25 with at least one UI control 25c configured to allow a physician or other clinician to select whether to show near real time MR images of target tissue 100MRI either with a model 100M of the target anatomical structure (FIG. 7) and/or in a separate viewing window (FIGS. 6, 13-16). The circuit 60 is in communication with at least one display 20 with the UI 25.

Figure 9:
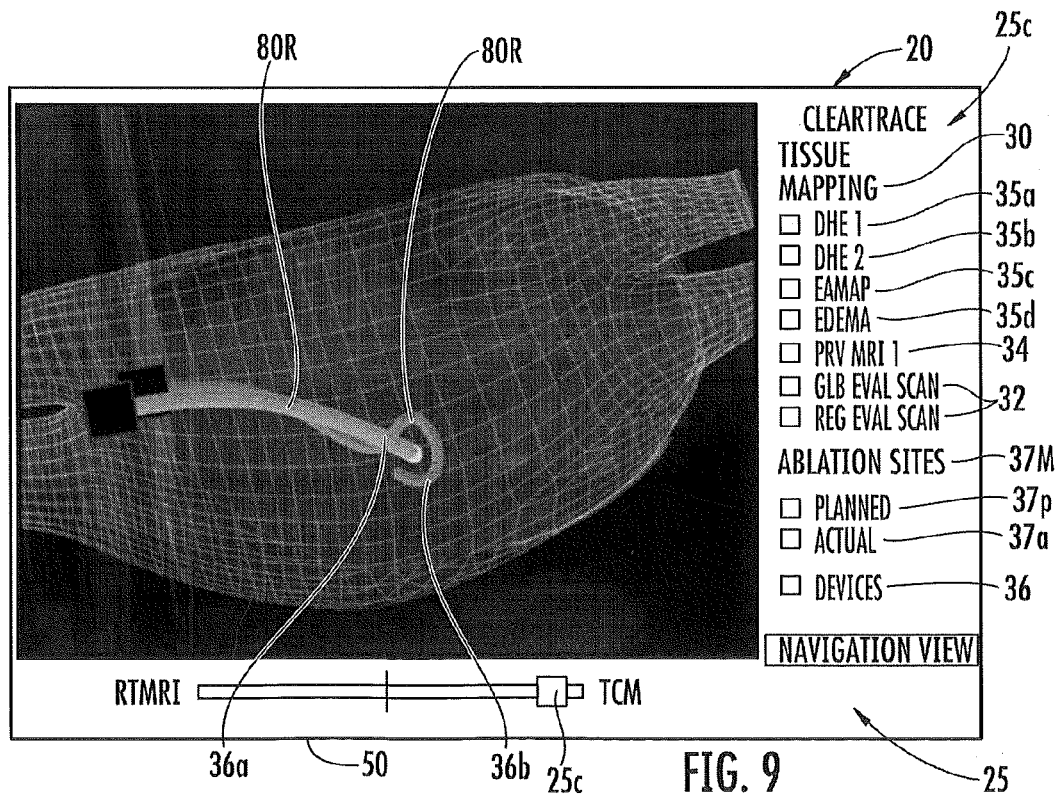

The UI 25 can be configured to allow a user to alter the displayed visualization (fade) to include only a near RT image of the anatomy, to include the near RT image of the anatomy and the registered model of the heart, or to include only the registered model, see, for example, FIG. 7 showing both types of images in the visualization 100v with FIG. 9 which shows only the model 100M. The UI 25 can be an on off selection of these options or may "fade" from one viewing option to another. As shown, a virtual sliding control 25c allows a user to change what is shown ((near) RTMRI 100MRI to only the Model 100M).

The circuit 60c can also be configured to generate images showing the device location in MR image space. The UI 25 can also be configured to allow a user to fade the renderings of the device 80 in and out of the visualizations with actual images of the device and tracking coils to confirm location or for additional visual input. The device may include other fiducial markers (e.g., a passive marker or an active marker such as receive antenna) for facilitating the visual recognition in the MR image.

The UI 25 typically includes multiple GUI controls 25c that can include a touch screen input control to allow a clinician/physician to select a region of interest in the map 100M by placing a cursor or by touching the screen at a region of interest. This can cause the system to obtain real time MR image data of that region and provide the associated image on the display and/or define scan planes (which may be preset scan planes) at that location in space.

Referring again to FIG. 7, for example, the display 20 can be in communication with a UI 25 that provides a plurality of user selectable different maps 30 so that the map or data therefrom can be "turned on and off" on the displayed 3-D anatomical map registered to the imaging space. The different maps can comprise a patient-specific 3-D (volumetric) anatomical map, and/or data that can be shown on the 3-D anatomical map, registered to the imaging space. For tissue characterization maps, the maps include spatially correlated tissue characterization data taken from MR image data incorporated therein as discussed above. The UI 25 can include multiple different GUI controls 25c for different functions and/or actions. The GUI controls 25c may also be a toggle, a touch screen with direction sensitivity to pull in one direction or other graphic or physical inputs.

Figure 10:
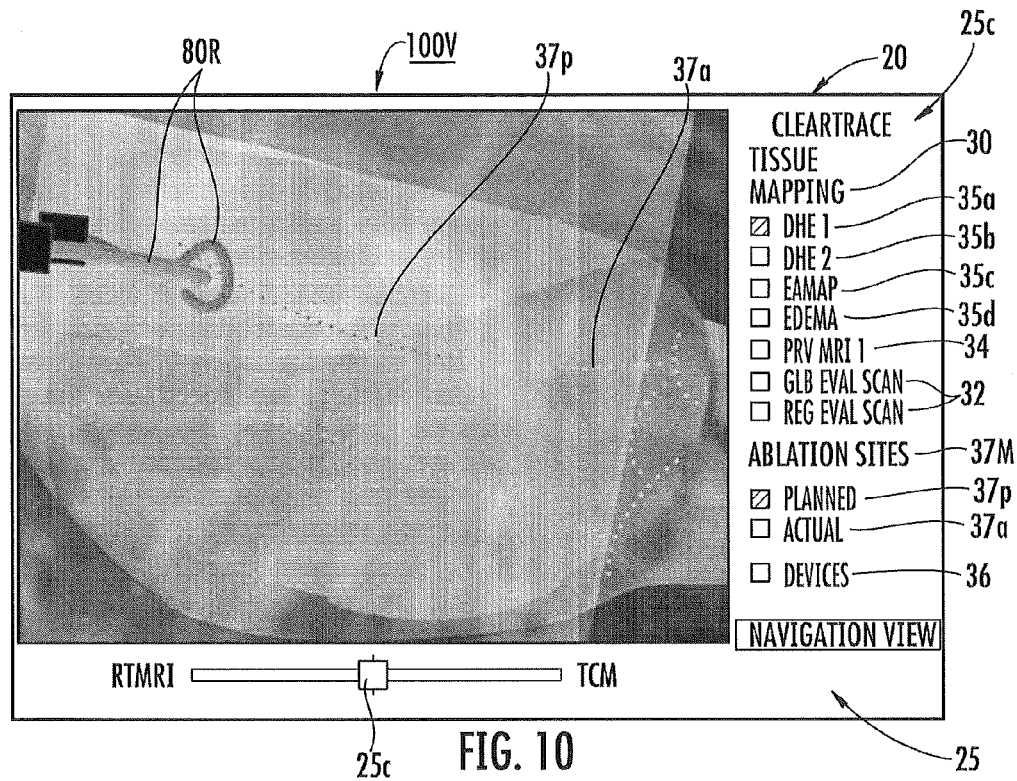
Figure 11:
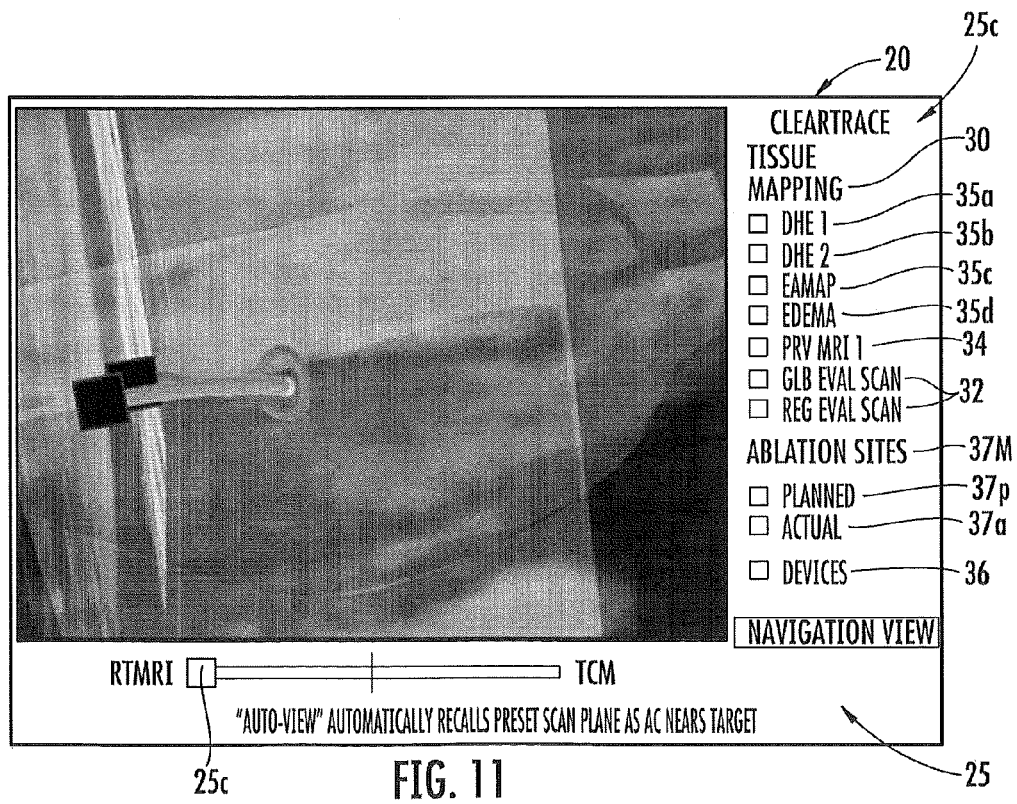
Figure 17:
Figure 19:
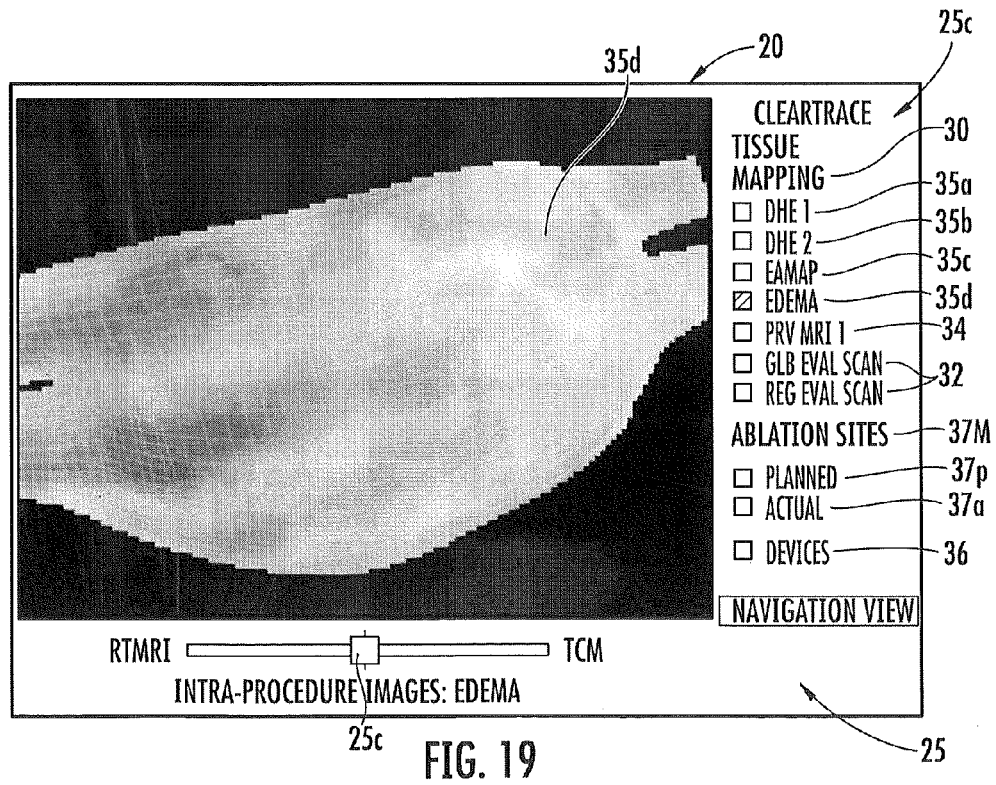
Figure 27:
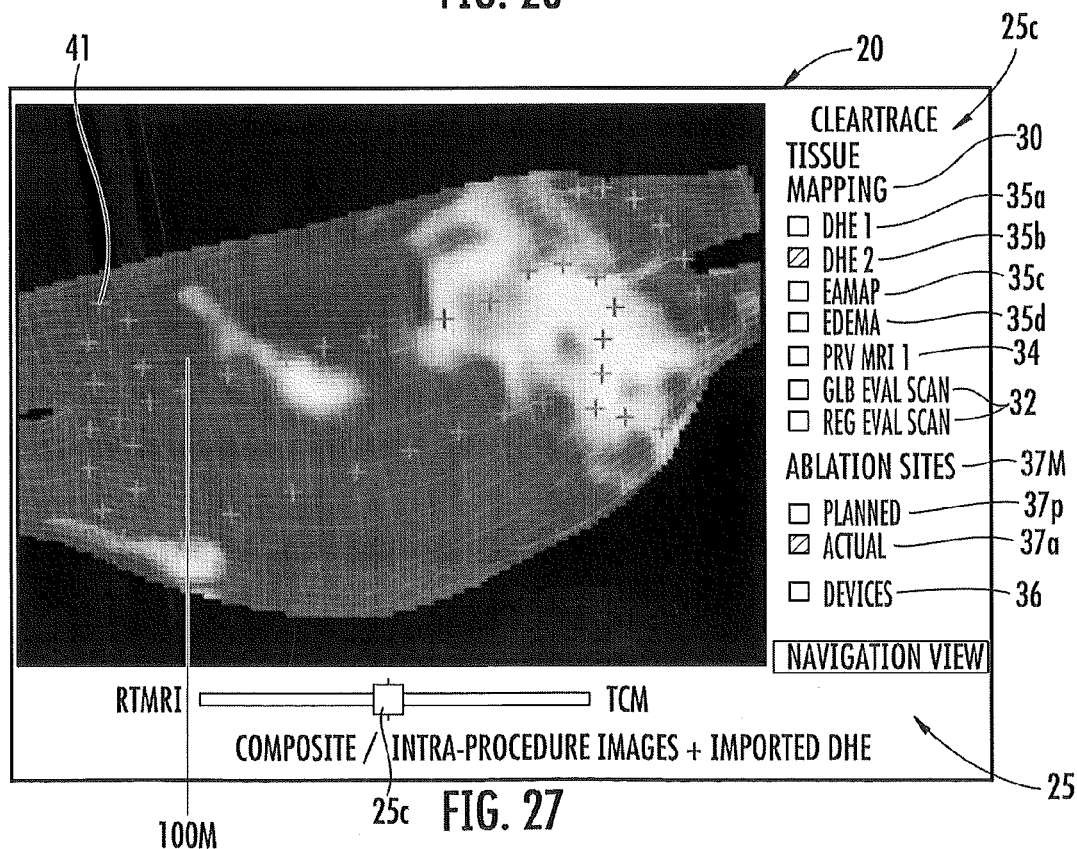
Figure 28:
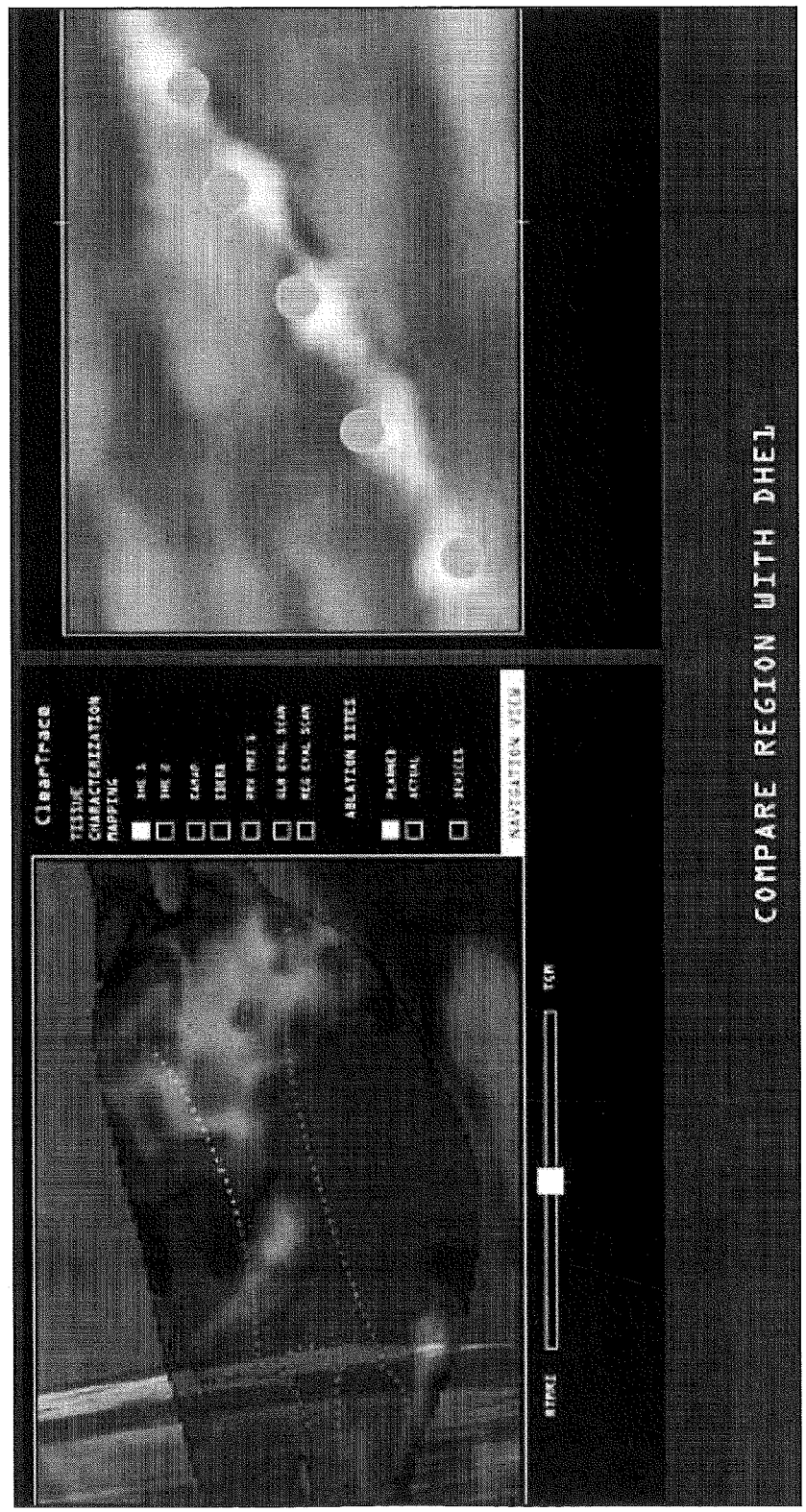

The user selectable patient-specific maps 30 including a plurality of tissue maps, typically including at least one, and more typically several types of, tissue characterization maps (or data associated with such maps to be shown on a registered model) associated with the procedure that can be selected for viewing by a user. The UI 25 can also include GUI controls that allow a user to select two or more of the tissue characteristic maps, with such data able to be shown together (overlaid and registered and/or as a composite image/map) or separately. As shown, the maps 30 and/or data therefrom, may include at least a plurality of the following user selectable data:

(a) a regional evaluation scan map 32r (FIG. 17) and/or a global evaluation scan map 32g (FIG. 13) which shows tissue information, e.g., actual lesion patterns in one region to allow a clinician to view regional ablation information (such as at the LA (left atrium), a PV (pulmonary vein) and the like);

(b) pre-procedure MRI cardiac scans 34 (FIG. 7);

(c) DHE 1 (Delayed Hyper Enhancement) tissue characterization map 35a taken at a first point in time (such as a week or just prior to the procedure) (FIG. 28);

(d) DHE 2 tissue characterization map 35b taken at a second point in time, such as during a procedure, potentially toward an end of the procedure (for cardiac ablation procedures that can be used to confirm complete electrical isolation of the PV (pulmonary veins) or other targets prior to terminating the procedure—alternatively the DHE 2 map can be associated with the end of a prior EP ablation procedure) (FIG. 27);

(e) an EA (electroanatomical) map 35c (FIG. 17);

(f) an edema tissue characterization map 35d (FIG. 19);

(g) other tissue characterization maps 35e, for example:

(i) a composite thermal tissue characterization map that shows positions of increased temperature that were caused by ablation of tissue during the procedure;

(ii) ischemic (oxygen deprived or lacking) tissue characterization map;

(iii) hypoxic or necrotic tissue characterization map;

(iv) fibrous tissue map;
(v) vasculature map;
(vi) cancer cell/tissue map (where cancer is the condition being treated);

(h) at least one procedure planning map 37M with target sites 37p (also referred to interchangeably herein as sites 55t) and a later tissue map showing actual sites 37a (e.g., target and actual ablation sites) shown in different colors, opacities and/or intensities for ease of reference (see, e.g., FIG. 10, red/darker spots associated with target and green or lighter spots associated with actual); and (i) device views 36 that show the physical representation of the device 80 in the surgical/imaging space, e.g., with an ablation catheter 36a shown in position and/or a mapping (loop) catheter 36b as devices 80 shown in position (FIGS. 9, 11). These device maps 36 may be used/displayed, for example, during a navigation mode. The default action may be to show these devices at least in the navigation mode but a user can deselect this choice.

The tissue maps 30 (or tissue characterization data) are typically registered to the 3-D coordinate image space (manually or via automatic electronic image alignment registration means). In some embodiments, relevant image scan planes and MR image data of the patient can be imported and/or incorporated into one or more of the tissue characterization maps so that the map(s) can be updated over time (including in real time) using MR image data correlated with the anatomical location on the tissue characterization map and shown on the (updated) tissue characterization map 30 automatically or upon request by a user. EA maps can be generated using tracking and/or mapping catheters in MRI images space which may provide a more accurate or timely EA map.

The tissue map(s) 30 can be generated using MR image data that shows normal and abnormal status, conditions and/or behavior of tissue. For example, the tissue characterization map(s) can show a thermal profile in different colors (or gray scale) of cardiac tissue in a region of interest and/or globally. In other embodiments, the tissue characterization map can illustrate one or more of infarct tissue, other injured tissue such as necrotic or scar tissue, hypoxic, ischemic, edemic (e.g., having edema) and/or fibrotic tissue or otherwise impaired, degraded or abnormal tissue as well as normal tissue on an anatomical model of the heart. In yet other embodiments, the tissue characterization map can illustrate portions of the heart (e.g., LA or posterior wall) with lesser or greater wall motion, and the like.

Whether a parameter or tissue characteristic is shown in a respective tissue characterization map 30 as being impaired, degraded or otherwise abnormal versus normal can be based on the intensity of pixels of the tissue characteristic in the patient itself or based on predefined values or ranges of values associated with a population "norm" of typical normal and/or abnormal values, or combinations of the above.

Thus, for example, normal wall motion can be identified based on, a comparison to defined population norms and different deviations from that normal wall motion can be shown as severe, moderate or minimal in different colors relative to tissue with normal wall motion.

In another example, a thermal tissue characterization map 30 can illustrate tissue having increased temperatures relative to other adjacent or non-adjacent tissue. Thus, for example, during or shortly after ablation, the lesioned tissue and tissue proximate thereto can have increased temperatures relative to the non-lesioned temperature or tissue at normal body temperatures. Areas or volumes with increased intensity and/or intensity levels above a defined level can be identified as tissue that has been ablated. The different ablation sites 55t can be shown on the map 30 as areas with increased temperatures (obtained at different times during the procedure) and incorporated into the thermal tissue characterization map 30 automatically and/or shown upon request.

In some embodiments, the tissue characteristic map 30 uses MR image data acquired in association with the uptake and retention of a (e.g., T-1 shortening) contrast agent. Typically, a longer retention in tissue is associated with unhealthy tissue (such as infarct tissue, necrotic tissue, scarred tissue and the like) and is visually detectable by a difference in image intensity in the MR image data, e.g., using a T1 weighted sequence, to show the difference in retention of one or more contrast agents. This is referred to as delayed enhancement (DE), delayed hyper-enhancement (DHE) or late gadolinium enhancement (LGE). As discussed above, in some embodiments, the system/circuit can employ interactive application of non-selective saturation to show the presence of a contrast agent in near real-time scanning. This option can help, for example, during image-guided catheter navigation to target tissue that borders scar regions. Thus, the DHE image data in a DHE tissue characterization map can be pre-acquired and/or may include near-RT image data.

The tissue map is typically a volumetric, 3-D or 4-D anatomical map that illustrates or shows tissue characterization properties associated with the volume as discussed above. The map can be in color and color-coded to provide an easy to understand map or image with different tissue characterizations shown in different colors and/or with different degrees of a particular characterization shown in gray scale or color coded. The term "color-coded" means that certain features or conditions are shown with colors of different color, hue or opacity and/or intensity to visually accentuate different conditions or status of tissue or different and similar tissue, such as, for example to show lesions in tissue versus normal or non-lesion tissue.

In some embodiments, the UI 25 can be configured to allow a clinician to increase or decrease the intensity or change a color of certain tissue characterization types, e.g., to show lesion tissue or tissue having edema with a different viewing parameter, e.g., in high-contrast color and/or intensity, darker opacity or the like. A treatment site, such as a lesion site(s) in/on the tissue characterization map 30 can be defined based on a position in three-dimensional space (e.g., where an electrode is located based on location detectors, such as tracking coils, when the ablation electrode is activated to ablate), but is typically also or alternately associated with MRI image data in associated scan planes to show an ablation site(s) in an MRI image. The MR image data may also reflect a change in a tissue property after or during ablation during the procedure, e.g., DHE, thermal, edema and the like.

The circuit 60c can be configured to generate a tissue map 37M (FIG. 27) that is a difference or a comparison map that is generated from a pre-procedure or start-of procedure tissue data and an intra-procedure tissue data to show the differences based on the procedure. The "before" and "after" maps can be electronically overlaid on a display and shown in different colors, opacities and/or intensities or corresponding pixel values from each image in a region of interest (ROI) can be subtracted to show a difference map or otherwise integrated into a composite map. Again, the UI 25 can allow a clinician to select or deselect (or toggle between) the before or after tissue characterization maps or adjust display preferences to allow a visual review of differences.

A regional update tissue map 32 can be used to evaluate whether target or actual treatment sites have been successfully treated, e.g., whether ablated locations have the desired transmural lesion formation. For example, the UI 25 can allow the clinician to select a high resolution or enlarged view of the actual ablated tissue merely by indicating on the interactive map 100M, such as a regional evaluation tissue map, a desired region of interest (e.g., by pointing a finger, cursor or otherwise selecting a spot on the display). For example, a high resolution MR image of suspect tissue in the LSPV can be shown so that the physician can see actual tissue in the desired spot indicated on the tissue characterization map. New targets can be electronically marked on the map as needed and scan planes can be automatically electronically be selected, identified or otherwise associated with the new target location.

Figure 13:
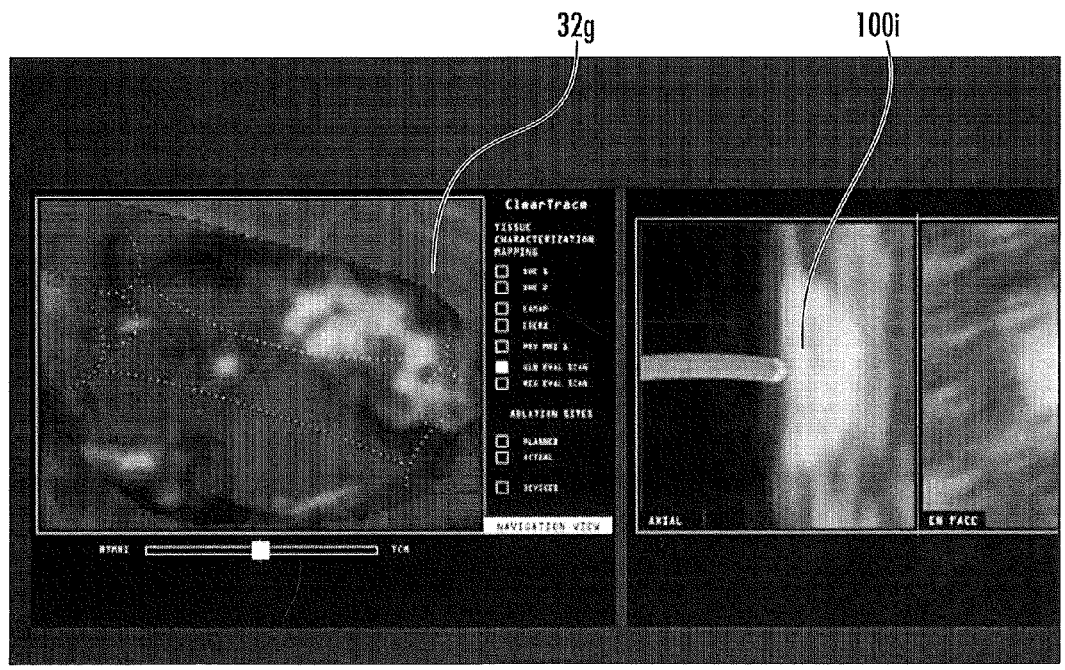

FIG. 13 shows the display 20 with side-by-side viewing windows, one window showing the visualization with the map 100M (which may be a tissue characterization map) and the other window with at least one near RT MRI image of local tissue during an active treatment mode.

Figure 22A:
FIGS. 22A and 22B are exemplary (contemplated) screen shots of an intrabody device (e.g., ablation catheter) with the device rendered as a physical representation and the MRI image being in close-up according to embodiments of the present invention.
Figure 22B:
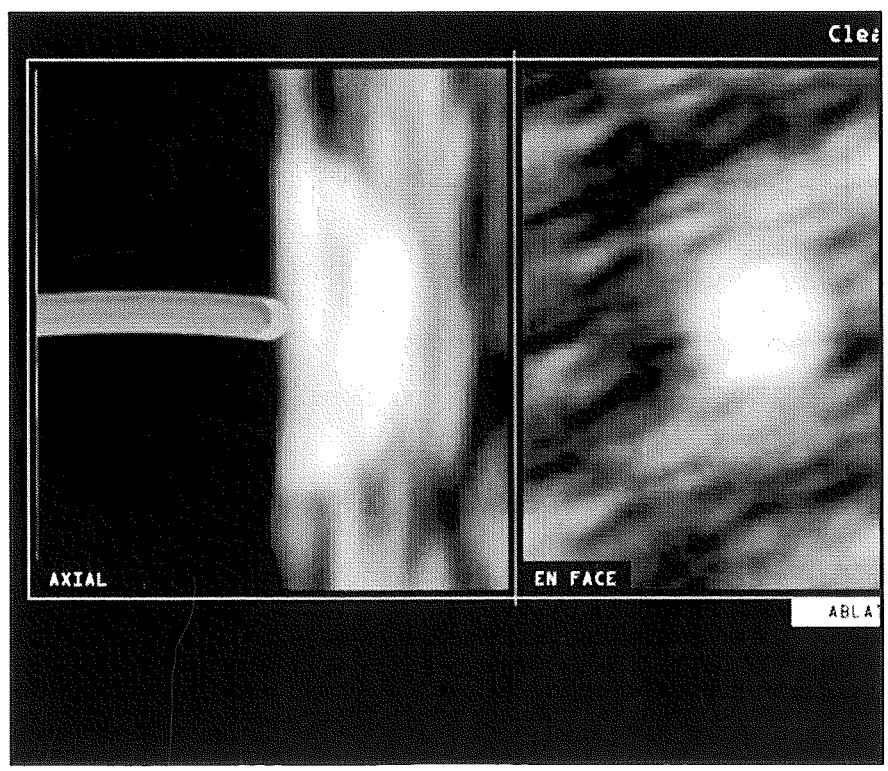

FIGS. 22A and 22B illustrate two windows of the axial and en face views of local tissue. FIG. 22A shows the tissue prior to ablation and FIG. 22B shows the tissue during or after an ablation. For example, during an ablation mode the system can use a default viewing rule to display the near real time MR image data of the affected tissue during the treatment, e.g., ablation, typically showing both en face and side views of the local tissue and treatment (ablation tip) according to embodiments of the present invention. In certain embodiments, the interactive visualization map 100v and/or model 100M may not be displayed during all or some of the ablation.

Figure 8:
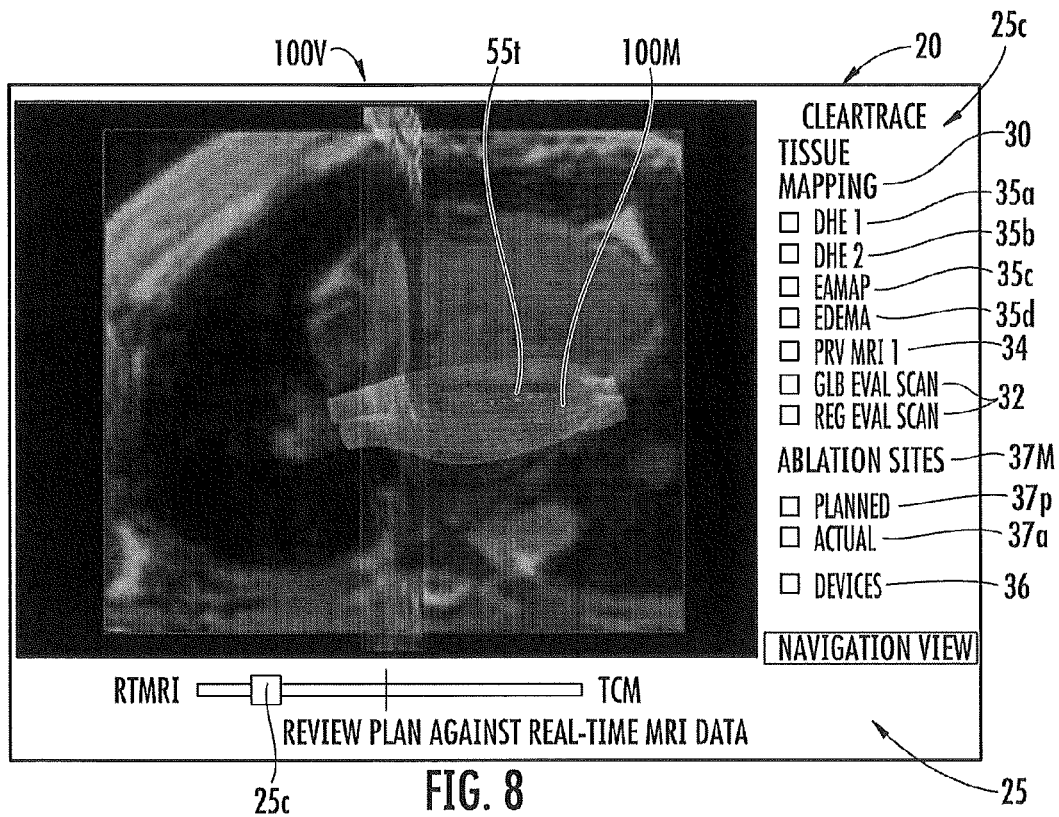
Figure 12:
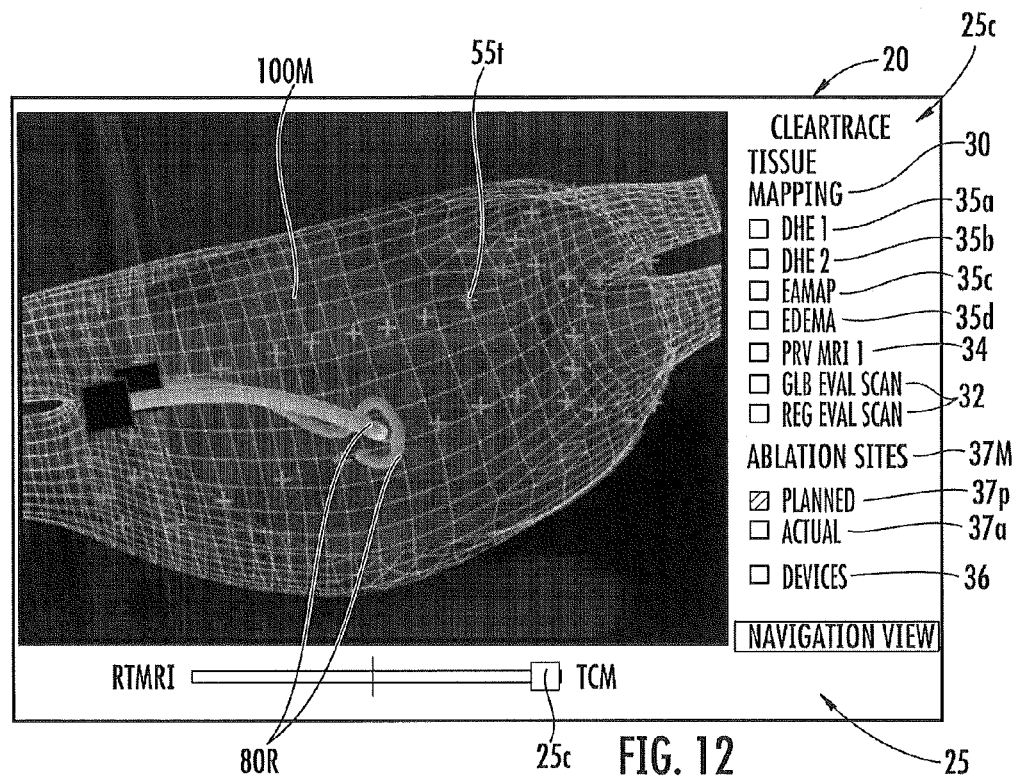
Figure 25:
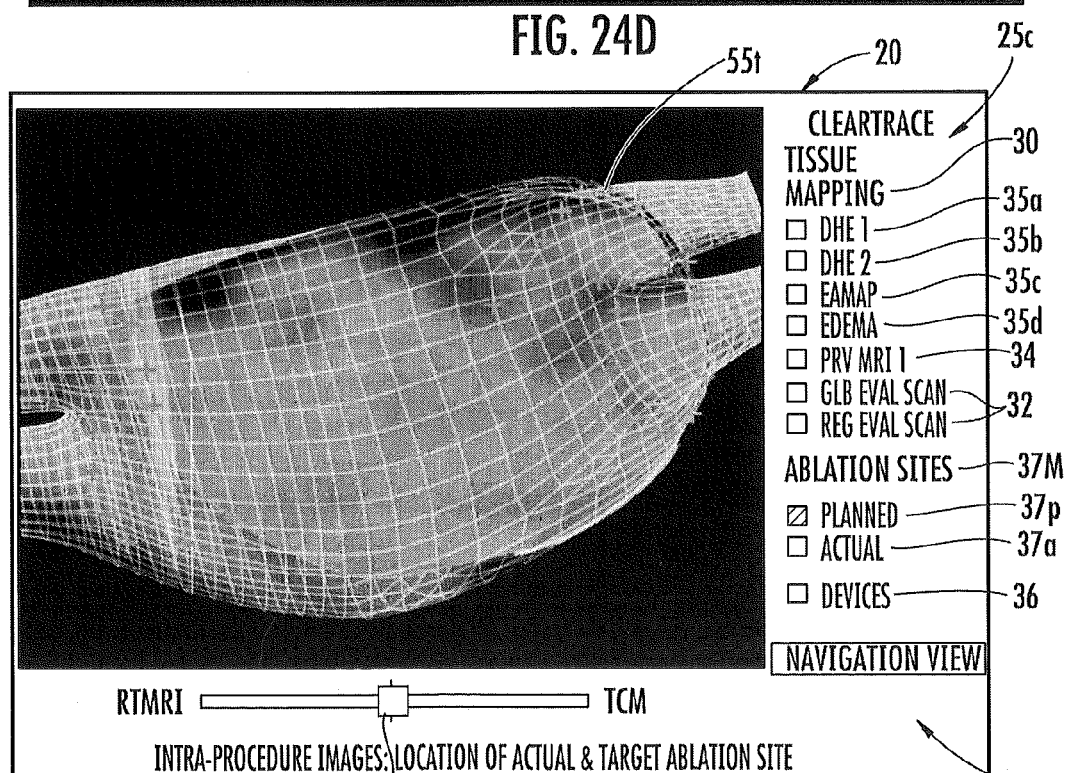
FIGS. 25-28 are yet additional exemplary (contemplated) screen shots illustrating patient data and target (clinician identified) treatment zones that can provide information that can help drive clinical decisions according to embodiments of the present invention.
Figure 26:
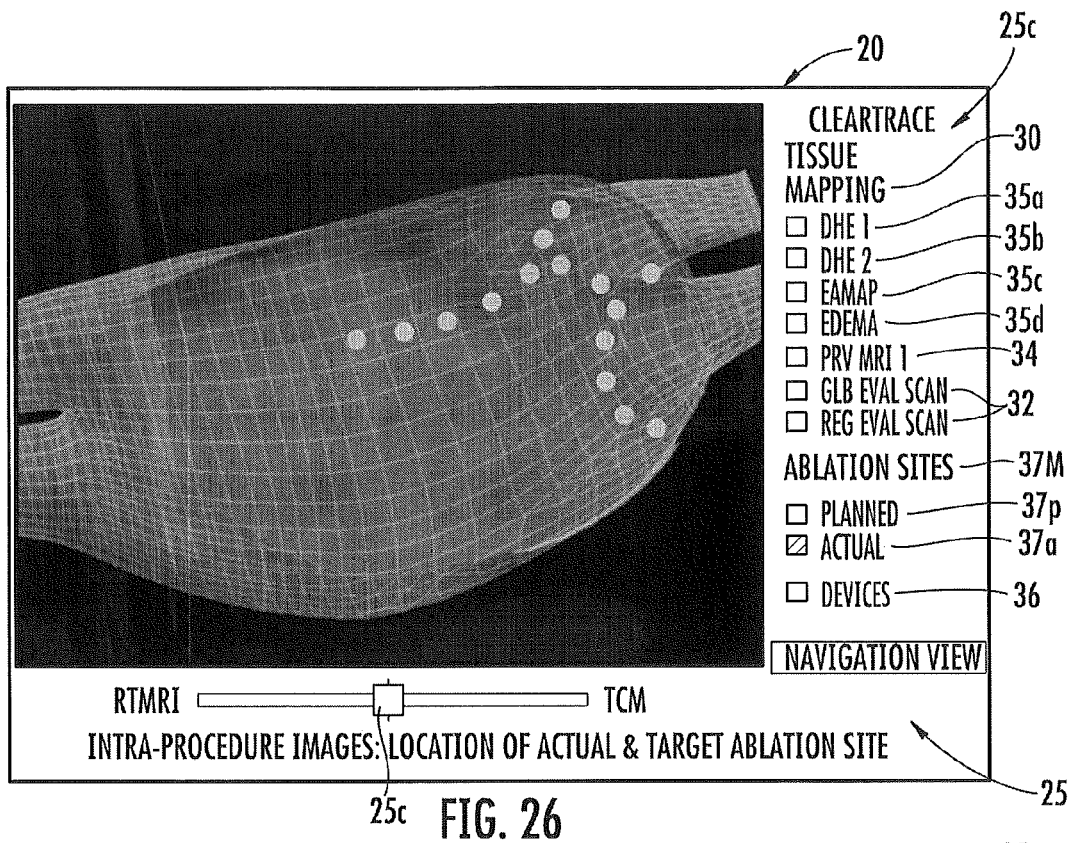

Referring to FIGS. 8, 12, and 25, in some embodiments, the UI 25 can also include a user input control 25c to allow a user to identify and/or select (e.g., mark) target ablation sites 55t on a tissue planning map 37M and subsequently provide planned and actual ablation tissue maps 37a or (which may be overlaid with different colors for easy comparison in viewing) or merged into a composite map that indicates both planned and actual sites (FIG. 10).

FIGS. 14, 17 and 22A-22B illustrate enlarged (high resolution image) views of tissue that can be shown based on actual MR image data. This allows a physician to see the tissue that is targeted for treatment (e.g., ablation) prior to and/or during treatment (e.g., ablation). This type of viewing can be carried out during a planning stage or to evaluate lesions after ablation rather than just during the treatment for tissue-specific data. In some embodiments, the enlarged image views can be shown in response to user input in the interactive visualization. That is, the image views can be based on the placement of a target treatment site 55t in or on the map 100M.

Figure 14:
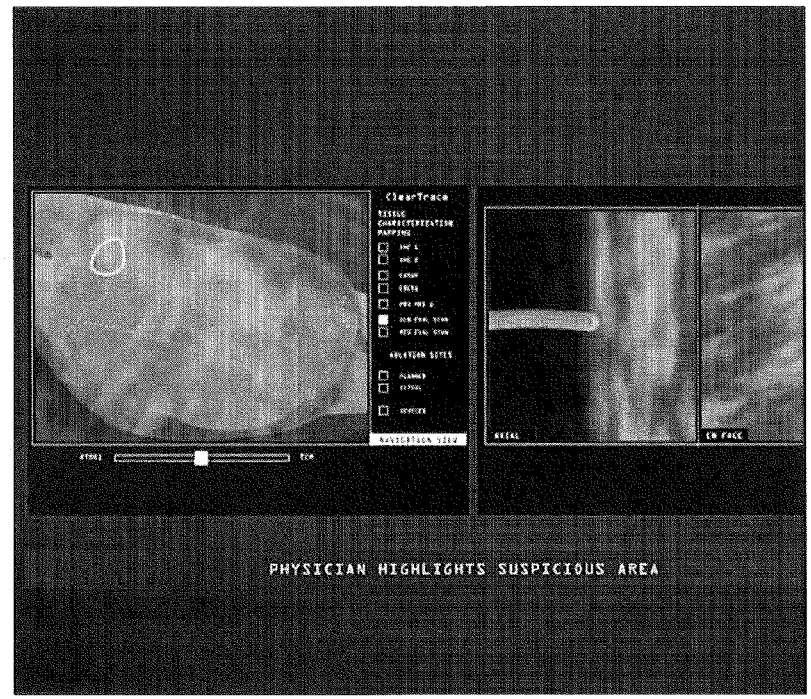
Figure 15:
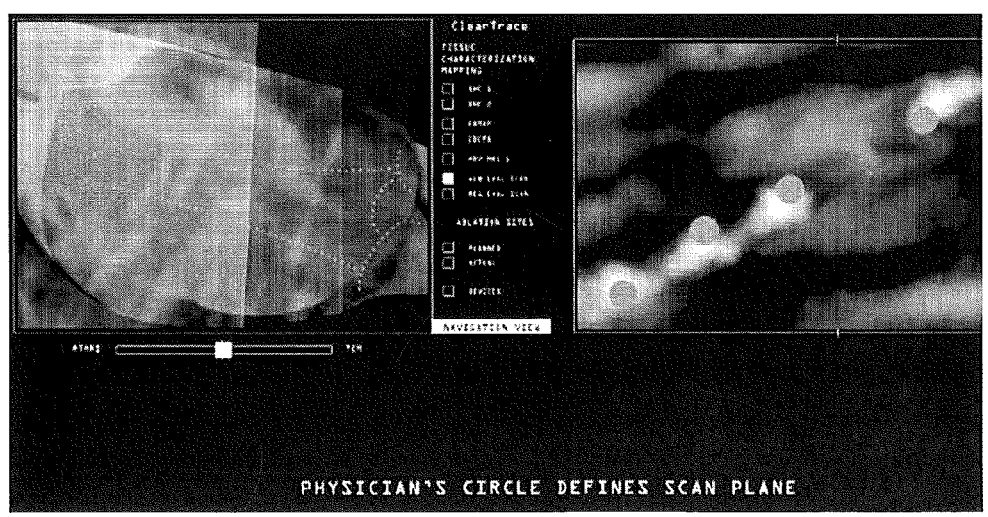
Figure 16:
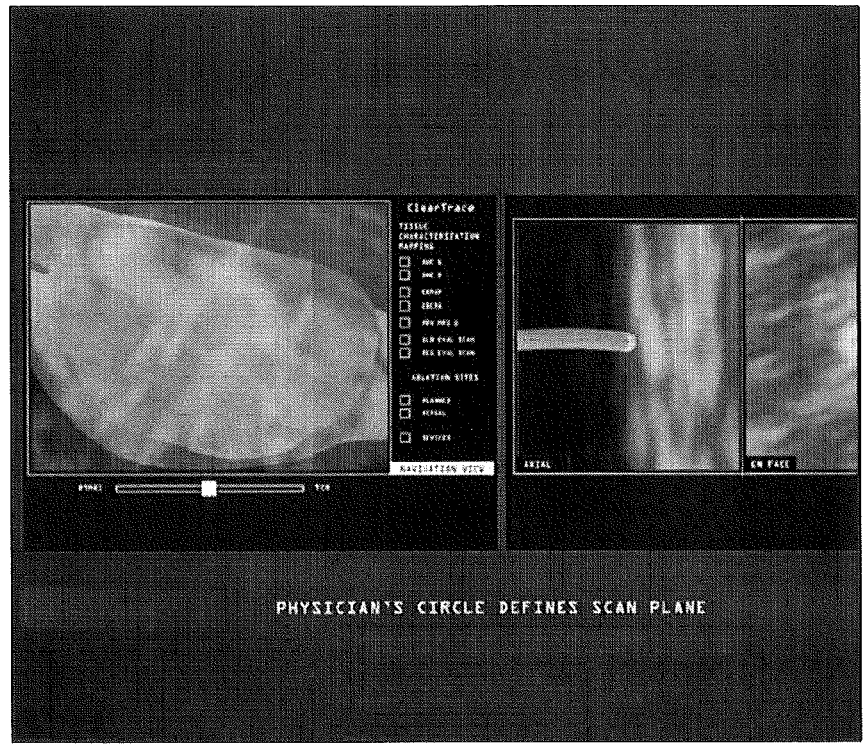

FIG. 14 illustrates that a clinician (physician) can mark an area on the model 100M of the interactive visualization 100v shown as a circle toward the left side of the left window. FIG. 15 shows that the lesion pattern may be incomplete. FIG. 16 illustrates that the marked area in FIG. 14 may define the scan plane for the close-up views in the right hand viewing window.

FIGS. 10, 12 and 13 illustrate a "complete" planning map 37M with a number of target ablation sites 37p/55t for forming desired transmural lesions and/or electrical isolation patterns as selected by the physician (user). FIG. 10 illustrates both planned and actual treatment sites. After a planned ablation pattern is indicated, or as a mark or particular lesion site is selected and/or placed on the planning map 37M, a physician/user can review real-time MR image data of the spot and affirm the selected site is a desired target ablation site(s) 55t. FIG. 8 illustrates that the display can show a planned ablation site pattern 55t applied to the model 100M along with near real time patient MRI data.

In some embodiments, the planned treatment (e.g., ablation) pattern can use an electronically generated (default) template based on a predefined condition to be treated and certain fiducials associated with the target anatomy. The template may also be based on a clinician-specific preference for such a condition that can be electronically stored for use over different patients. The template can be modified based on patient-specific anatomy or other information. The ablation pattern can be electronically "drawn" or marked on the model 100M prior to its registration in the image space. The system can be configured to electronically identify relevant scan planes for the different marked lesion sites or areas after registration in the image space or propose scan planes that match contour of local anatomy that will include the target ablation site(s).

FIG. 17 illustrates that the display can show the interactive visualization 100v in one viewing window and that previous ablations in the indicated region can have an electronic associated scan plane(s) that can be used to define a new (or current) scan plane for regional evaluation of the lesion or other therapy.

Figure 20:
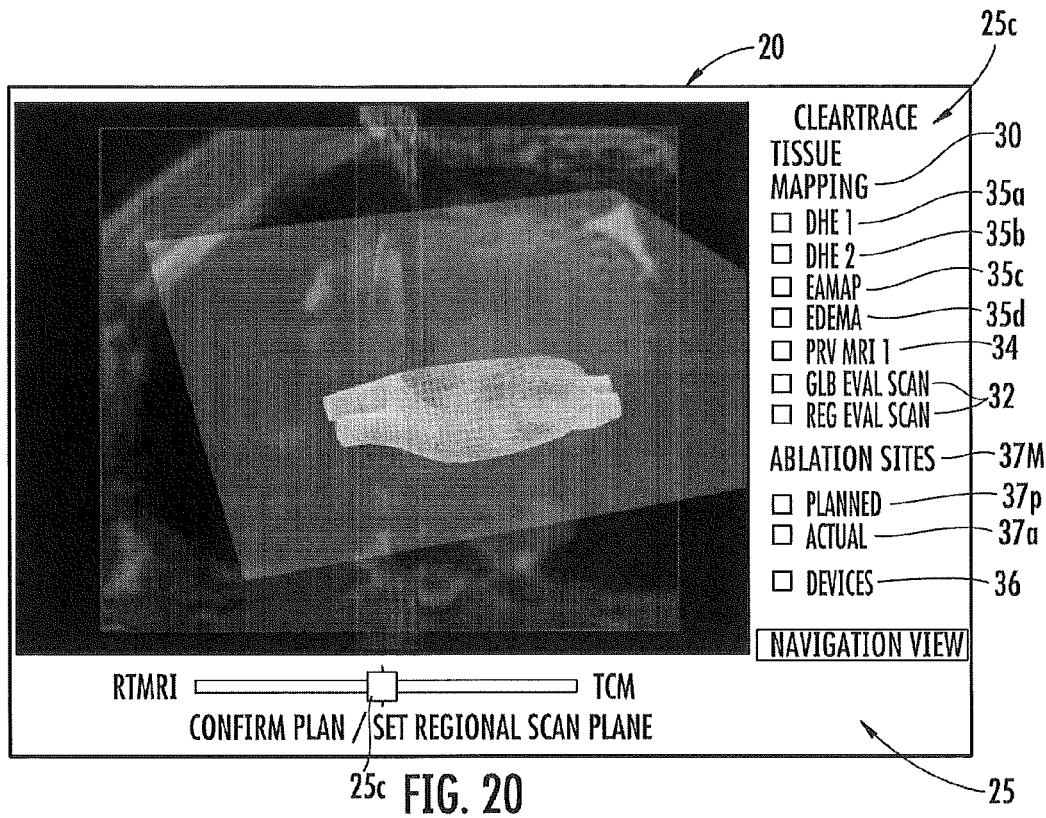

FIG. 20 shows that the visualization 100v can be used to confirm a desired therapy plan (ablation sites) and set a regional scan plane. Note also the difference from FIG. 8 with the visualization showing the model more predominant than the MR image data according to user input.

The model/map 100M can be shown in wire grid form (FIG. 9) or in varying intensity or opacity based on user input or default settings. FIG. 9 also shows the near RT image data suppressed or not shown in the visualization 100v.

FIG. 22A shows that scan planes for the therapeutic (e.g., ablation) view(s) can be automatically determined based on the identified location of the tracking coil(s) 82c as discussed above.

The circuit 60c can electronically define and pre-set scan planes associated with a respective target ablation site correlated to an actual location in 3-D space which is then electronically stored in electronic memory as pre-set scan planes for that target location. The MRI images in treatment-view mode (e.g., ablation-view mode) can automatically be displayed when the treatment device 80 reaches the corresponding physical location in the target anatomy (e.g., heart) during the procedure. The planned target sites 55t may also used to define the physician view (3-D perspective), e.g., a preset view, whenever the treatment device 80 (e.g., ablation catheter) is in proximity to the defined location associated with the target site. Thus, the target sites 55t identified in the planning map 37M can be used to preset both associated scan planes with real time MRI and the 3-D view for display without requiring further clinician input.

During the procedure, as the distal end 80t of the device 80 (e.g., ablation catheter) approaches a location that corresponds to a target treatment (e.g., ablation) site 55t, the circuit 60c (e.g., MR Scanner 10S) can automatically select scan planes that "snap to" the tip location using a scan plane defined "on the fly" based on the location of the end of the device (typically selected so that the slice includes a region projected forward a distance beyond the tip of the device such as between about 0-4 mm, typically about 1-2 mm) and/or using one or more of the preset scan planes associated with that location to obtain real-time MR image data of the associated tissue. The scan planes can be adjusted in response to movement of the device (as typically detected by tracking coils) prior to or during treatment. FIG. 11 indicates an auto-view using a recalled preset scan plane as the device 80 nears or contacts target tissue.

For example, in some embodiments, the circuit 60c and/or MR Scanner 10S can adjust the scan planes if the physician moves the ablation catheter to obtain slices that show the ablation of the lesion including side and en face views showing substantially real-time MRI of the tissue being ablated. The scan planes are selected to include slices that are projected outward a distance axially along the line of the device to include relevant tissue.

In addition to substantially continuous collection of "new" image data in the visualizations and/or ablation or other therapy view modes, the data can also be processed by algorithms and other means in order to generate and present back to the surgeon in near real-time or upon request, a continuously updated, patient specific anatomical tissue characterization map of the anatomy of interest.

Figure 23:
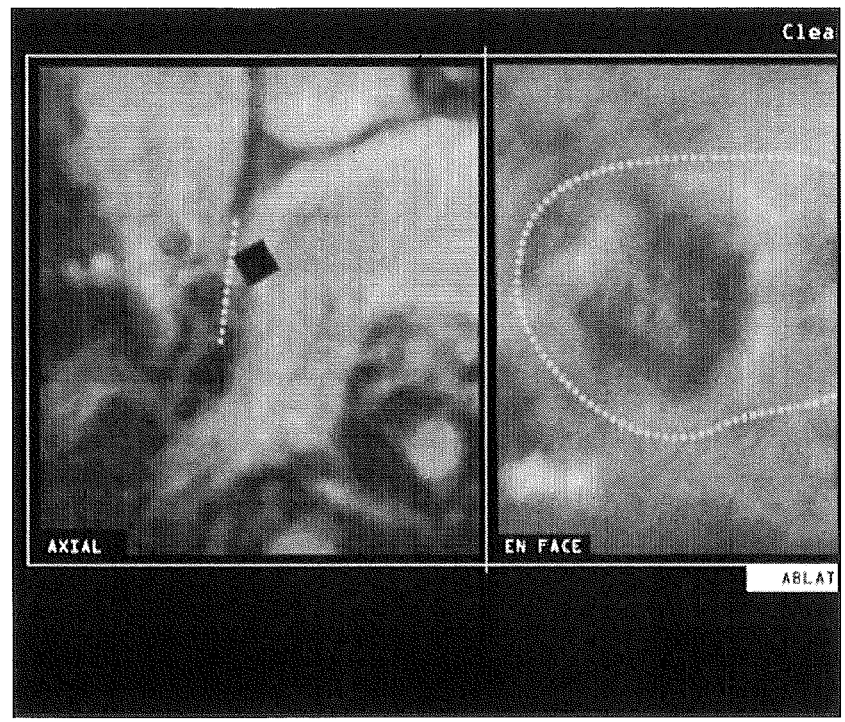
FIGS. 23 and 24A-D are exemplary (contemplated) screen shots illustrating navigational indicia that can be used to help guide and/or position an intrabody device according to embodiments of the present invention.
Figure 24A:
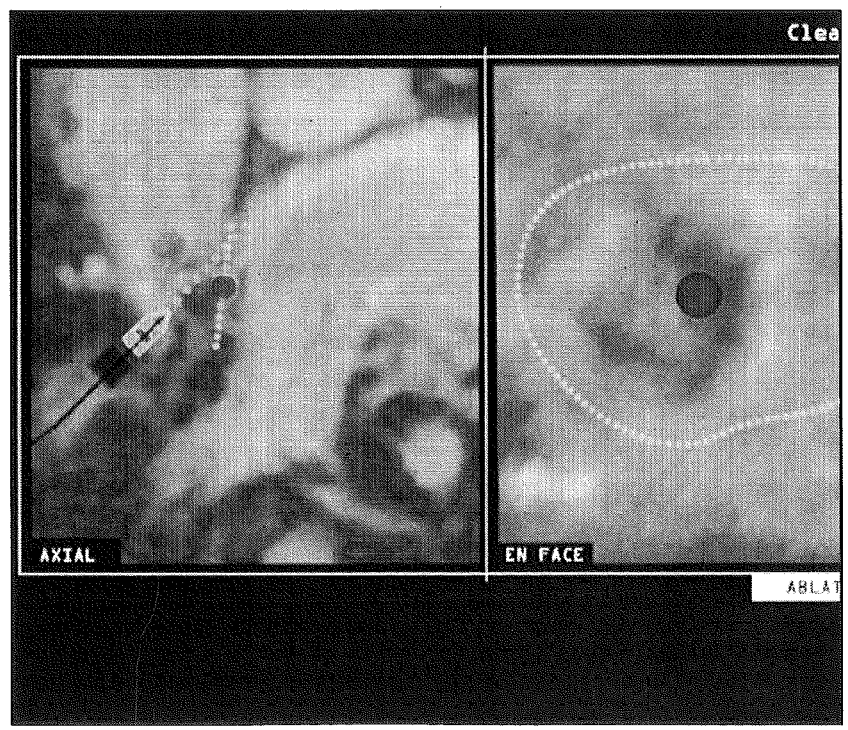
Figure 24B:
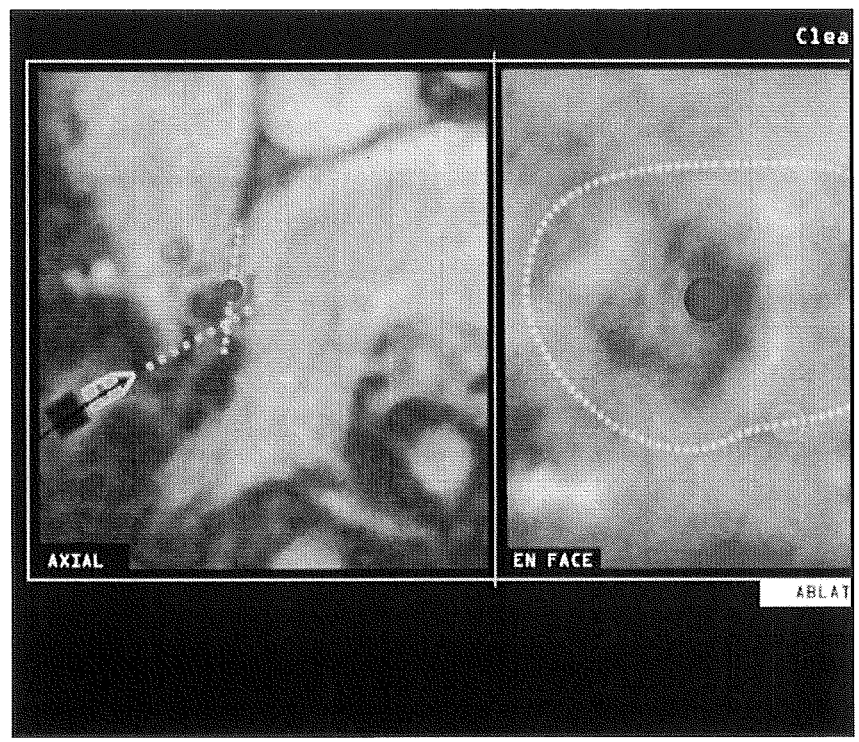
Figure 24C:
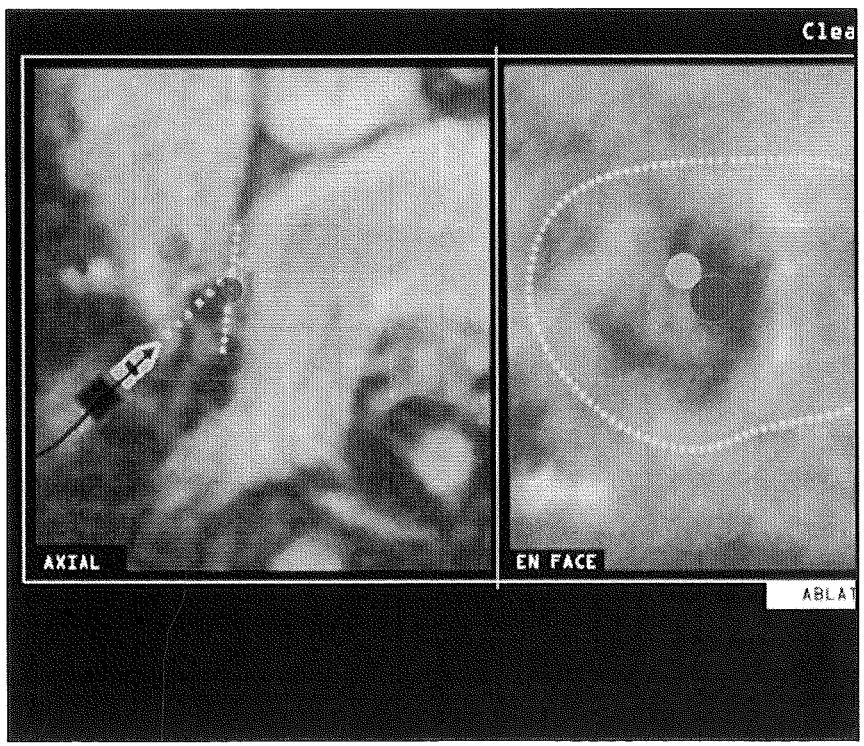
Figure 24D:
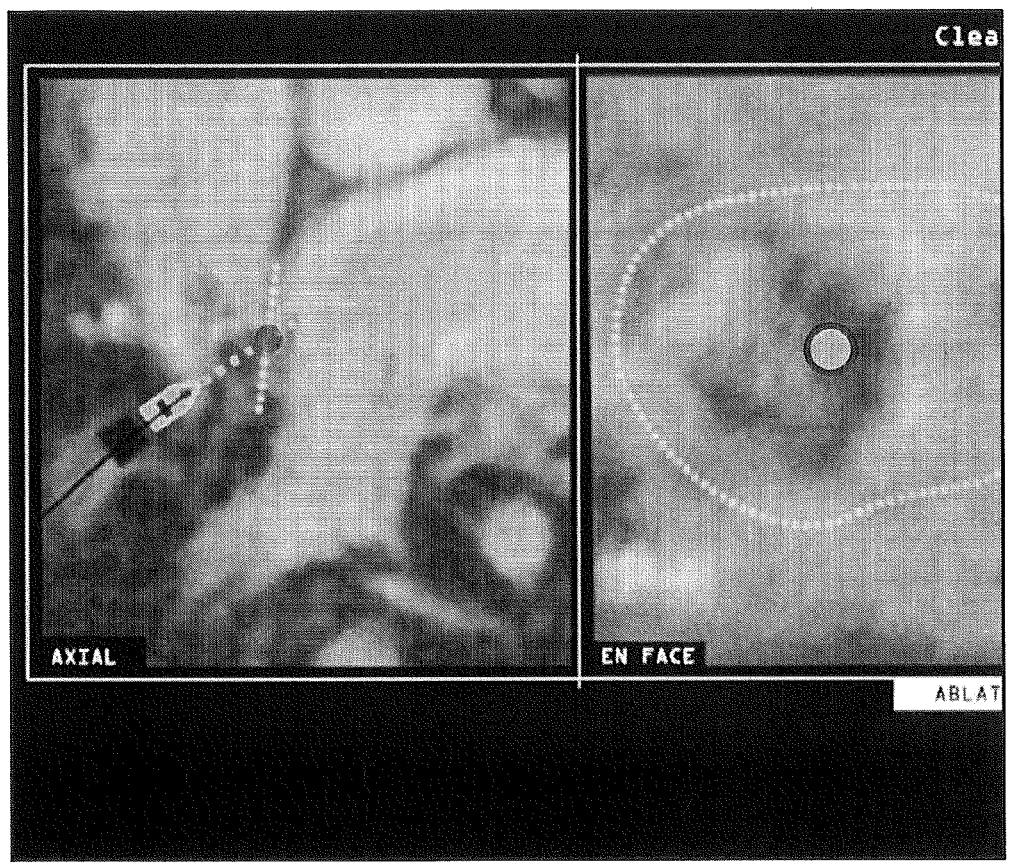

FIG. 23 illustrates that the system can illustrate the location of the treatment device 80 with additional visual indicators and a "target" mark for help in navigation to the site.

FIGS. 24A-24D illustrate that the system can generate visual navigational markers for facilitating alignment using MRI-guidance.

In particular embodiments, during ablation, MR thermometry (2-D) can be used to show real-time ablation formation taking a slice along the catheter and showing the temperature profile increasing. It is contemplated that 2D and/or 3D GRE pulse sequences can be used to obtain the MR image data. However, other pulse sequences may also be used.

Figure 18:
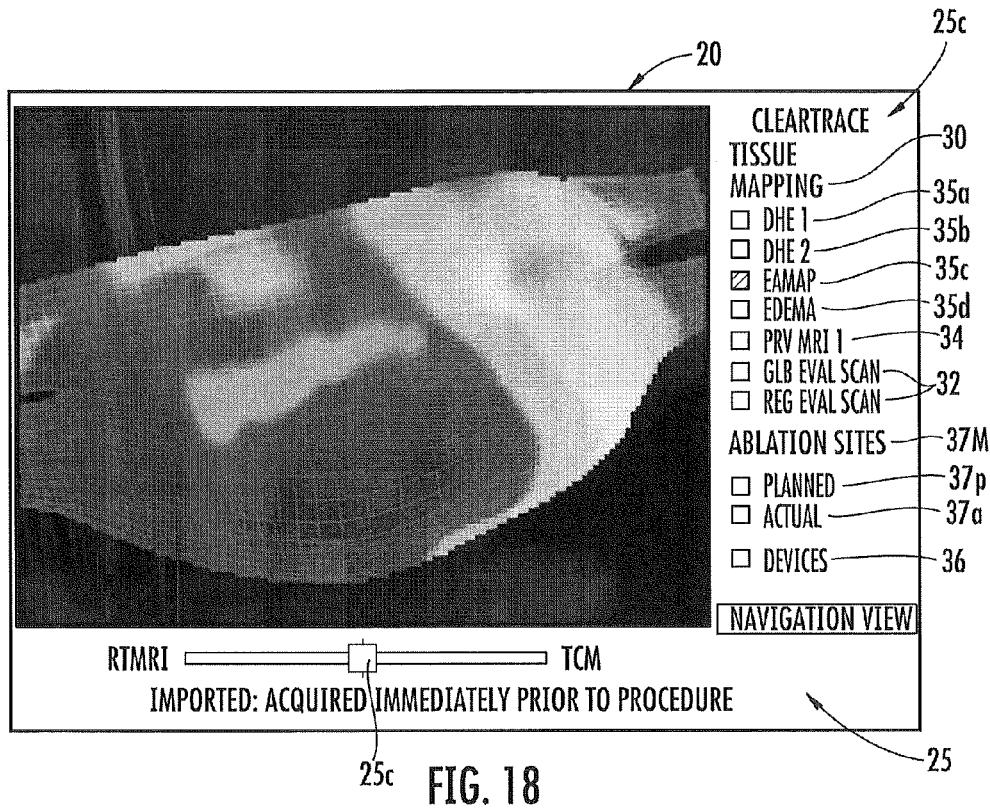

FIGS. 18 and 19 illustrate examples of maps 30 of pre-acquired patient data that can be imported (and registered to the image space) for use during a cardiac interventional procedure, typically used as the map 100M in the interactive visualization 100v. As shown in FIG. 18, an EA map can be obtained prior to (typically immediately prior to) the actual interventional procedure either while the patient is in the MRI scanner or from an X-ray based system from which the EA map can be registered to a different map, such as a tissue characterization map 30 and shown on the display 20. In some embodiments, the tissue characterization map can include, incorporate, overlay or underlay data from or an EA map (which may be imported from an X-ray imaging modality or generated in an MRI Scanner) to define an integrated electro and tissue characterization combination map. The electrical activity can be detected via electrical activity sensors that can detect impedance or other electrical parameter that can sense fractionated or normal electrical activity in cardiac tissue as is known to those of skill in the art. The electroanatomical map or data therefrom, where used, can be registered to the visualization map 100M (e.g., a different tissue-characterization map) so that MR data updates using MR data that is generated during the intervention can be generated and displayed on the integrated map.

Also, the UI 25 can be configured to allow a clinician to select or deselect the EA map (where used) so that the information from the EA map is electronically stripped or removed (and/or added back in) to the map 100M as desired. In other embodiments, the map 100M is maintained separate from the EA map, and if used, the EA map is shown in a separate window or screen apart from the tissue characterization map.

Figure 21:
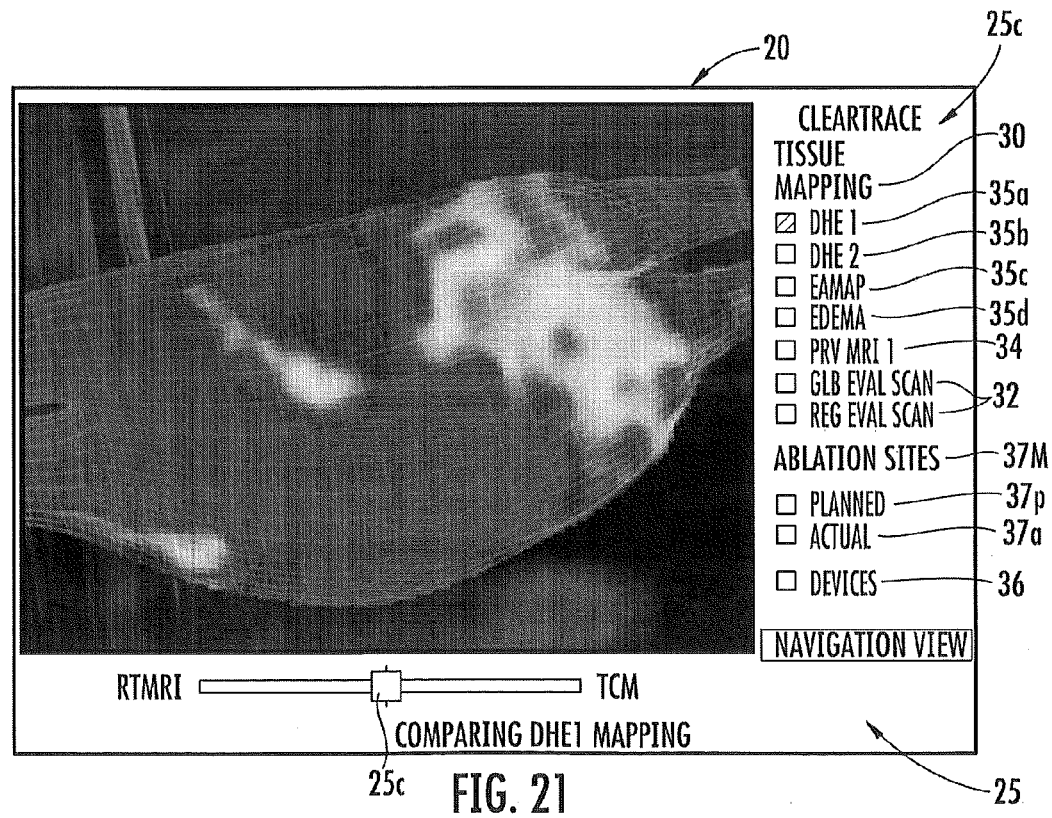

FIGS. 21 and 27 show examples of MRI DHE tissue characterization maps. FIG. 21 shows a pre-procedure "planning" DHE image taken before, typically about 1 week before, the planned procedure. In some embodiments, a DHE image can be taken after a prior ablation procedure illustrating locations of incomplete electrical isolation/scar formation for helping plan the target sites for the current procedure. A planning map can be placed over the map in the visualization so that a user/physician can mark the target ablation sites 55t as discussed above (which may in some embodiments also define preset scan planes and views before ablating during a procedure). FIG. 27 shows an intraprocedure DHE map that can be used to evaluate the ablation sites.

FIG. 28 illustrates that the map 100M can be rendered to show locations of target and actual ablation sites (in different colors) to allow a clinician to evaluate the scar formations and/or variation from the planned procedure intra-procedure according to embodiments of the present invention.

The MRI Scanner 10S (FIGS. 1-3) can be operated substantially continuously to provide image data that can be used to generate updated maps 100M in the visualizations upon request or automatically. This operation can be "in the background", e.g., transparent to the user so as not to slow down the procedure while providing updated image and tracking data during the course of the procedure.

In some embodiments, the device-tissue interface 100i (FIG. 1, 22A, 22B) can be visualized with a T1-weighted FLASH sequence (T1w FLASH) to localize the tip 80t. RF or other ablative energy can be delivered and myocardial or other target tissue changes and lesion formation can be visualized in near real-time using a T2 weighted HASTE (T2w HASTE) sequence. Real Time (RT)-MRI sequence, T1w FLASH and T2w HASTE image slices can be aligned to allow visualization of the device 80 upon tissue contact or activation of the ablation energy to allow visualization of the device 80 (e.g., catheter), the device-tissue interface 100i and/or the (myocardium) tissue while receiving the therapy, e.g., ablative energy.

In some particular embodiments, during navigation mode (rather than an ablation mode), the catheter 80 can be visualized using a different pulse sequence from that used in the high-resolution ablation mode, such as, for example, an RT MRI sequence using GRE or SSFP (e.g., TrueFISP) pulse sequence with about 5.5 fps), the tracking coils 82c can be used for spatial orientation and positioning. Typical scan parameters for (near) real-time include: echo time (TE) 1.5 ms, repetition time (TR) 3.5 ms, a flip angle of about 45 degrees or about 12 degrees, slice thickness 5 mm, resolution 1.8 mm×2.4 mm, parallel imaging with reduction factor (R) of 2. In some embodiments using SSFP, the flip angle is about 45 degrees.

Once the device position is deemed appropriate (using tracking coils 82c), a pulse sequence at the associated scan plane can be used to generate high resolution visualization of the catheter tip 80t and (myocardial) tissue interface. For example, a T1-weighted 3D FLASH sequence (T1w FLASH) as noted above. Myocardial or other target tissue images during ablation or other therapy can be acquired using an Inner Volume Acquisition (IVA) dark-blood prepared T2-weighted HASTE (T2w HASTE) or dark-blood prepared Turbo Spin Echo (TSE) sequence. Examples of HASTE and TSE sequence parameters include: TE=79 ms/65 ms, TR=3 heart beats, 3 contiguous slices with thickness of about 4 mm, resolution 1.25 mm×1.78 mm/1.25 mm×1.25 mm, fat saturation using SPAIR method, and parallel imaging with R=2, respectively.

Typical heart beat rates and free breathing can present imaging challenges. In some embodiments, (near) RT navigation imaging slices (e.g., GRE pulse sequence at 5.5 fps) can be aligned with high-resolution tissue interface slices (e.g., T1w FLASH) for visualization of the catheter-tissue interface. Subsequently, those slices obtained with T1w FLASH can be aligned with those obtained with dark-blood prepared T2w Haste images for myocardial tissue/injury characterization during energy delivery. This stepwise approach can allow confident localization of specific points within the atrium and while ablating tissue and simultaneously visualizing the tissue for near-real time assessment of tissue injury associated with lesion formation.

In some embodiments, slices acquired with different sequences can be interlaced to provide an interactive environment for catheter visualization and lesion delivery, a UI can allow a user to toggle between these views or can alternate the views based on these image slices or navigation versus ablation or interventional modes/views. It is also noted that the sequences described herein are provided as examples of suitable sequences and it is contemplated that other known sequences or newly developed sequences may be used for cardiac ablation or other anatomy or interventional procedures.

Figure 29:
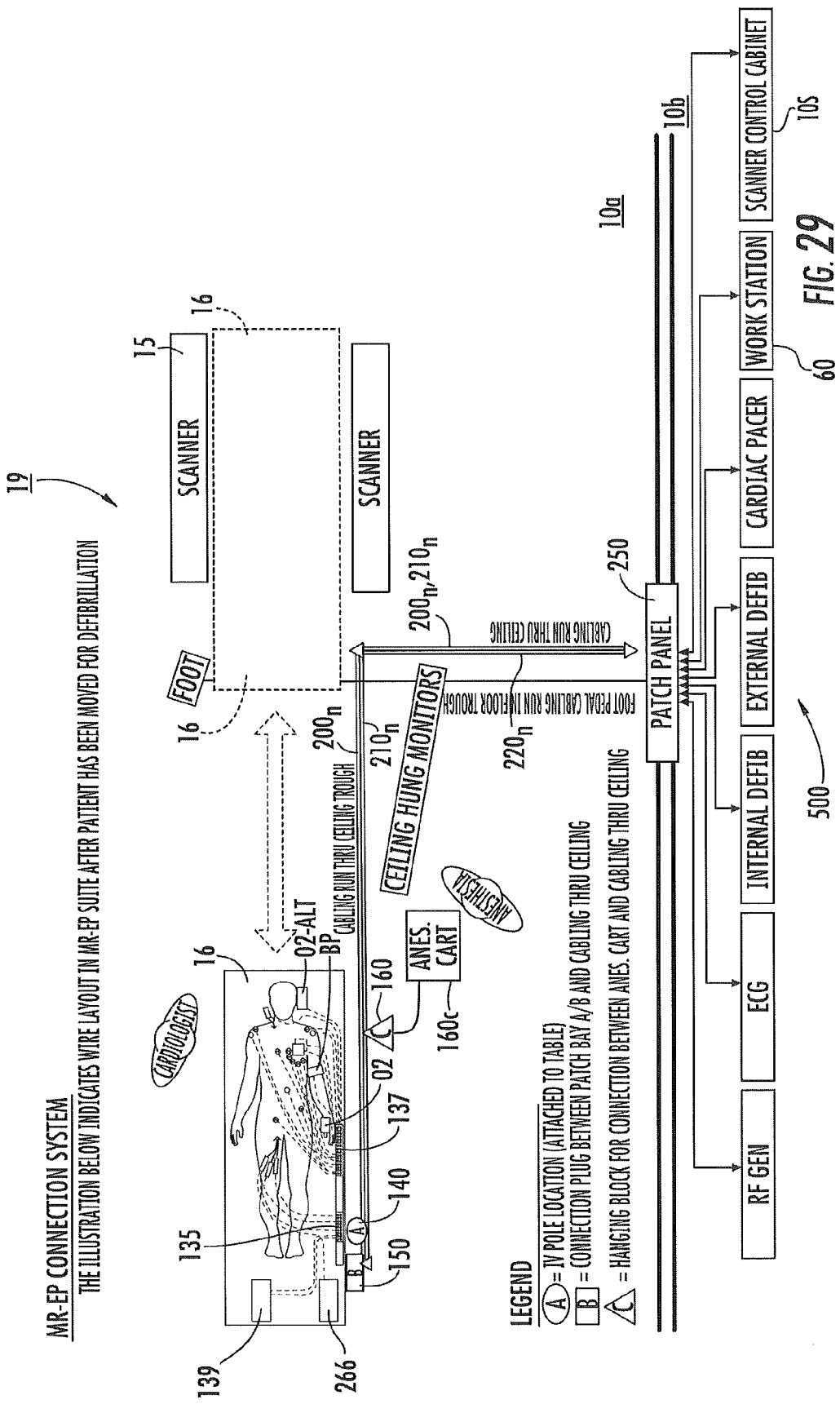
FIG. 29 is a schematic illustration of an MRI-interventional suite according to embodiments of the present invention.

FIG. 29 illustrates one particular embodiments using a cardiac MRI Interventional suite 19 with an integrated cable management system that connects multiple patient connected leads that remain in position even when a patient is translated in or out of a magnet bore on the gantry 16 (the magnet can be an open face or closed magnet configuration) to allow a clinician direct access to a patient. The other ends of the leads connect to power sources, monitors and/or controls located remote from the patient (typically in the control room not the magnet room). As shown in FIG. 29, the MRI interventional suite 19 can include an IV pole 140 (typically attached to the scanner table/gantry 16) and a connection block 150 of cables 200n that are routed through a ceiling (e.g., they extend up, through and above a ceiling) (where "n" is typically between about 1-400, typically between about 5-100), that connect to patch bay 135 and/or 137. Cabling 210n for anesthesia cart 160 can also be routed through the ceiling (where n is typically between about 1-400, typically between about 5-100). The cabling 200n, 210n extends through the ceiling between the rooms 10a, 10b and can connect to the remote devices 500 through a patch panel 250. In some embodiments foot pedal cabling 220n can extend through a floor trough to the patch panel/second room 10b as well (where "n" is typically between about 1-100 cables). For additional description of an exemplary cardiac suite, see, U.S. patent application Ser. No. 12/708,773, the contents of which are hereby incorporated by reference as if recited in full herein. The cables may also alternately be routed under, on or over the floor, suspended on walls, employ wireless connections and the like (and combinations of same).

As is known to those of skill in the art, there are typically between about 60-100 lesions generated during a single patient cardiac (AFIB) EP procedure. Other cardiac procedures may only require about 1 ablation or less than 60. A typical patient interventional cardiac procedure lasts less than about 4 hours, e.g., about 1-2 hours. Each lesion site can be ablated for between about 30 seconds to about 2 minutes. Linear transmural lesions (such as "continuous" drag method lesions) may be generated or "spot" lesions may be generated, depending on the selected treatment and/or condition being treated. The continuous lesion may be formed as a series of over lapping spot ablation lesions or as a continuous "drag" lesion.

The system can include a monitoring circuit can automatically detect which devices are connected to the patient patch bay. One way this can be achieved is by using ID resistors in the patch bay and/or interface as well as in various devices that connect thereto. The MRI scanner computer or processor or the clinician workstation module or processor can monitor resistors via connections CON1, CON2 and CON3. The devices 80 (FIG. 1) can have built-in resistors that modify the resistance by lines that connect to CON1, CON2 and CON3. Variation in resistance values helps the monitor which device is connected. Once that determination is made the scanner may automatically load special acquisition parameters, display parameters and update the progress of the procedure to display on the display 20 such as at workstation 60 (FIG. 3), for example.

Electrical isolation between the MR Scanner 10S and the device 80 can be provided via low pass filters inside and outside the MRI suite. As is known to those of skill in the art, components in the MRI Suite can be connected to external components using a waveguide built into the RF shield that encloses the MRI suite. The ablation catheter 80 can be connected to an appropriate energy source, such as, for example, a Stockert 70 RF generator (Biosense Webster, Diamond Bar, Calif., USA) with MR compatible interface circuits configured for 3 T magnetic fields (where a 3 T system is used). The system can comprise an EP Suite with a Siemens Verio system (Siemens Healthcare, Erlangen, Germany) or other suitable scanner as well as suitable external imaging coils, such as spine and/or body array coils as is known to those of skill in the art.

Embodiments of the present invention may be utilized in conjunction with navigation and mapping software features. For example, current and/or future versions of devices and systems described herein may include features with adaptive projection navigation and/or 3-D volumetric mapping technology, the latter may include aspects associated with U.S. patent application Ser. No. 10/076,882, which is incorporated herein by reference in its entirety.

Although described primarily herein with respect to Cardiac EP procedures using ablation electrodes, other ablation techniques can be used, such as, for example, laser ablation, thermal (heated liquid) ablation and cryoablation. Similarly, the systems and components described herein can be useful for other MRI guided cardiac surgical intervention procedures, including, for example, delivering biologics or other drug therapies to target locations in cardiac tissue using MRI.

Some interventional tools may include an MRI receive antenna for improved SNR of local tissue. In some embodiments, the antenna has a focal length or signal-receiving length of between about 1-5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein. Image data can also include image data obtained by a trans-esophageal antenna catheter during the procedure. See, e.g., U.S. Pat. No. 6,408,202, the contents of which are hereby incorporated by reference as if recited in full herein.

As discussed above, embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller. The program code may execute entirely on one (e.g., a workstation computer or a Scanner's computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

The workstation 60 and/or interface 44, 84, or patch bay, may also include a decoupling/tuning circuit that allows the system to cooperate with an MRI scanner 10S and filters and the like. See, e.g., U.S. Pat. Nos. 6,701,176; 6, 904,307 and U.S. Patent Application Publication No. 2003/0050557, the contents of which are hereby incorporated by reference as if recited in full herein. In some embodiments, the intrabody device 80 is configured to allow for safe MRI operation so as to reduce the likelihood of undesired deposition of current or voltage in tissue (inhibit or prevent undesired heating). The device 80 can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current. The conductors connecting electrodes or other components on or in the catheter (or other interventional device) can also include a series of back and forth segments (e.g., the lead can turn on itself in a lengthwise direction a number of times along its length) and/or include high impedance circuits. See, e.g., U.S. patent application Ser. Nos. 11/417,594; 12/047,602; and 12/090, 583, the contents of which are hereby incorporated by reference as if recited in full herein.

Although not shown, in some embodiments, the device can be configured with one or more lumens and exit ports and can be used and/or deliver desired cellular, biological, and/or drug therapeutics to a target area.

Figure 30:
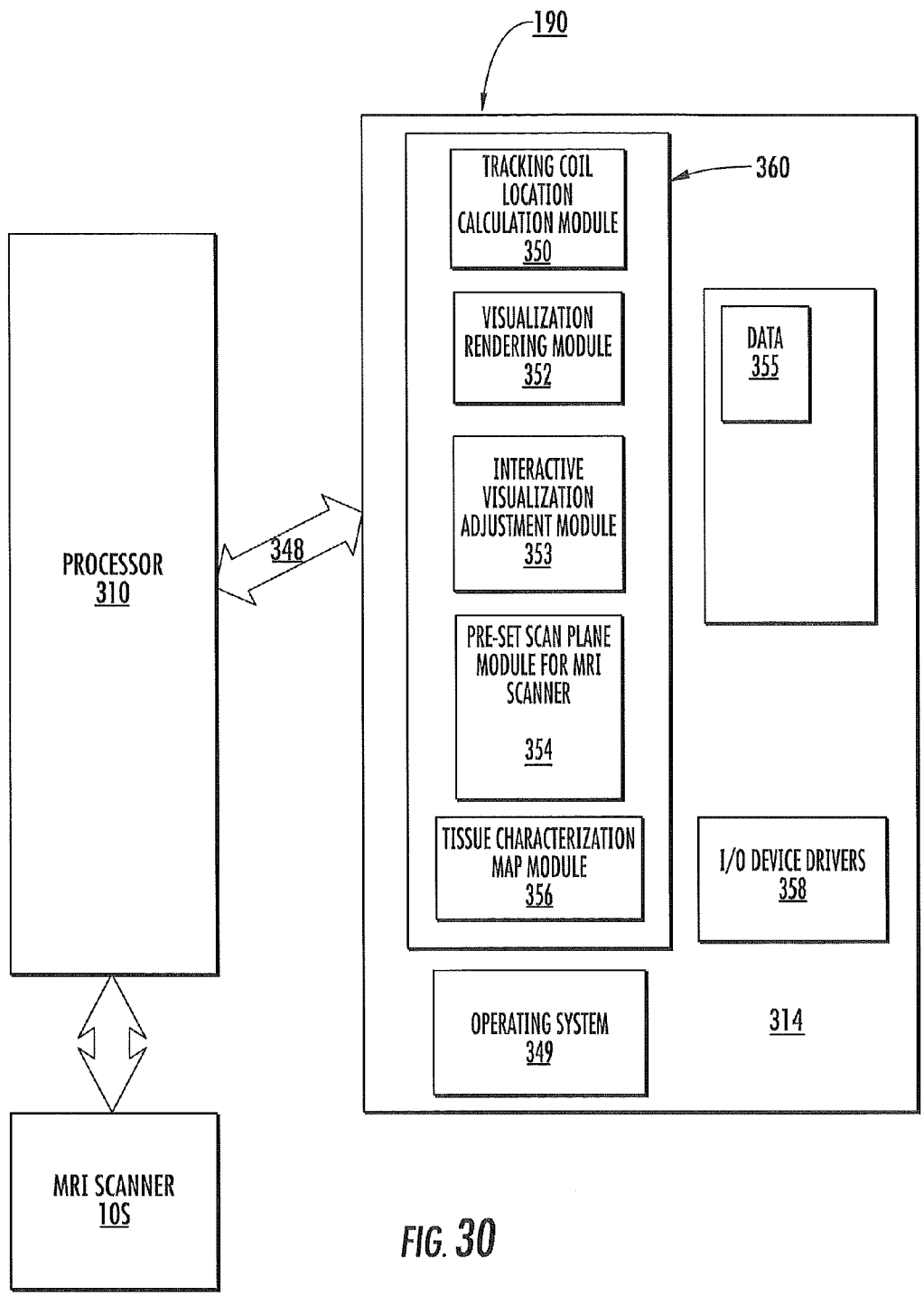
FIG. 30 is a schematic illustration of a data processing circuit or system according to embodiments of the present invention.

FIG. 30 is a schematic illustration of a circuit or data processing system 190 that can be used with the system 10. The circuits and/or data processing systems 190 may be incorporated in a digital signal processor in any suitable device or devices. As shown in FIG. 30, the processor 310 communicates with and/or is integral with an MRI scanner 10S and with memory 314 via an address/data bus 348. The processor 310 can be any commercially available or custom microprocessor. The memory 314 is representative of the overall hierarchy of memory devices containing the software and data used to implement the functionality of the data processing system. The memory 314 can include, but is not limited to, the following types of devices: cache, ROM, PROM, EPROM, EEPROM, flash memory, SRAM, and DRAM.

FIG. 30 illustrates that the memory 314 may include several categories of software and data used in the data processing system: the operating system 349; the application programs 360; the input/output (I/O) device drivers 358; and data 355. The data 355 can also include device (ablation catheter) dimensions (e.g., distance of a tracking coil to the tip) and patient-specific image data 355. FIG. 30 also illustrates the application programs 354 can include a Tracking Coil Location Identification Calculation Module 350, a Visualization Rendering Module 352, an Interactive Visualization (and UI) Module 353, a Tissue Characterization Map Module 356, and a Pre-Set Scan Plane to Target Ablation Site Module 354, a and a UI Interface Module 353.

As will be appreciated by those of skill in the art, the operating systems 349 may be any operating system suitable for use with a data processing system, such as OS/2, AIX, or z/OS from International Business Machines Corporation, Armonk, N.Y., Windows CE, Windows NT, Windows95, Windows98, Windows2000, WindowsXP, Windows Visa, Windows7, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems. For example, VxWorks which can run on the Scanner's sequence generator for precise control of pulse sequence waveform timings.

The I/O device drivers 358 typically include software routines accessed through the operating system 349 by the application programs 360 to communicate with devices such as I/O data port(s), data storage 356 and certain memory 314 components. The application programs 360 are illustrative of the programs that implement the various features of the data processing system and can include at least one application, which supports operations according to embodiments of the present invention. Finally, the data 356 represents the static and dynamic data used by the application programs 360, the operating system 349, the I/O device drivers 358, and other software programs that may reside in the memory 314.

While the present invention is illustrated, for example, with reference to the Modules 350, 352, 353, 354, 356 being application programs in FIG. 30, as will be appreciated by those of skill in the art, other configurations may also be utilized while still benefiting from the teachings of the present invention. For example, the Modules and/or may also be incorporated into the operating system 349, the I/O device drivers 358 or other such logical division of the data processing system. Thus, the present invention should not be construed as limited to the configuration of FIG. 30 which is intended to encompass any configuration capable of carrying out the operations described herein. Further, one or more of modules, i.e., Modules 350, 352, 353, 354, 356 can communicate with or be incorporated totally or partially in other components, such as separate or a single processor, an MRI scanner 10S or workstation 60.

The I/O data port can be used to transfer information between the data processing system, the workstation, the MRI scanner, and another computer system or a network (e.g., the Internet) or to other devices controlled by the processor. These components may be conventional components such as those used in many conventional data processing systems, which may be configured in accordance with the present invention to operate as described herein.

Non-Limiting Examples of Tissue Characterization Maps will be discussed below.

Thermal Tissue Characterization Map

The thermal tissue characterization map can be based on thermal status at a given point in time or may be provided as a composite of heating of different tissue locations at different times (e.g., during and/or after ablation of different points at different times of the ablation procedure). The thermal map can be registered to a location of the internal ablation catheter (e.g., tip) at different times so that the location of the ablation catheter tip is correlated to the thermal activity/status at that location at that time as that is the time frame that the image data for that region illustrating increased thermal activity/heating is generated. That is, the image scan planes are taken to show the tissue at the location of the ablation catheter tip. The image scan planes are typically projected forward a known distance from the tracking coil so that the lesion tissue in front of the ablation tip is imaged.

The MR thermal data can be obtained using temperature imaging techniques (MR thermometry) to show temperature or phase variance. Examples of pulse sequences include, for example, SSFP and 2D GRE.

Vasculature Tissue Characterization Map

Segmented MRA (Magnetic Resonance Angiography) imaging volumes of a patient can be used to generate a vasculature tissue characteristic map which may indicate areas of increased blood flow and/or larger and smaller channels within the vasculature structure.

Fibrous Tissue Characterization Map

Contrast-based or non-contrast based MRI images of the patient can identify fibrous tissue in target tissue (e.g., the heart).

Contrast-Based Tissue Characterization Maps

Tissue damage can be shown or detected using MR image data based on contrast agents such as those agents that attach to or are primarily retained in one of, but not both, healthy and unhealthy tissue, e.g., the contrast agent is taken up by, attaches to, or resides or stays in one more than in the other so that MR image data will visually indentify the differences (using pixel intensity). The contrast agent can be one or more of any known or future developed biocompatible agent, currently typically gadolinium, but may also include an antibody or derivative or component thereof that couples to an agent and selectively binds to an epitope present in one type of tissue but not the other (e.g., unhealthy tissue) so that the epitope is present in substantially amounts in one type but not the other. Alternatively, the epitope can be present in both types of tissue but is not susceptible to bind to one type by steric block effects.

A tissue characteristic map registered to the imaging space can allow a clinician to assess both scar formation (isolation of the PV) and the volume of enhancement on a LA myocardial volume may indicate a poor outcome prediction and a clinician may decide to continue ablating or alter the ablation location or protocol (e.g., drive a clinical decision).

Examples of pulse sequences that can be used for delayed hyper-enhancement MRI include, for example, gradient echo, SSFP (steady state free precession) such as TrueFISP on Siemens MRI Scanners, FIESTA on GE MRI Scanners, and b-FFE on Philips MRI Scanners.

Edema Tissue Characterization Maps

After (and/or during) ablation, tissue will typically have edema. This can be detected in MRI using, for example, pulse sequences such as T2-weighted Turbo-Spin-Echo, HASTE (a Siemens term), SSFP, or T2-weighted gradient recalled echo (GRE).

Some tissue characterization maps may show edema and thermal maps overlaid or otherwise combined as a composite map that can be used to evaluate a procedure. For example, to visually assess whether there is complete or incomplete scar formation to isolate pulmonary veins. It is believed that complete scar formation to isolate PV is associated with a better prognosis for AFIB.

Heart Wall Motion Tissue Characterization Maps

MRI can be used to assess heart wall motion. Abnormal motion can be visually indicated on the tissue characterization map. Examples of pulse sequences that may be used to determine heart wall motion include, for example, DENSE, HARP and MR tagging.

Thus, it will be appreciated that embodiments of the present invention are directed to systems, including hardware and/or software and related methodology to substantially continuously collect and construct, throughout an MRI-guided cardiac procedure, e.g., an MRI-guided procedure, a patient-specific anatomical tissue characterization map or associated data that can be shown on a map of a target anatomical structure/region (e.g., a chamber of the heart such as the atrium). Embodiments of the system can generate and show in pre-set views and in near-real time during the procedure tissue while it is being treated, e.g., ablated.

While embodiments have been primarily discussed with respect to an MRI-guided cardiac system, the system can be used for other anatomical regions and deliver or apply other therapies as well as for diagnostic procedures. For example, the esophagus and anatomy near the esophagus, e.g., the aorta, coronary arteries, mediastinum, the hepaticobiliary system or the pancreas in order to yield anatomic information about the structures in those areas, "pancreaticohepaticobiliary" structures (collectively the structures of the liver, gallbladder, bile ducts and pancreas), the tracheobronchopulmonary structure (structures including the lungs and the tracheobronchial tree), the nasopharynx system (e.g., a device introduced transnasally may be adapted for evaluating the arterial circle of Willis and related vascular structures for abnormalities, for example congenital or other aneurysms), the proximal aerodigestive system or the thyroid, the ear canal or the Eustachian tube, permitting anatomic assessment of abnormalities of the middle or inner ear, and further permitting evaluation of adjacent intracranial structures and lesions.

The systems and methods of the present invention may be particularly useful in those lesions whose extent is not readily diagnosed, such as basal cell carcinomas. These lesions may follow nerves into the orbit or into the intracranial area, extensions not evident with traditional imaging modalities to the surgeon undertaking the resection to provide real time information to the resecting surgeon or the surgeon performing a biopsy as to the likely areas of lymph node invasion.

It is also contemplated that the systems can be used in the "head and neck" which refers collectively to those structures of the ear, nose and throat and proximal aerodigestive system as described above, traditionally falling within the province of otorhinolaryngology. The term "head and neck," as used herein, will further include those structures of the neck such as the thyroid, the parathyroid, the parotid and the cervical lymph nodes, and will include also the extracranial portions of the cranial nerves, including but not limited to the facial nerve, this latter nerve being included from its entry into the internal auditory meatus outward. The term "head and neck, as used herein, will also include those structures of the orbit or of the globe, including the oculomotor muscles and nerves, lacrimal glands and adnexal structures. As used herein, the term "head and neck" will further include those intracranial structures in proximity to the aforesaid head and neck structures. These intracranial structures may include, as examples, the pituitary gland, the pineal gland, the nuclei of various cranial nerves, the intracranial extensions of the cranial nerves, the cerebellopontine angle, the arterial circle of Willis and associated vascular structures, the dura, and the meninges.

In yet other embodiments, the systems can be used in the genourinary system, such as the urethra, prostate, bladder, cervix, uterus, and anatomies in proximity thereto. As used herein, the term "genitourinary" shall include those structures of the urinary tract, the male genital system and the female genital system. The urinary tract structures include the urethra, the bladder, the ureters, the kidney and related neural, vascular, lymphatic and adnexal structures. The male genital tract includes the prostate, the seminal vesicles, the testicles, the epididymis and related neural, vascular, lymphatic, ductal and adnexal structures. The female genital tract includes the vagina, the cervix, the non-gravid and gravid uterus, the fallopian tubes, the ovaries, the ova, the fertilized egg, the embryo and the fetus. The term "genitourinary" further refers to those pelvic structures that surround or support the abovementioned structures, such as the paraurethral tissues, the urogenital diaphragm or the musculature of the pelvic floor. The devices can be configured for transurethral placement for evaluation and treatment of female urinary incontinence or bleeding and may use high resolution images of the local tissue, e.g., different layers of the paraurethral tissues. It is understood, for example, that a clearly identified disruption in the muscle layers surrounding the urethra may be repaired surgically, but also must be guided by detailed anatomic information about the site of the abnormality. The devices may also be configured for placement in the genitourinary system such as into the ureter or renal pelvis, urinary tract, or transvaginal use in analysis of the vagina and anatomies in proximity thereto. For example, transvaginal or transcervical endouterine placement may be useful in the diagnosis of neoplasia, in the diagnosis and treatment of endometriosis and in the evaluation of infertility or diagnosis, treatment of pelvic disorders resulting in pelvic pain syndromes, evaluation/treatment of cervical and uterine malignancies and to determine their stages, obstetric use such as permitting anatomic evaluation of mother and fetus.

In another embodiment, the systems can be used for evaluating and/or treating the rectum or colon, typically by the transrectal route that can be inserted through the anus to a level within the rectum, sigmoid or descending colon where the designated anatomy can be visualized. For example, this approach may be used to delineate the anatomy of the prostate gland, and may further guide the biopsy or the extirpation of lesions undertaken transrectally or transurethrally.

In other embodiments, the systems and methods of the present invention may be used for the evaluation, diagnosis or treatment of a structure in the gastrointestinal system, or for the evaluation, diagnosis or treatment of a region of the gastrointestinal anatomy. As used herein, the term "gastrointestinal" shall include structures of the digestive system including the esophagus, the stomach, the duodenum, jejunum and ileum (small intestine), the appendix and the colon. The term "gastrointestinal anatomy" shall refer to the structures of the gastrointestinal system as well as the surrounding supporting structures such as the mesentery and the enclosing structures such as the peritoneum, the diaphragm and the retroperitoneum. Disorders of the gastrointestinal system are well-known in the medical arts, as are disorders of the gastrointestinal anatomy. In an exemplary embodiment, the intrabody device may be passed into the stomach.

In other embodiments, the systems and methods of the present invention may be used for the evaluation, diagnosis and treatment of the vascular system. The vascular system is understood to include the blood vessels of the body, both arterial and venous. The vascular system includes both normal and abnormal blood vessels, named and unnamed vessels, and neovascularization. Access to the vascular system takes place using techniques familiar to practitioners of ordinary skill in the art. The present invention may be used in blood vessels of all size and the intrabody devices may be dimensionally adapted to enter smaller caliber vessels, such as those comprising the distal coronary circulation, the intracranial circulation, the circulation of the distal extremities or the distal circulation of the abdominal viscera. According to these systems and methods, furthermore, positioning a device within the vascular system may be useful for evaluating, diagnosing and treating conditions in structures adjacent to or in proximity to the particular vessel within which the device is situated. Such structures are termed "perivascular structures." As an example, a device placed within a coronary artery may provide information about the vessel itself and about the myocardium that is perfused by the vessel or that is adjacent to the vessel. A device thus positioned may be able to guide therapeutic interventions directed to the myocardial tissue, and may also be able to guide endovascular or extravascular manipulations directed to the vessel itself. It will be readily appreciated by those of ordinary skill in the art that a number of other applications exist or may be discovered with no more than routine experimentation using the systems and methods of the present invention within the vascular system.

It is understood that access to anatomic structures using the systems, devices modified to fit the intended purpose and anatomy, and methods of the present invention may be provided via naturally occurring anatomic orifices or lumens, as indicated in the examples above. It is further understood, however, that access to anatomic structures using these systems and methods may be additionally provided using temporary or permanent orifices that have been created medically.

Further, the methods and systems may cooperate with robotic driven systems rather than manual systems.

Ablation Catheter

Referring to FIGS. 31-46, a flexible (steerable) ablation catheter 80 for use in MRI-guided ablation procedures, according to some embodiments of the present invention, is illustrated. The ablation catheter 80 includes an elongated flexible housing or shaft 402 having at least one lumen 404 (FIG. 34) therethrough and includes opposite distal and proximal end portions 406, 408, respectively. The distal end portion 406 includes an ablation tip 410 having an ablation electrode 410e (FIG. 33) for ablating target tissue. A pair of RF tracking coils individually identified as 412, 414, and which are equivalent to coils 82c of FIGS. 2-3, are positioned upstream from the ablation tip 410, as illustrated. The ablation tip 410 can include a second electrode for sensing local electrical signals or properties, or the ablation electrode 410e can be bipolar and both ablate and sense.

The proximal end portion 408 of the catheter 80 is operably secured to a handle 440. The catheter shaft 402 is formed from flexible, bio-compatible and MRI-compatible material, such as, for example, polyester or other polymeric materials. However, various other types of materials may be utilized to form the catheter shaft 402, and embodiments of the present invention are not limited to the use of any particular material. In some embodiments, the shaft proximal end portion 408 is formed from material that is stiffer than the distal end portion 406. The proximal end may be stiffer than a medial portion between the distal and proximal end portions 406, 408.

The catheter 80 can be configured to reduce the likelihood of undesired heating caused by deposition of current or voltage in tissue. The catheter 80 can include RF chokes such as a series of axially spaced apart Balun circuits or other suitable circuit configurations. See, e.g., U.S. Pat. No. 6,284,971 for additional description of RF inhibiting coaxial cable that can inhibit RF induced current.

Figure 31:
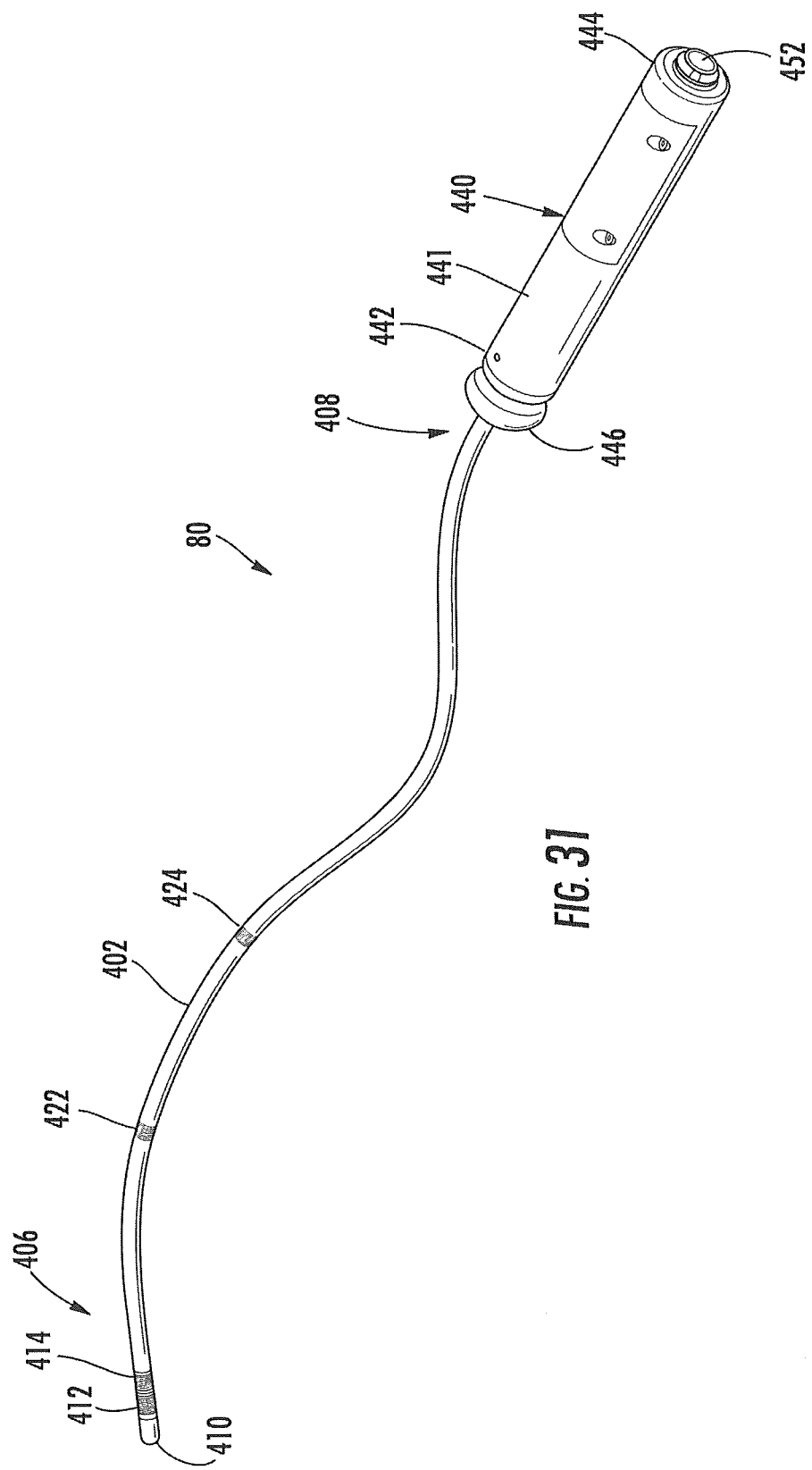
FIG. 31 is a perspective view of an exemplary ablation catheter, according to some embodiments of the present invention.
Figure 32A:
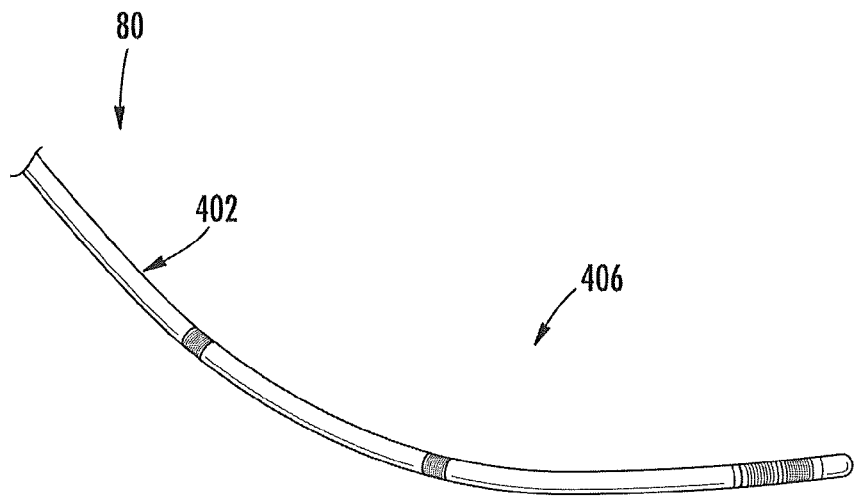
FIG. 32A is a partial perspective view of the distal end portion of the ablation catheter of FIG. 31.
Figure 32B:
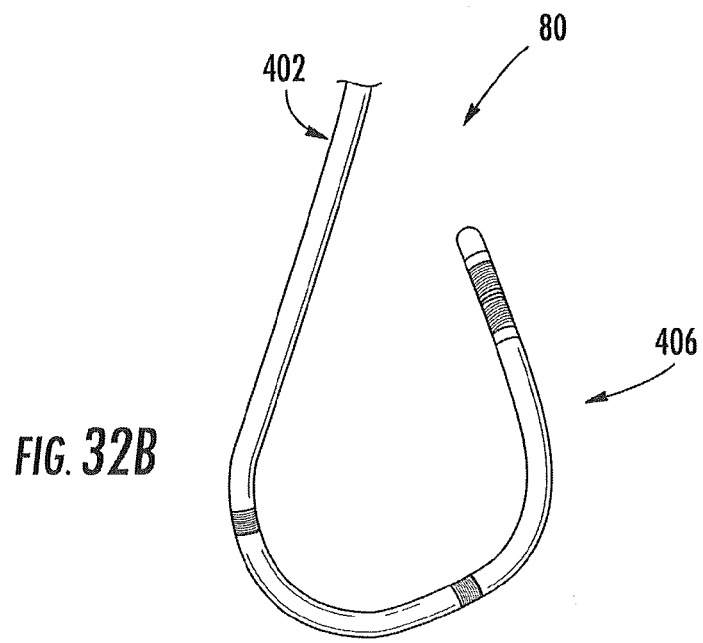
FIG. 32B illustrates the distal end portion of the ablation catheter of FIG. 31 in an articulated configuration, according to some embodiments of the present invention.

FIGS. 32A and 32B illustrate the distal end portion 406 of the ablation catheter 80 of FIG. 31 in a substantially elongated configuration (FIG. 32A) and in an articulated and/or curvilinear configuration (FIG. 32B), respectively. The ability to articulate and/or bend and/or deform the distal end portion 406 facilitates positioning the ablation tip 410 at desired locations (e.g., within a heart) during an ablation procedure. The term "articulation", as used herein, is intended to include all ways that the ablation tip portion 410 can be moved or modified or shaped (e.g., curvilinear movement, deforming movement, etc.).

In the illustrated embodiment, articulation of the distal end portion 406 is achieved by movement of a pull wire 436 (FIG. 37) disposed within the catheter shaft 402. Movement of the pull wire 436 is accomplished via the handle 440 at the catheter proximal end portion 408, as will be described below. The handle 440 serves as an actuator in conjunction with the pull wire 436 to articulate the distal end portion 406. Various types of actuators may be utilized (e.g., levers, pistons, thumb sliders, knobs, etc.). Embodiments of the present invention are not limited to the illustrated handle and pull wire actuator.

Figure 33:
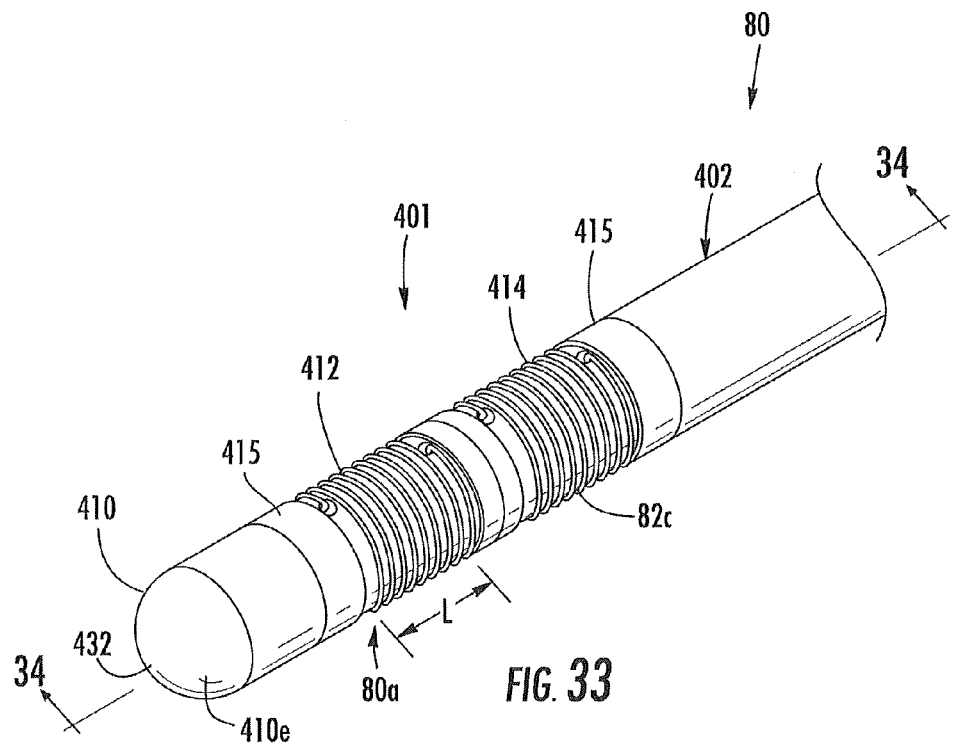
FIG. 33 is an enlarged partial perspective view of the tip portion of the ablation catheter of FIG. 31, according to some embodiments of the present invention.
Figure 43:
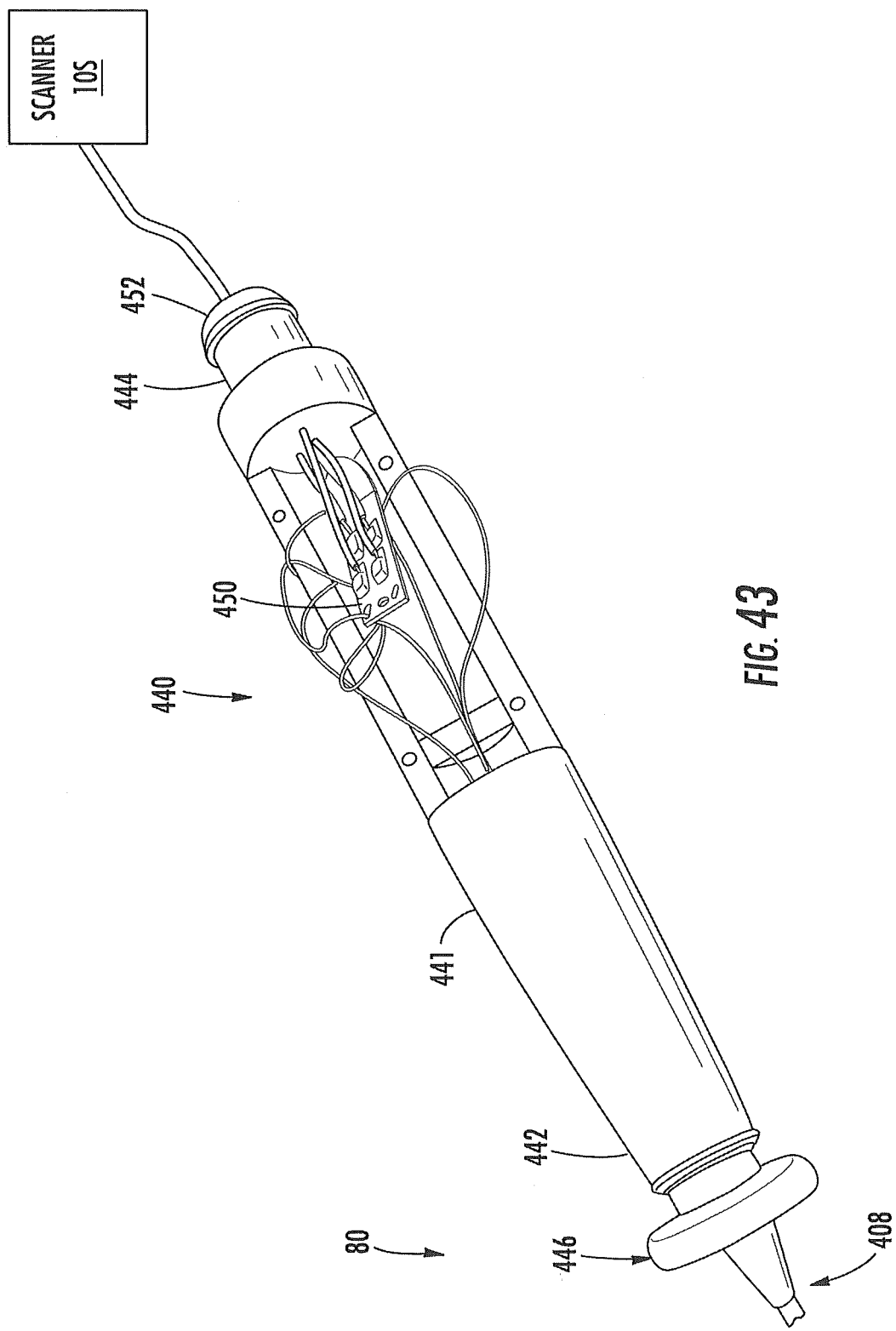
FIG. 43 is a perspective view of the handle at the proximal end of the ablation catheter of FIG. 31, according to some embodiments of the present invention, and with a cover removed.

FIG. 33 is an enlarged partial perspective view of the distal end portion 406 of the ablation catheter 80 of FIG. 31. The distal end portion 406 has an ablation tip 410 and typically at least two RF tracking coils 412, 414. The RF tracking coils 412, 414 are positioned upstream and adjacent the ablation tip 410 in spaced-apart relationship. The RF tracking coils 412, 414 are each electrically connected to a respective channel of an MRI scanner for tracking the location of the catheter 80 in 3-D space, via respective cables (e.g., coaxial cables) 416, 418 (FIG. 34) extending longitudinally through the catheter shaft lumen 404 and terminating at an electrical connector interface 450 in the handle 440 (FIG. 43). In the illustrated embodiment of FIG. 33, the RF tracking coils 412, 414 are supported within respective coil holders 415 that are secured to the catheter shaft 402, as illustrated. The RF tracking coils 412, 414 can be closely spaced and, in some embodiments, may be within about 12 mm from the ablation tip 410. In some embodiments, the RF tracking coils 412, 414 may each have about 2-16 turns and may have a length L in the longitudinal direction of the catheter shaft 402 of between about 0.25 mm and about 4 mm. Embodiments of the present invention are not limited to the two illustrated RF tracking coils 412, 414. RF tracking coils with other turns and longitudinal lengths may be used. In addition, one or more than two RF tracking coils (e.g., 1, 3, 4, etc.) may be located at distal end portion 406, according to other embodiments of the present invention.

Figure 34:
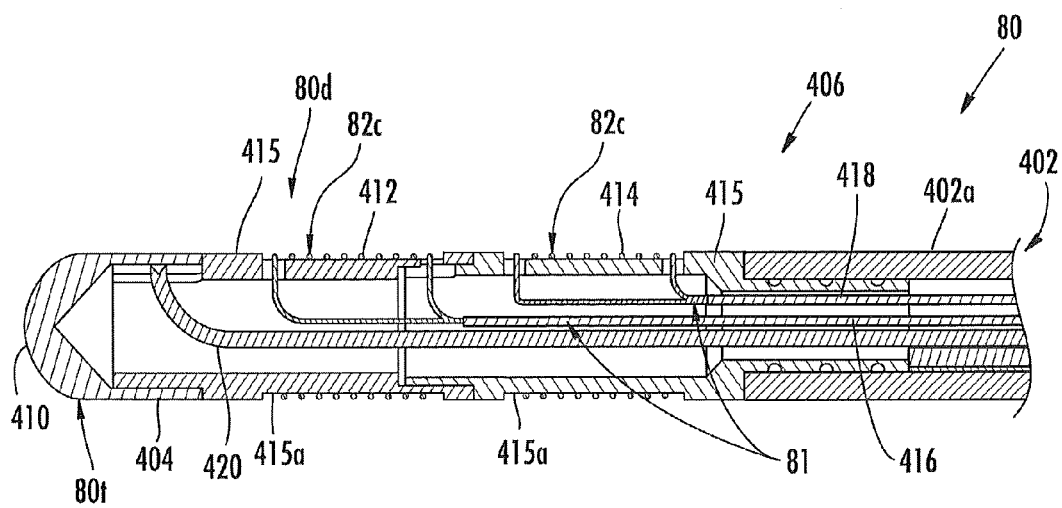
FIG. 34 is a cross-sectional view of the tip portion of the ablation catheter of FIG. 31 taken along lines 34-34.

As shown, for example in FIG. 34, each coil holder 415 has a respective recessed portion 415a within which a respective RF tracking coil 412, 414 is disposed. Each recessed portion 415a has a radial depth such that each respective coil 412, 414 is recessed slightly with respect to the outer surface 402a of the catheter shaft 402. In other embodiments, each recessed portion 415a may have a radial depth such that each respective coil is substantially flush with the outer surface 402a of the catheter shaft 402. In other embodiments, the RF tracking coils 412, 414 may be embedded within the shaft 402. Tracking coil 412 may be referred to as the tip distal coil and tracking coil 414 may be referred to as the tip proximal coil. In some embodiments, the tracking coils 412, 414 may be covered with a layer of material (not shown). For example, a layer of polymeric material, epoxy, etc. may be utilized. Each coil 412, 414 may be recessed within each respective coil holder 415 such that the layer of material overlying the coils 412, 414 is substantially flush with the outer surface 402a of the catheter 80.

In the illustrated embodiment, the ablation tip 410 includes an electrode 410e that is connected to an RF wire 420 that extends longitudinally within the lumen 404 to the electrical connector interface 450 (FIG. 44) within the handle 440 and that connects the ablation electrode 410e to an RF generator. The RF ablation electrode 410e is formed from a conductive material capable of receiving RF energy and ablating tissue. Exemplary materials include copper, as well as bio-compatible materials such as platinum, etc. In other embodiments, the ablation tip 410 may include a cryogenic ablation electrode/device configured to cryogenically ablate tissue. For example, the ablation catheter 80 can also or alternatively be configured to apply other ablation energies including cryogenic (e.g., cryoablation), laser, microwave, and even chemical ablation. In some embodiments, the ablation can be carried out using ultrasound energy. In particular embodiments, the ablation may be carried out using HIFU (High Intensity Focused Ultrasound). When MRI is used this is sometimes called Magnetic Resonance-guided Focused Ultrasound, often shortened to MRgFUS. This type of energy using a catheter to direct the energy to the target cardiac tissue can heat the tissue to cause necrosis.

The conductors 81 and/or RF wire 420 can include a series of back and forth segments (e.g., it can turn on itself in a lengthwise direction a number of times along its length), include stacked windings and/or include high impedance circuits. See, e.g., U.S. patent application Ser. Nos. 11/417,594; 12/047,832; and 12/090,583, the contents of which are hereby incorporated by reference as if recited in full herein. The conductors (e.g., coaxial cables) 81 and/or RF wire 420 can be co-wound and/or configured as back and forth stacked segments for a portion or all of their length.

Referring to FIG. 35, the catheter distal end portion 406 of the ablation catheter 80 can include a second pair of RF tracking coils 422, 424 in spaced apart relationship, as illustrated. The illustrated RF tracking coils 422, 424 are disposed within recessed portions 402b of the catheter shaft 402. Each recessed portion 402b has a radial depth such that each respective RF tracking coil 422, 424 is recessed slightly with respect to the outer surface 402a of the catheter shaft 402. In some embodiments, however, each recessed portion 402b may have a radial depth such that each respective RF tracking coil 422, 424 is substantially flush with the outer surface 402a of the catheter shaft 402. In other embodiments, the RF tracking coils 422, 424 may be embedded within the shaft 402. Each illustrated RF tracking coil 422, 424 is connected to a respective coaxial cable 426, 428 (FIG. 38) that extends longitudinally within the lumen 404 to the electrical connector interface 450 (FIG. 43) within the handle 440.

In some embodiments, the tracking coils 422, 424 may be covered with a layer of material (not shown). For example, a sleeve or layer of polymeric material, epoxy, etc. may be utilized. Each coil 422, 424 may be recessed within the catheter shaft 402 such that the layer of material overlying the coils 422, 424 is substantially flush with the outer surface 402a of the catheter 80. In some embodiments, as illustrated in FIG. 53, all four RF tracking coils 412, 414, 422, 424 may be covered with a sleeve or layer of material 480, such as a sleeve of heat shrink material having a thickness of about 0.003 inches.

Figure 38:
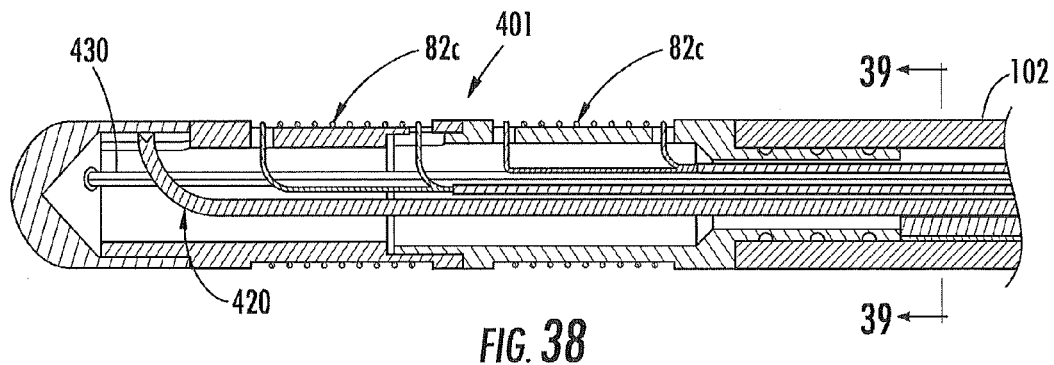
FIG. 38 is a cross-sectional view of the ablation catheter of FIG. 35 taken along lines 38-38.

Referring to FIG. 38, in some embodiments of the present invention the catheter 80 includes a thermocouple 430 that has a lead that extends longitudinally within the shaft lumen 404 from the ablation tip 410 to the electrical connector interface 450. The thermocouple 430 is configured to measure temperature of at and/or adjacent to the ablation tip 410. The thermocouple 430 can be configured to allow temperature to be monitored during ablation and/or at other times.

In some embodiments, the ablation tip 410 is provided with one or more exit ports 432 (FIG. 33) in communication with a fluid channel through which a fluid/solution, such as saline, can flow before, during, and/or after the ablation of tissue. Fluid/solution is provided to the one or more exit ports 432 via an irrigation lumen 434 that extends longitudinally through the catheter shaft lumen 404 from the exit port(s) 432 to the handle 440. The irrigation lumen 434 is in fluid communication with a fluid/solution source at the proximal end portion 408 of the catheter shaft, typically at the handle 440. The fluid/solution can provide coolant and/or improve tissue coupling with the ablation tip 410.

In some embodiments, as noted above, a pull wire 436 (FIG. 38) extends longitudinally within the catheter shaft lumen 404 from the distal end portion 406 to the handle 440 at the catheter proximal end portion 408. The pull wire 436 can extend longitudinally within a sleeve 438 that is attached to the internal wall 404a of the lumen 404. The pull wire 436 is attached to the sleeve 438 near the distal end portion 406 of the catheter 80 and otherwise is slidably disposed within the sleeve. Pulling the pull wire 436 in a direction towards the handle 440 causes the distal end portion 406 of the catheter to articulate in one direction. Pushing the pull wire 436 in the opposite direction away from the handle 440 causes the distal end portion 406 to articulate in another different direction. In some embodiments, the distal end portion 406 may include a biasing member, such as a spring, for returning the articulated distal end portion 406 to a non-articulated position.

The pull wire 436 may comprise various non-metallic materials including, but not limited to, non-metallic wires, cables, braided wires, etc. In some embodiments a monofilament wire may be utilized. In other embodiments, a multi-filament wire and/or a braided wire may be utilized. Exemplary filament materials may include, but are not limited to, Kevlar® filaments and Aramid® filaments.

Figure 37:
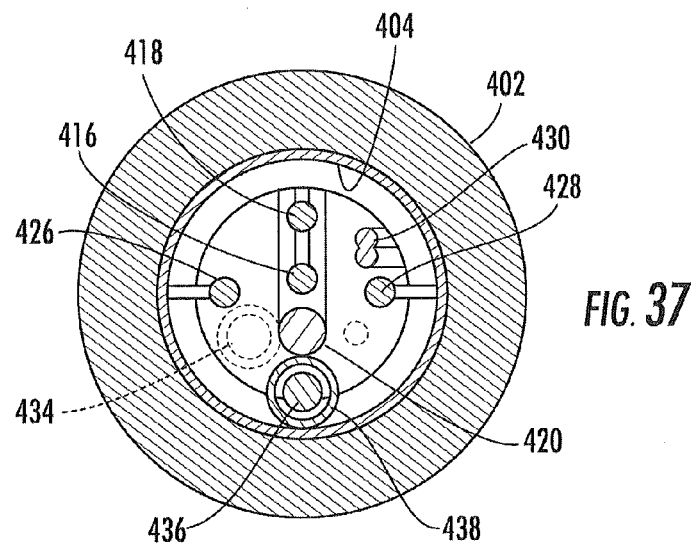
FIG. 37 is a cross-sectional view of the ablation catheter of FIG. 35 taken along lines 37-37.
Figure 39:
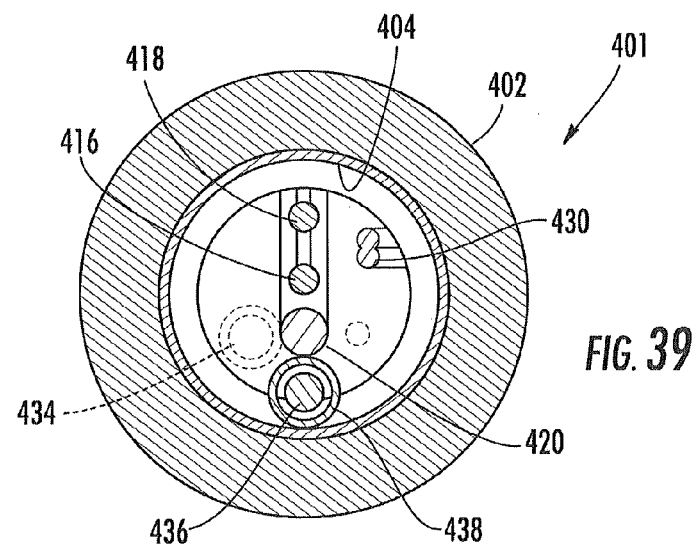
FIG. 39 is a cross-sectional view of the ablation catheter of FIG. 38 taken along lines 39-39.

FIGS. 37 and 39 are cross sectional views of the distal end portion 406 of the illustrated catheter 80. FIG. 37 is a cross sectional view taken along lines 37-37 in FIG. 35 and illustrates the location and configuration of the coaxial cables 416, 418, 426 and 428 which are connected to the RF tracking coils 412, 414, 422 and 424, respectively. FIG. 37 also illustrates the location and configuration of an RF wire 420 that is connected to the ablation tip 410 and that provides RF energy to the ablation electrode 410e. FIG. 37 also illustrates the location of the thermocouple 430, and the location of an irrigation lumen 434. FIG. 39 is a cross sectional view taken along lines 30-30 in FIG. 38 and illustrates the location and configuration of the coaxial cables 416, 418 which are connected to the RF tracking coils 412, 414. FIG. 39 also illustrates the location and configuration of the RF wire 420 connected to the ablation electrode 410e, the location of thermocouple 430, and the location of irrigation lumen 434.

Figure 40:
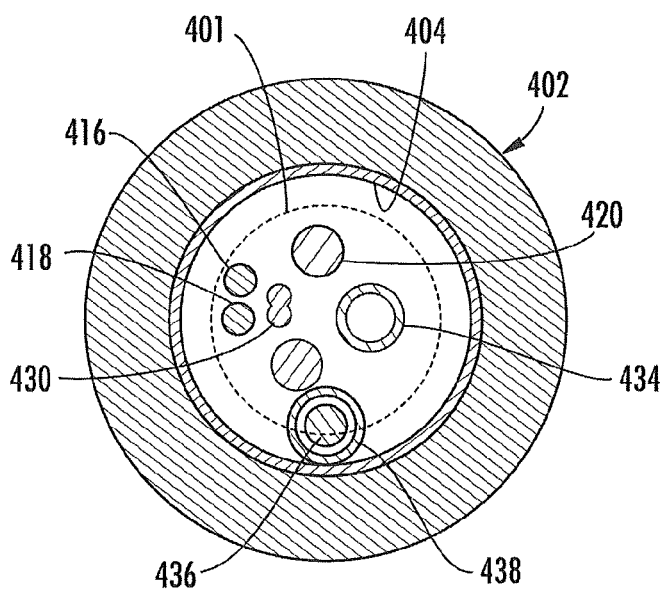
FIG. 40 is a cross-sectional view of the ablation catheter of FIG. 38 at the same location as the cross-sectional view of FIG. 39 and that illustrates an exemplary internal diameter of free space available inside the tip assembly, according to some embodiments of the present invention.
Figure 41:
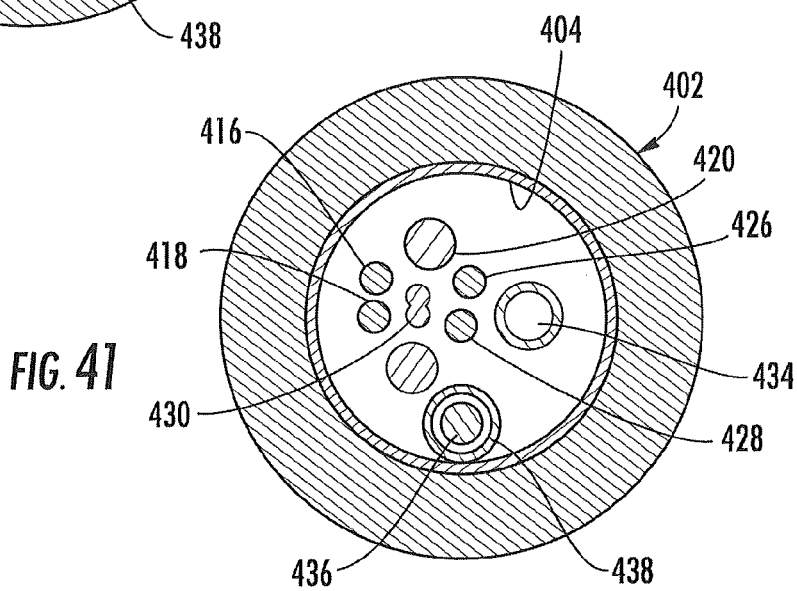
FIG. 41 is a cross-sectional view of the ablation catheter of FIG. 35 at the same location as the cross-sectional view of FIG. 37 and that illustrates an exemplary internal diameter and wires/components inside the catheter shaft lumen, according to some embodiments of the present invention.
Figure 42:
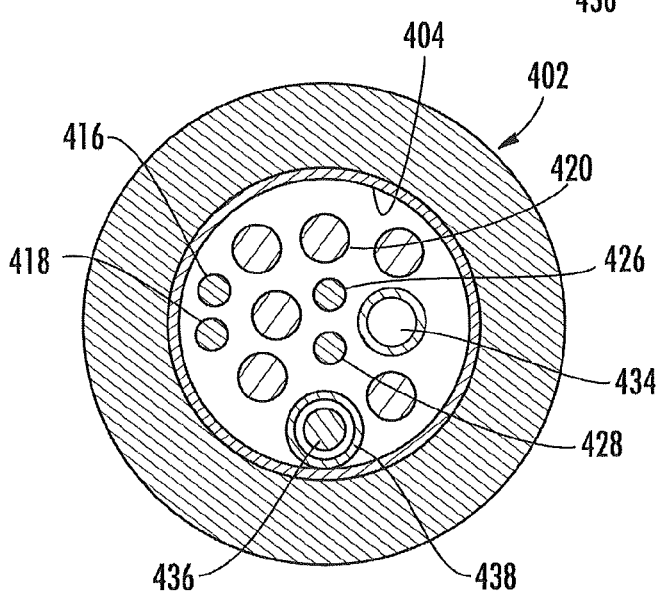
FIG. 42 is a cross-sectional view of the ablation catheter of FIG. 35 that illustrates an exemplary number of wires that can be placed inside the catheter shaft lumen, according to some embodiments of the present invention.

FIG. 40 is a cross-sectional view of the illustrated catheter 80 at the same location as the cross-sectional view of FIG. 39 and that illustrates an exemplary diameter or free space available inside the tip assembly 401, according to some embodiments of the present invention. FIG. 40 also illustrates the respective diameters of the thermocouple 430, coaxial cables 416, 418, pull wire 436, sleeve 438, and RF wire 420. FIG. 41 is a cross-sectional view of the illustrated ablation catheter 80 at the same location as the cross-sectional view of FIG. 37 and that illustrates an exemplary diameter or free space available inside the catheter shaft lumen 404, according to some embodiments of the present invention. FIG. 41 also illustrates the respective diameters of the thermocouple 430, coaxial cables 416, 418, pull wire 436, sleeve 438, and the RF wire 420. FIG. 42 is a cross-sectional view of the illustrated catheter 80 that illustrates an exemplary number of wires that can be placed inside the catheter shaft lumen 404, according to some embodiments of the present invention.

FIG. 43 is a perspective view of the handle 440, which is connected to the proximal end portion 408 of the catheter shaft 402, according to some embodiments of the present invention. The handle 440 has a main body portion 441 with opposite distal and proximal end portions 442, 444. In FIG. 43, a cover 443 (FIG. 44) is removed from the handle main body portion 441 to illustrate the termination of the various leads extending into the handle 440 from the shaft lumen 404 at an electrical connector interface 450 (shown as PCB). Electrical connector interface 450 is electrically connected to an adapter 452 at the proximal end 444 of the handle 440. Adapter 452 is configured to receive one or more cables that connect the ablation catheter 80 to an MRI scanner 10S and that facilitate operation of the RF tracking coils 412, 414, 422, 424. Adapter 452 also is configured to connect the ablation tip 410 to an ablation source. In the illustrated embodiment, electrical connector interface 450 can also include the decoupling circuit 460, described below.

In the illustrated embodiment, the distal end portion 442 of the handle 440 includes a piston 446 that it movably secured to the handle main body portion 441 and that is movable between extended and retracted positions relative the handle main body portion 441. In FIG. 43, the piston 446 is in a retracted position. The piston 446 is connected to the pull wire 436 such that movement of the piston 446 between extended and retracted positions causes the pull wire 436 to correspondingly extend and retract and, thereby, causing articulation of the distal end portion 401 of the catheter 80.

Figure 44:
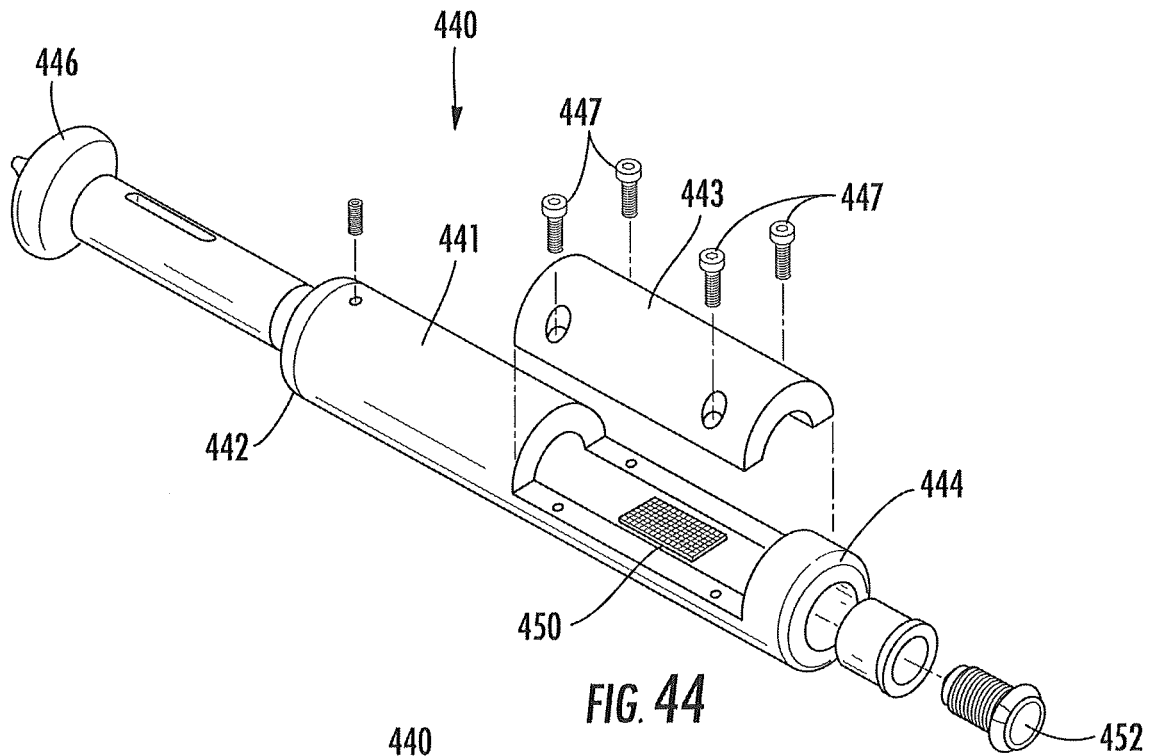
FIG. 44 is an exploded perspective view of the handle of FIG. 43.
Figure 45:
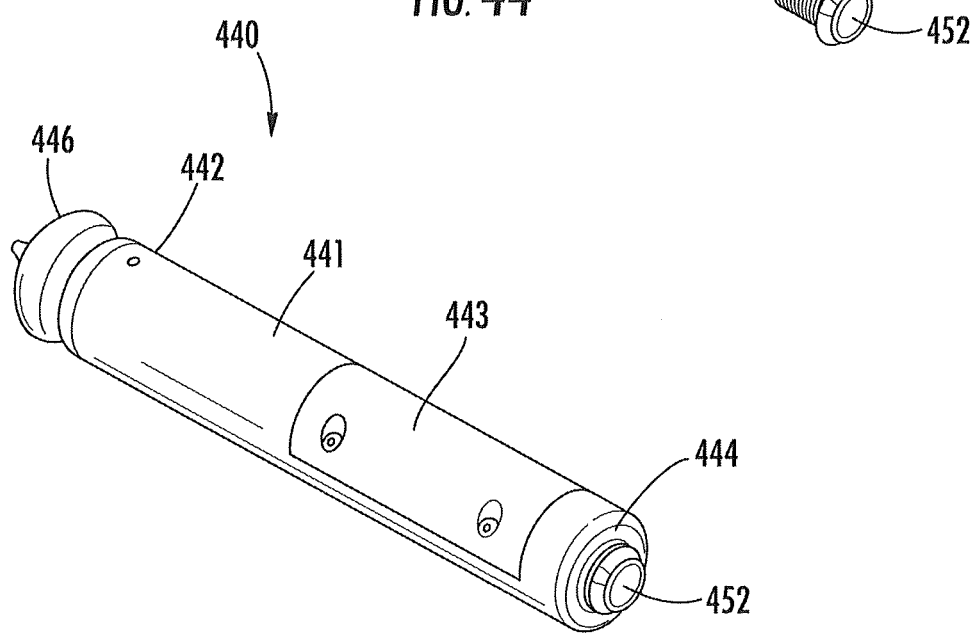
FIG. 45 illustrates the handle of FIG. 44 in an assembled configuration.

FIG. 44 is an exploded perspective view of the handle 440 of FIG. 43, according to some embodiments of the present invention. The electrical connector interface 450 is illustrated within the main body portion 441 and the adapter 452 that is electrically connected to the electrical connector interface 450 is illustrated at the handle proximal end portion 444. FIG. 45 is a perspective view of the handle 440 of FIG. 44 with the piston 446 in a retracted position and the cover 443 secured to the main body portion 441 via fasteners 447.

Figure 46:
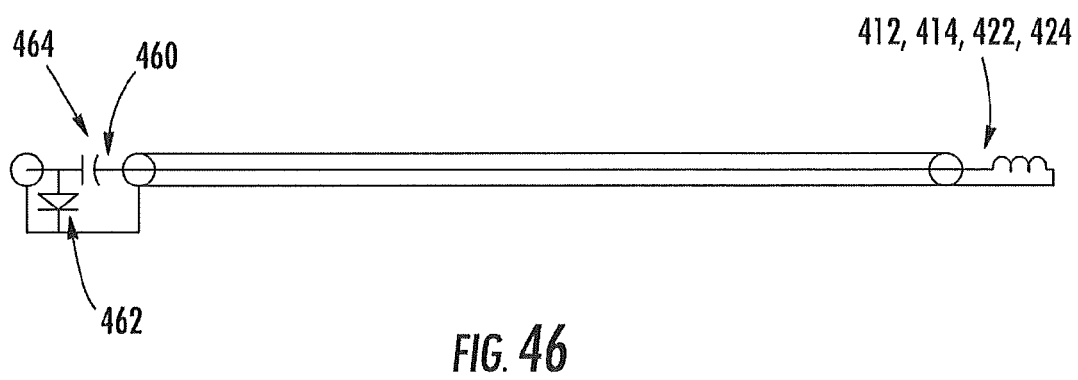
FIG. 46 is a schematic illustration of an exemplary tracking coil circuit utilized in the ablation catheter of FIG. 31, according to some embodiments of the present invention.

Referring to FIG. 46, another RF tracking coil tuning circuit 460 that may be utilized with individual MRI channels and respective RF tracking coils 412, 414, 422, 424, according to some embodiments of the present invention, is illustrated. In the illustrated embodiment, each respective coaxial cable 416, 418, 426, 428 is about a 50 ohm impedance microcoaxial cable with a length from the diode of about $\frac{3}{4}\lambda$ at about 123.3 MHz (e.g., about 45 inches). However, other cables and/or cable lengths may be utilized in accordance with embodiments of the present invention, such as $\frac{1}{4}\lambda$ lengths, or other odd harmonic/multiples of a quarter wavelength at an MRI Scanner operational frequency, etc. For each coaxial cable 416, 418, 426, 428, a respective RF tracking coil 412, 414, 422, 424 is connected at one end and the tracking coil circuit 460 is connected to the other end, as illustrated.

Figure 49:
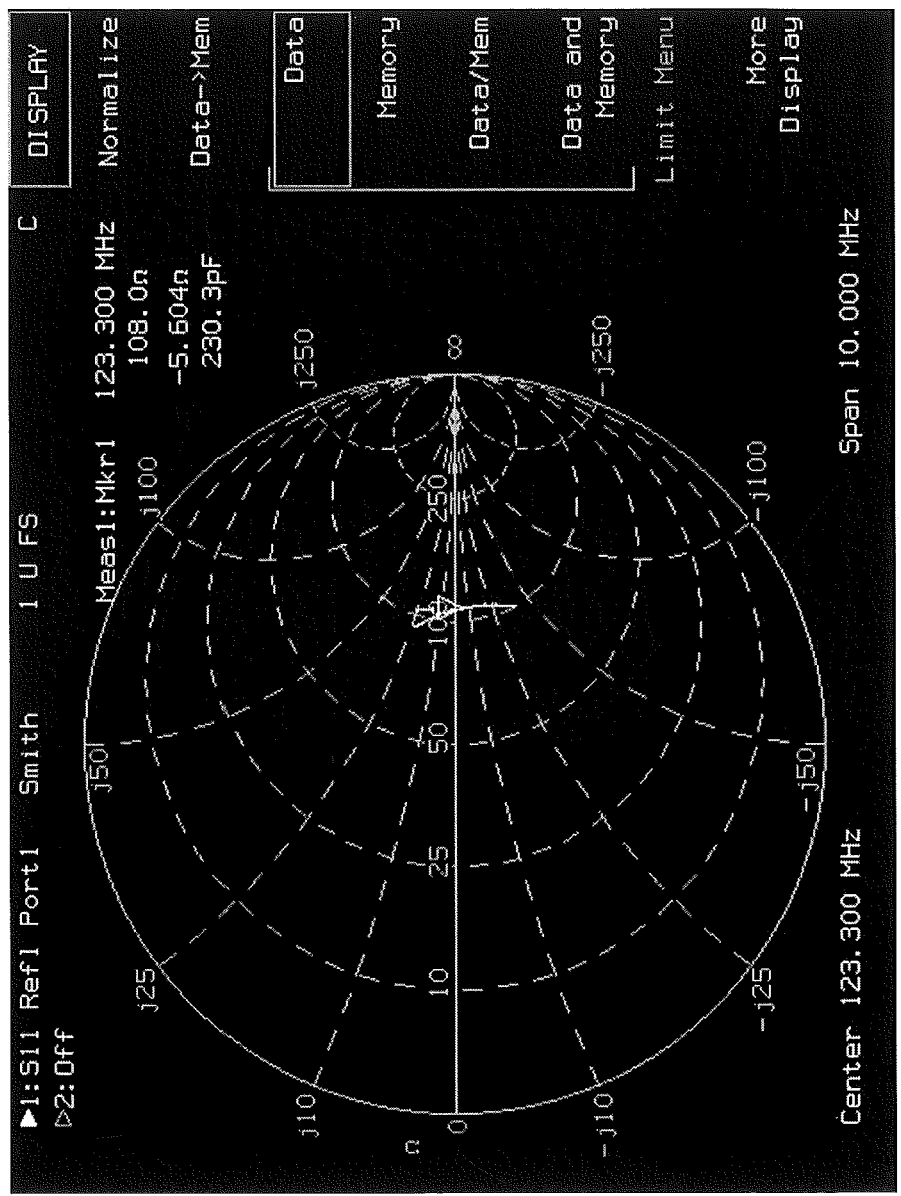
FIG. 49 is a Smith chart illustrating input impedance of a ¾λ coaxial cable shorted at one end by a PIN diode, according to some embodiments of the present invention.

Each tracking coil circuit (460, FIG. 46; 83, FIG. 4) can include a PIN diode (462, FIG. 46; UI, FIG. 4) and DC blocking capacitor 464 (FIG. 46) and is typically located within the handle 440, although in other embodiments, the tracking coil circuits 460 can be located within the catheter shaft lumen 404 closer to a medial or distal end portion (not shown). Each tracking coil circuit 460 is electrically connected to an MRI scanner, and can reduce signal noise within a respective channel caused by undesired coupling during scanner operation. In some embodiments, the tracking coil circuit 460 can produce 100 ohms impedance across an RF tracking coil when the PIN diode 462 is shorted, for example, by an MRI scanner during scanner operations, as illustrated in FIG. 49.

In some embodiments of the present invention, RF tracking coils 412, 414, 422, 424 may be between about 2-16 turn solenoid coils. However, other coil configurations may be utilized in accordance with embodiments of the present invention. Each of the RF tracking coils 412, 414, 422, 424 can have the same number of turns or a different number of turns, or different ones of the RF tracking coils 412, 414, 422, 424 can have different numbers of turns. It is believed that an RF tracking coil with between about 2-4 turns at 3.0 T provides a suitable signal for tracking purposes.

FIG. 47A illustrates an ablation catheter 80 in a 3.0 Tesla (T) MRI environment without the use of the RF tracking coil circuit 460 for each RF tracking coil (412, 414, 422, 424). The tracking coil at the tip portion (i.e., coil 412) is a 10 turn solenoid coil. Undesired coupling produced in the MRI environment by the presence of the various electronic components and wires within the catheter 80 is clearly illustrated, particularly in the vicinity of RF tracking coil 424. FIG. 47B illustrates an MRI signal strength graph 470 of the MRI image of FIG. 47A in the Z direction. The undesired coupling is clearly illustrated in the graph region 472. FIG. 47C illustrates MRI signal strength of the MRI image of FIG. 47A in the X direction.

Figure 48B:
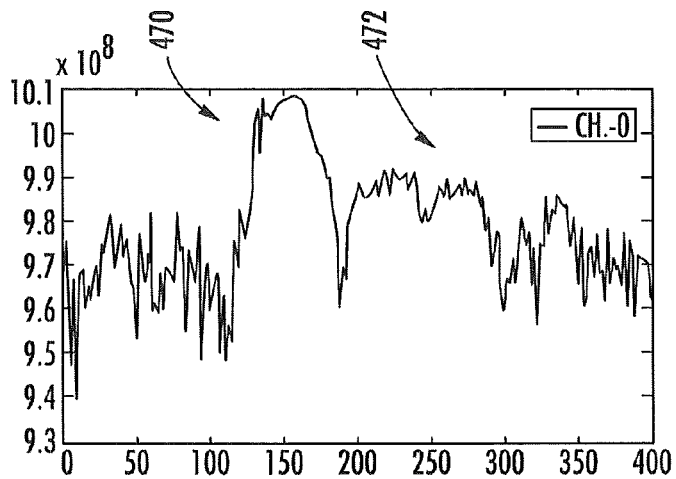
FIG. 48B illustrates MRI signal strength of the MRI image of FIG. 48A in the Z direction.
Figure 48A:
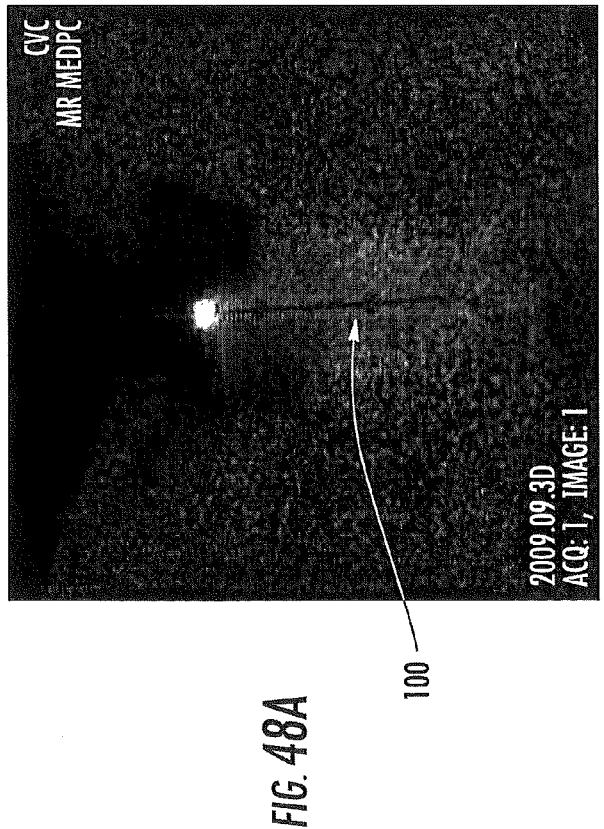
FIG. 48A is an MRI image of the ablation catheter of FIG. 31 in a 3.0 T MRI environment with the RF tracking coil circuit of FIG. 46 being utilized with respective multiple RF tracking coils, according to some embodiments of the present invention.
Figure 48C:
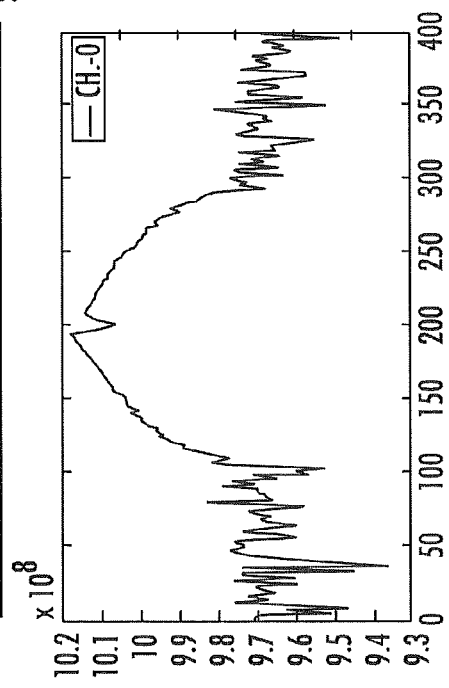
FIG. 48C illustrates MRI signal strength of the MRI image of FIG. 48A in the X direction.

FIG. 48A illustrates an ablation catheter 80 in a 3.0 T MRI environment and where the RF tracking coil tuning circuit 460 of FIG. 46 is utilized with each RF tracking coil (412, 414, 422, 424) to control and reduce undesired coupling. The tracking coil at the tip portion is a 16 turn solenoid coil. FIG. 48B illustrates MRI signal strength graph 470 of the MRI image of FIG. 48A in the Z direction. The absence of undesired coupling is clearly illustrated, both in the MRI image of FIG. 39A and in region 472 of the graph 470 of FIG. 48B. FIG. 48C illustrates MRI signal strength of the MRI image of FIG. 48A in the X direction.

Mapping Catheter

Figure 50:
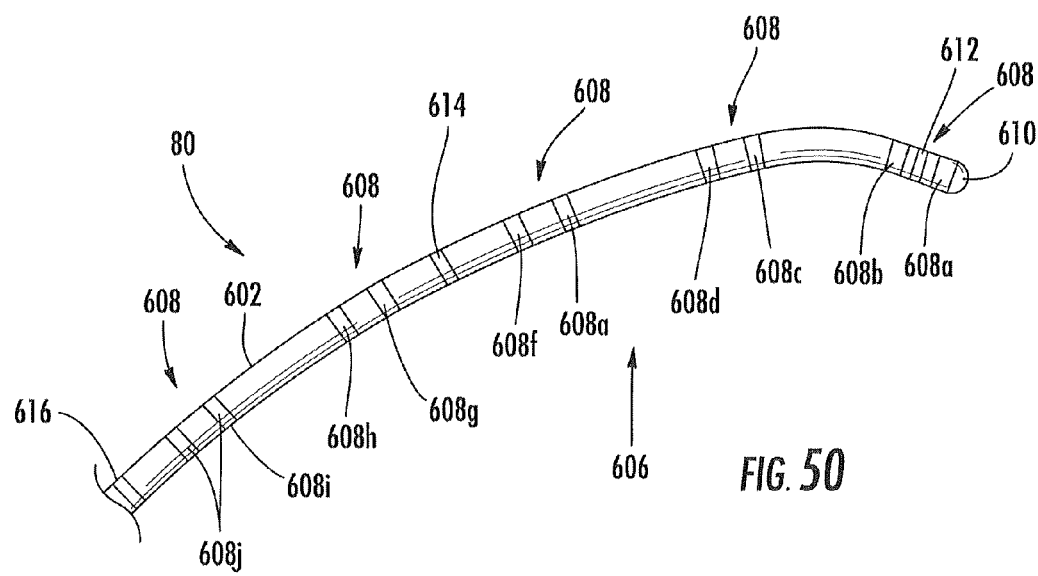
FIG. 50 is a partial perspective view of the distal end of a mapping catheter, according to some embodiments of the present invention.

Referring to FIG. 50, a flexible (steerable) mapping catheter 80 for use in MRI-guided procedures, according to some embodiments of the present invention, is illustrated. The mapping catheter 80 includes an elongated flexible housing or shaft 602 with opposite distal and proximal end portions, only the distal end portion 606 is illustrated. The distal end portion 606 includes a plurality of electrodes 608 for sensing local electrical signals or properties arranged in spaced-apart relationship, as illustrated. First and second electrodes 608a, 608b are positioned adjacent the tip 610 of the catheter 80. The remaining electrodes (608c-608d, 608e-608f, 608g-608h, 608i-608j) are positioned upstream from the first two electrodes 608a-608b, as illustrated The proximal end portion of the catheter 80 is operably secured to a handle, as is well known. The catheter shaft 602 is formed from flexible, bio-compatible and MRI-compatible material, such as polyester or other polymeric materials. However, various other types of materials may be utilized to form the catheter shaft 602, and embodiments of the present invention are not limited to the use of any particular material. In some embodiments, the shaft distal end portion 606 is formed from material that is stiffer than the proximal end portion and a medial portion between the distal and proximal end portions.

The catheter 80 can be configured to reduce the likelihood of undesired deposition of current or voltage in tissue. The catheter 80 can include RF chokes such as a series of axially spaced apart Balun circuits or other suitable circuit configurations. See, e.g., U.S. Pat. No. 6,284,971 for additional description of RF inhibiting coaxial cable that can inhibit RF induced current.

The mapping catheter 80 also includes a plurality of tracking coils 612, 614, 616 (equivalent to coils 80c, FIGS. 2-3) in spaced-apart relationship, as illustrated. Tracking coil 612 is positioned between the first pair of electrodes 608a, 608b, as illustrated. The catheter 80 can comprise coaxial cables 81 that connect the tracking coils 612, 614, 616 to an external device for tracking the location of the catheter 80 in 3-D space. The conductors 81 can include a series of back and forth segments (e.g., it can turn on itself in a lengthwise direction a number of times along its length), include stacked windings and/or include high impedance circuits. See, e.g., U.S. patent application Ser. Nos. 11/417,594; 12/047,832; and 12/090,583, the contents of which are hereby incorporated by reference as if recited in full herein. The conductors (e.g., coaxial cables) 81 can be co-wound in one direction or back and forth in stacked segments for a portion or all of their length.

Articulation of the distal end portion 606 may be achieved by movement of a pull wire (not shown), as described above with respect to the ablation catheter 80, or by another actuator in communication with the distal end portion 606, as would be understood by one skilled in the art.

The electrodes 608 can be closely spaced and, in some embodiment, may be arranged in pairs that are spaced-apart by about 2.5 mm. In some embodiments, the RF tracking coils 612, 614, 616 may each have about 2-16 turns and may have a length in the longitudinal direction of the catheter shaft 602 of between about 0.25 mm and about 4 mm. Embodiments of the present invention are not limited to the three illustrated RF tracking coils 612, 614, 616. RF tracking coils with other turns and longitudinal lengths may be used. In addition, one or more than three RF tracking coils (e.g., 1, 4, 5, etc.) may be utilized, according to other embodiments of the present invention.

Figure 51A:
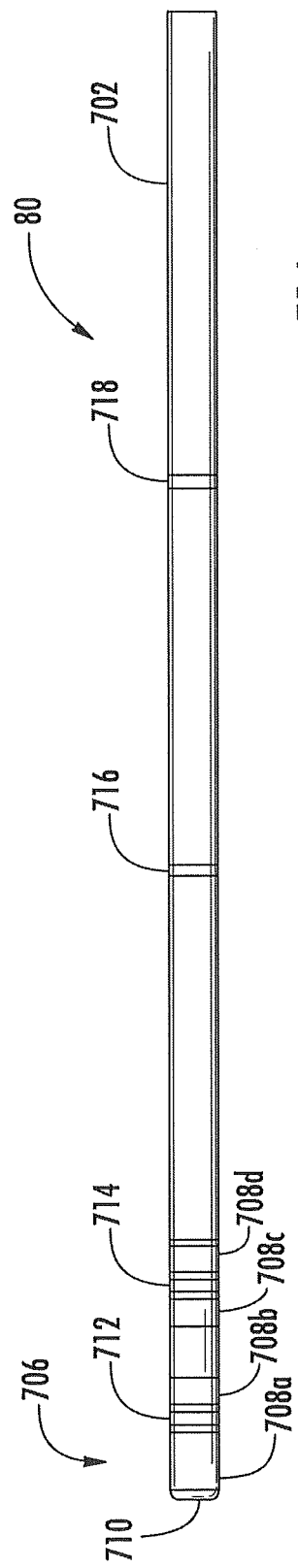
FIG. 51A is a partial side view of a distal end of an ablation catheter, according to other embodiments of the present invention.
Figure 51B:
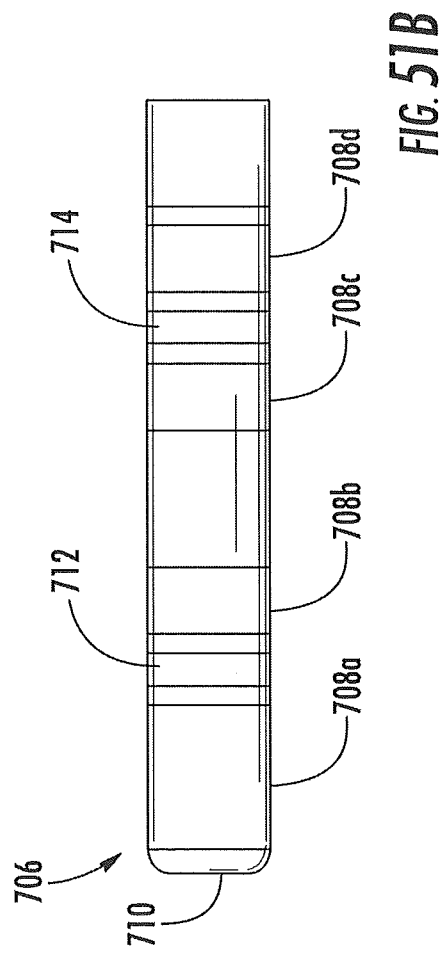
FIG. 51B and an enlarged partial view of the distal end of the ablation catheter of FIG. 51A.

Referring now to FIGS. 51A-51B, a flexible (steerable) ablation catheter 80 for use in MRI-guided procedures, according to other embodiments of the present invention, is illustrated. The illustrated ablation catheter 80 includes an elongated flexible housing or shaft 702 with opposite distal and proximal end portions, only the distal end portion 706 is illustrated. The proximal end portion of the catheter 80 is operably secured to a handle, as is well known. The catheter shaft 702 is formed from flexible, bio-compatible and MRI-compatible material, such as polyester or other polymeric materials. However, various other types of materials may be utilized to form the catheter shaft 702, and embodiments of the present invention are not limited to the use of any particular material. In some embodiments, the shaft distal end portion 706 is formed from material that is stiffer than the proximal end portion and a medial portion between the distal and proximal end portions.

The catheter 80 can be configured to reduce the likelihood of undesired deposition of current or voltage in tissue. The catheter 80 can include RF chokes such as a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current.

The distal end portion 706 includes a plurality of electrodes 708a-708d for sensing local electrical signals or properties arranged in spaced-apart relationship, as illustrated. The first electrode 708a is located adjacent to the ablation tip 710. The second electrode 708b is located approximately 5.8 mm from the ablation tip 710. The third and fourth electrodes 708c, 708d are located approximately 10.1 mm and 13 mm, respectively, from the ablation tip 710.

The illustrated ablation catheter 80 also includes a plurality of RF tracking coils 712, 714, 716, 718 (equivalent to coils 80c, FIGS. 2-3) in spaced-apart relationship. Tracking coil 712 is positioned between the first and second electrodes 608a, 608b, and tracking coil 714 is positioned between the third and fourth electrodes 608c, 608d, as illustrated. The catheter 80 can comprise coaxial cables 81 that connect the tracking coils 712, 714, 716, 718 to an external device for tracking the location of the catheter 80 in 3-D space. The conductors 81 can include a series of back and forth segments (e.g., it can turn on itself in a lengthwise direction a number of times along its length), include stacked windings and/or include high impedance circuits. See, e.g., U.S. patent application Ser. Nos. 11/417,594; 12/047,832; and 12/090,583. The conductors (e.g., coaxial cables) 81 can be co-wound in one direction or back and forth in stacked segments for a portion or all of their length.

Articulation of the distal end portion 706 may be achieved by movement of a pull wire (not shown), as described above, or by another actuator in communication with the distal end portion 706, as would be understood by one skilled in the art.

Referring now to FIGS. 52A-52C, a flexible (steerable) mapping catheter 80 for use in MRI-guided procedures, according to other embodiments of the present invention, is illustrated. The illustrated catheter 80 is a "loop" catheter and includes an elongated flexible housing or shaft 802 with opposite distal and proximal end portions, only the distal end portion 806 is illustrated. The proximal end portion of the catheter 80 is operably secured to a handle, as is well known. The catheter shaft 802 is formed from flexible, bio-compatible and MRI-compatible material, such as polyester or other polymeric materials. However, various other types of materials may be utilized to form the catheter shaft 802, and embodiments of the present invention are not limited to the use of any particular material. In some embodiments, the shaft distal end portion 806 is formed from material that is stiffer than the proximal end portion and a medial portion between the distal and proximal end portions.

The catheter 80 can be configured to reduce the likelihood of undesired deposition of current or voltage in tissue. The catheter 80 can include RF chokes such as a series of axially spaced apart Balun circuits or other suitable circuit configurations. See, e.g., U.S. Pat. No. 6,284,971, for additional description of RF inhibiting coaxial cable that can inhibit RF induced current.

The distal end portion 806 is articulable to a "loop" shape, as illustrated and includes a plurality of RF tracking coils 812, 814, 816, 818, 820 (equivalent to coils 80c, FIGS. 2-3) in spaced-apart relationship. The catheter 80 can comprise coaxial cables 81 that connect the tracking coils 812, 814, 816, 818, 820 to an external device for tracking the location of the catheter 80 in 3-D space. The conductors 81 can include a series of back and forth segments (e.g., it can turn on itself in a lengthwise direction a number of times along its length), include stacked windings and/or include high impedance circuits. See, e.g., U.S. patent application Ser. Nos. 11/417,594; 12/047,832; and 12/090,583. The conductors (e.g., coaxial cables) 81 can be co-wound in one direction or back and forth in stacked segments for a portion or all of their length.

Articulation of the distal end portion 806 may be achieved by movement of a pull wire (not shown), as described above, or by another actuator in communication with the distal end portion 806, as would be understood by one skilled in the art.

Figure 54A:
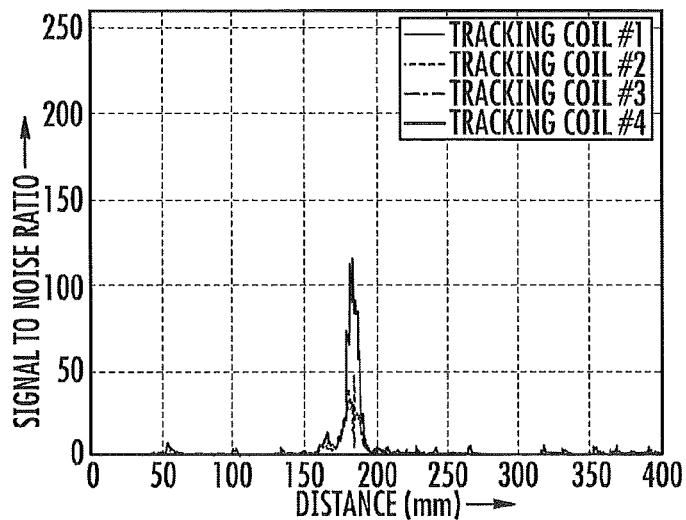
FIGS. 54A-54C are plots of signal to noise ratio to distance for X axis, Y axis, and Z axis projections, respectively, for a four tracking coil catheter, according to some embodiments of the present invention, and wherein each coil has two turns.
Figure 54B:
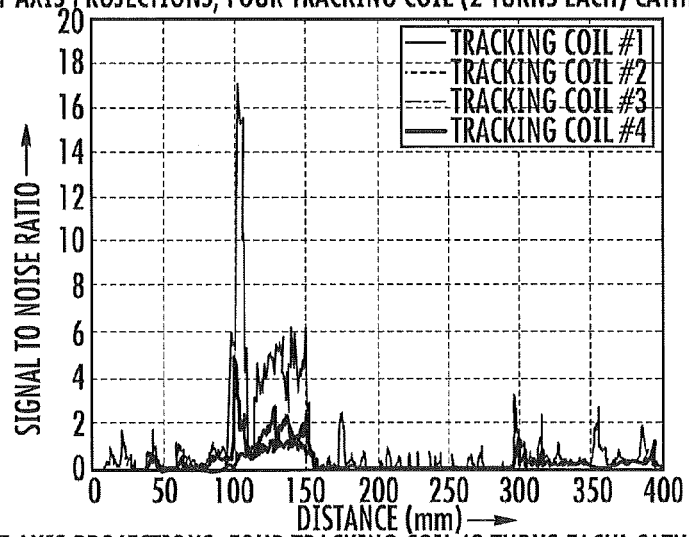
Figure 54C:
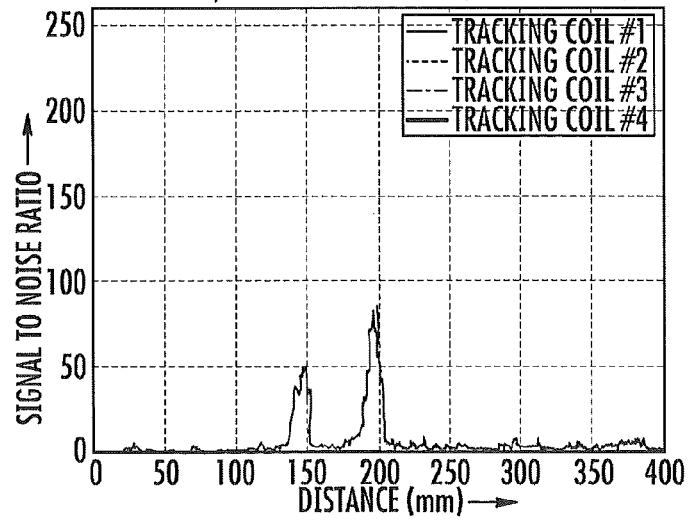
Figure 55A:
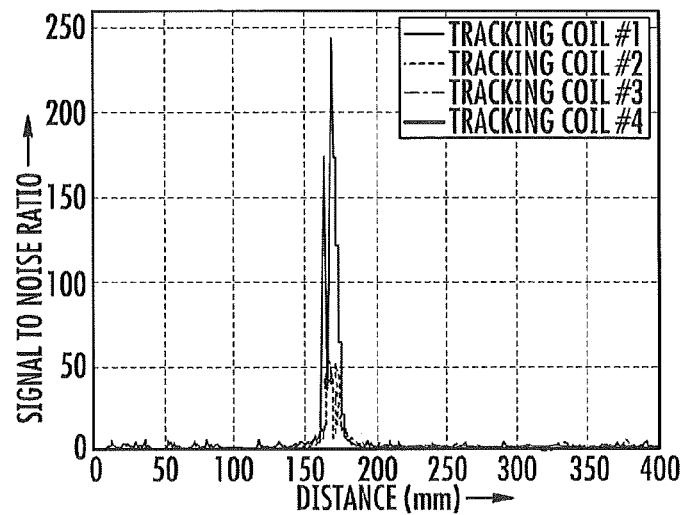
FIGS. 55A-55C are plots of signal to noise ratio to distance for X axis, Y axis, and Z axis projections, respectively, for a four tracking coil catheter, according to some embodiments of the present invention, and wherein each coil has four turns.
Figure 55B:
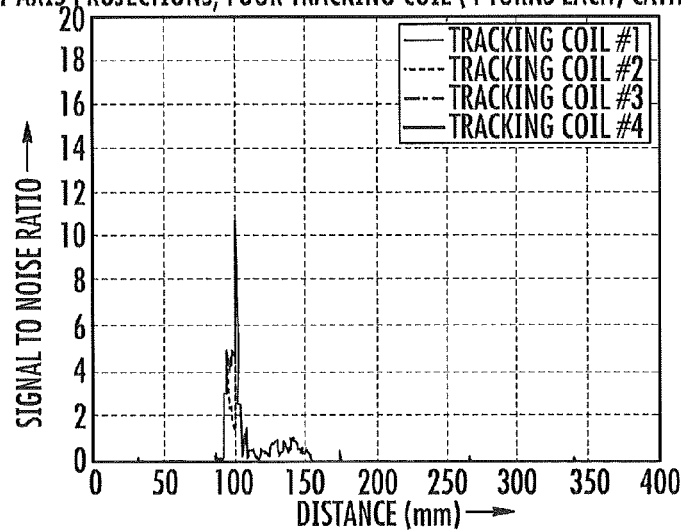
Figure 55C:
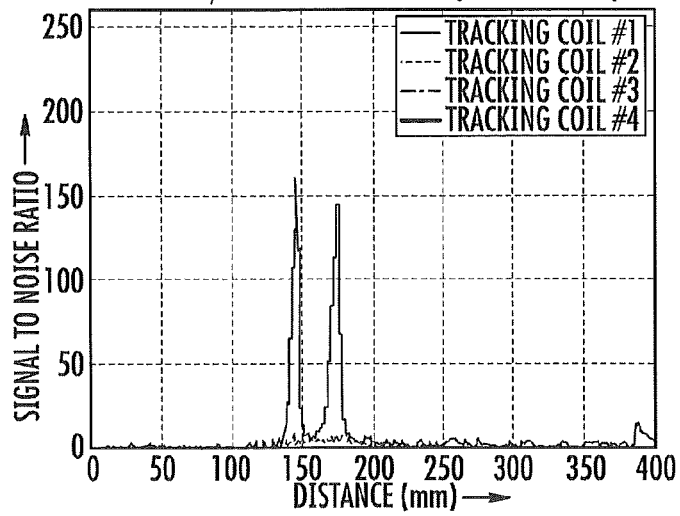
Figures 56, 57A:
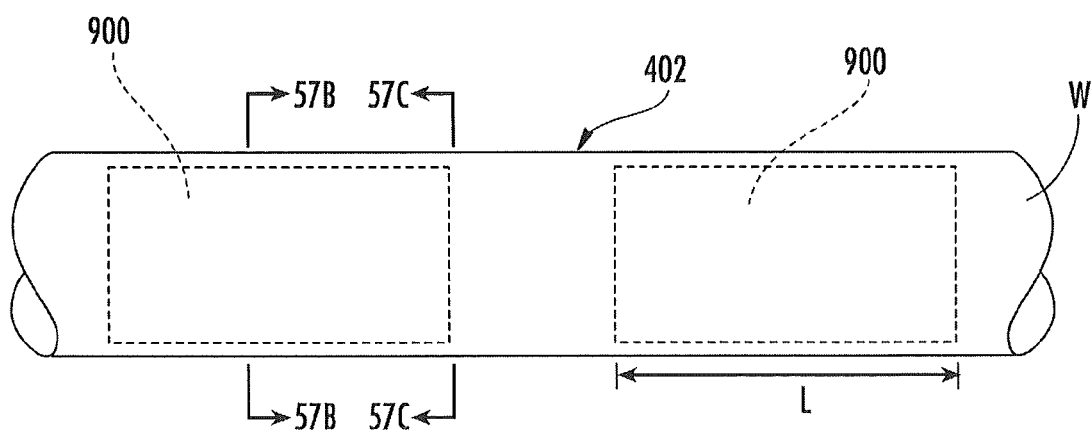
FIG. 56 is a table comparing signal to noise ration for the catheters of FIGS. 54A-54C and 55A-55C.
FIG. 57A is a partial side view of the sheath of the device of FIG. 31 including multiple RF shields in end-to-end spaced-apart relationship, according to some embodiments of the present invention.

FIGS. 54A-54C are plots of signal to noise ratio to distance for X axis, Y axis, and Z axis projections, respectively, for a four tracking coil catheter, according to some embodiments of the present invention, and wherein each coil has two turns. FIGS. 55A-55C are plots of signal to noise ratio to distance for X axis, Y axis, and Z axis projections, respectively, for a four tracking coil catheter, according to some embodiments of the present invention, and wherein each coil has four turns. FIG. 56 is a table comparing signal to noise ration for the catheters of FIGS. 54A-54C and 55A-55C. The plots of FIGS. 54A-54C and 55A-55C illustrate the viability of miniature RF tracking coils having only 2 turns and 4 turns, respectively. These plots show the significance of how effective the circuits (83, FIG. 4; 460, FIG. 46) are.

Figure 57B:
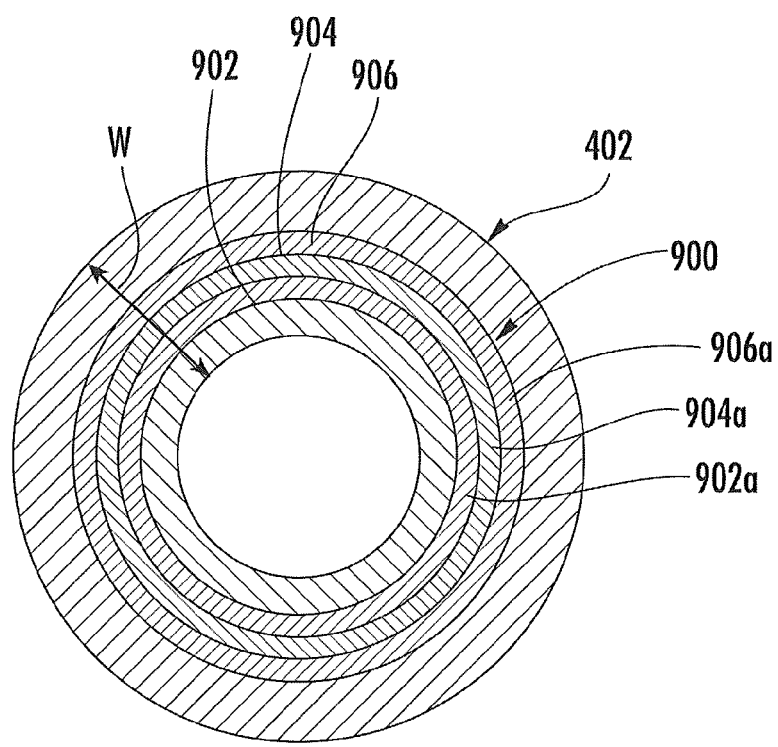
FIG. 57B is a cross-sectional view of the sheath of FIG. 57A taken along line 57B-57B.
Figure 57C:
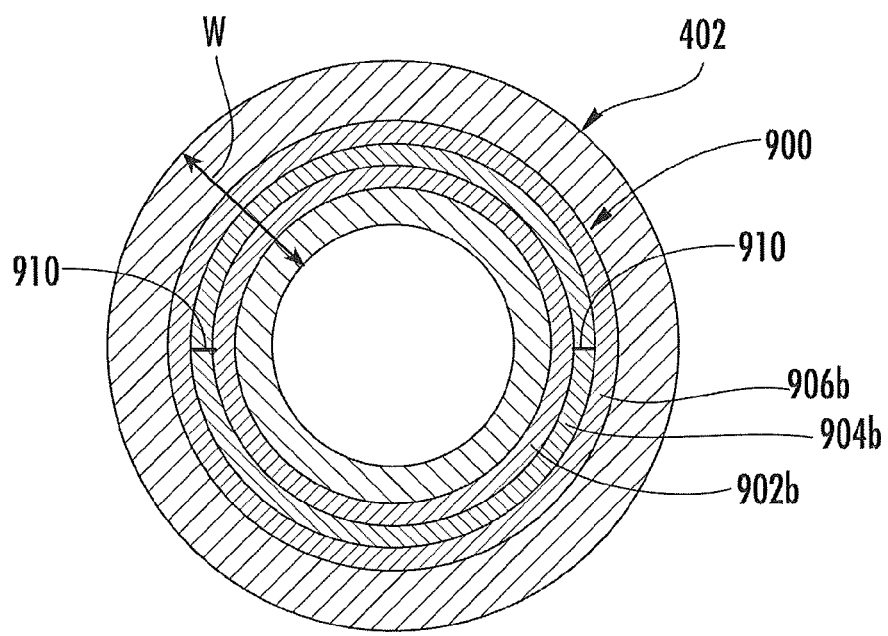
FIG. 57C is a cross-sectional view of the sheath of FIG. 57A taken along line 57C-57C.

Referring now to FIGS. 57A-57C, the shaft 402 of the ablation catheter 80 of FIGS. 31-46 may include a plurality of RF shields 900 coaxially disposed within the wall W of the shaft 402 in end-to-end spaced-apart relationship. The RF shields 900 may be utilized with any of the catheters described herein, including the catheters of FIGS. 50, 51A-51B, 52A-52C. The RF shields 900 are configured to impede RF coupling along the shaft 402 when exposed to an MRI environment. Although a pair of RF shields 900 are illustrated in FIG. 57A, it is understood that many additional RF shields 900 may be coaxially disposed within the elongated sheath wall W in end-to-end spaced-apart relationship. Only two RF shields 900 are shown for ease of illustration.

As more clearly shown in FIGS. 57B-57C, each RF shield 900 includes an elongated inner tubular conductor 902 having opposite end portions 902a, 902b, an elongated dielectric layer 904 that coaxially surrounds the inner conductor 902, and an elongated outer tubular conductor 906 that coaxially surrounds the dielectric layer 904 and has opposite end portions 906a, 906b. The inner and outer tubular conductors 902, 906 are electrically connected to each other at only one of the end portions. The opposite respective end portions are electrically isolated. In the illustrated embodiment, the inner and outer tubular conductors 902, 906 are electrically connected to each other via jumper wires 910 at adjacent end portions 902b, 906b (FIG. 57C).

In some embodiments, the inner and outer conductors can be formed as thin-film foil layers of conductive material on opposite sides of a thin film insulator (e.g., a laminated, thin flexible body).

The RF shields 900 are spaced-apart sufficiently to allow articulation of the shaft 402 and without any stiff points. In some embodiments, adjacent RF shields 900 may be spaced-apart between about 0.1 inches and about 1.0 inches.

By electrically connecting (i.e., shorting) the inner and outer tubular conductors 902, 906 at only one end and not attaching the conductors to ground, each RF shield 900 serves as a quarter-wave resonant choke that forms an effective parallel resonance circuit at a frequency of interest and/or generates high impedance at the inner shield at the location not shorted. Each RF shield 900 impedes the formation of resonating RF waves along conductive members, such as electrical leads and, thus, the transmission of unwanted RF energy along the shaft 402 at such frequency.

Each of the illustrated RF shields 900 can be tuned to a particular frequency by adjusting the length L of the RF shield 900 and/or the thickness of the dielectric layer 304. Typically, the length L of RF shield 900 is about twenty inches (20") or less. However, the RF shield 900 is not limited to a particular length.

Embodiments of the present invention may be utilized in conjunction with navigation and mapping software features. For example, current and/or future versions of system 10 and ablation/mapping catheter 80 described herein may include features with adaptive projection navigation and/or 3-D volumetric mapping technology, the latter may include aspects associated with U.S. patent application Ser. No. 10/076,882, which is incorporated herein by reference in its entirety.

Figure 58:
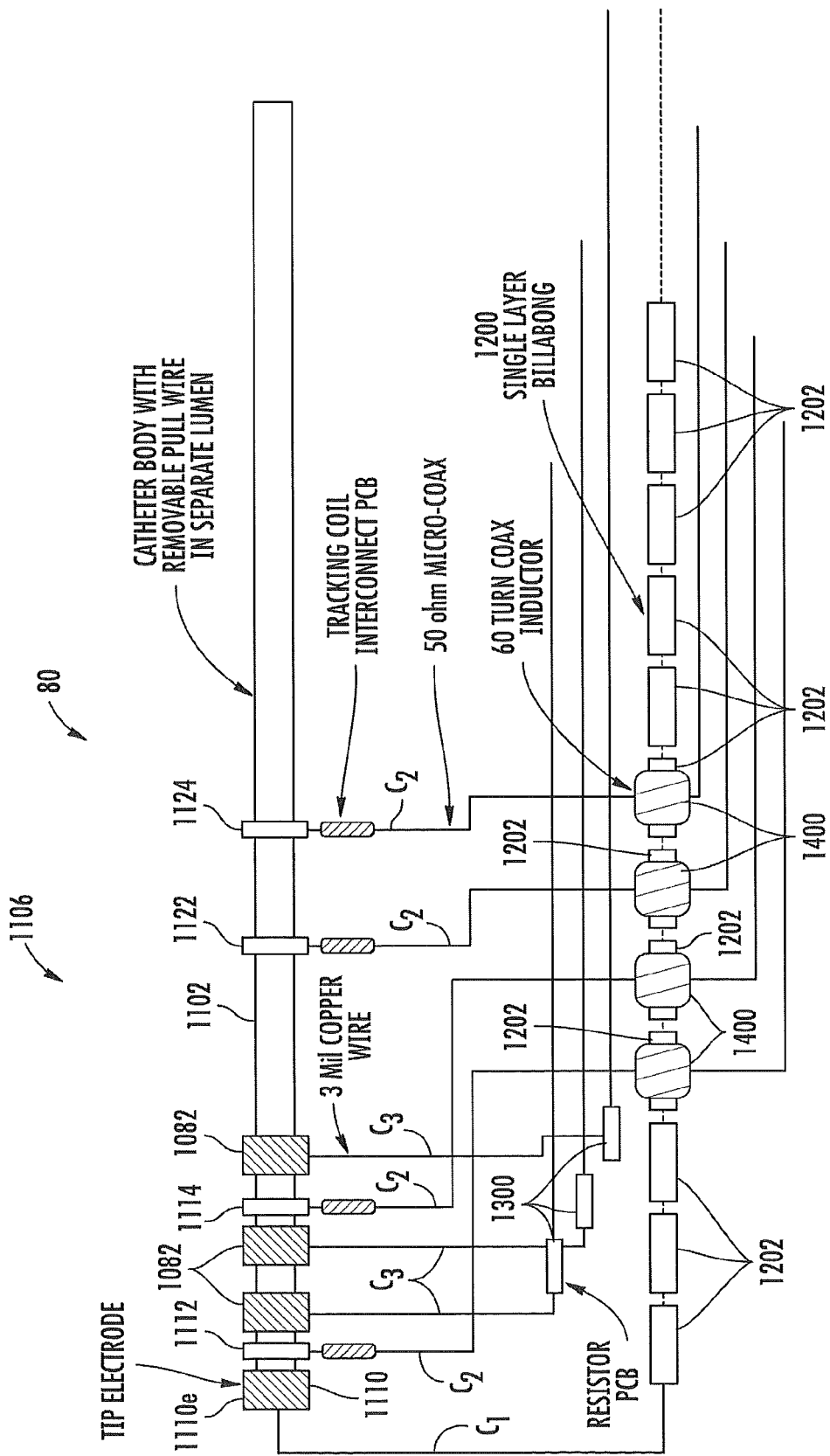
FIG. 58 is a schematic illustration of an exemplary ablation catheter, according to some embodiments of the present invention.

Referring now to FIG. 58, the distal end portion 1106 of an ablation catheter 80, according to some embodiments of the present invention, is illustrated. The ablation catheter 80 includes an elongated flexible housing or shaft 1102 having at least one lumen (not shown) therethrough. The distal end portion 1106 includes an ablation tip 1110 having an ablation electrode 1110e for ablating target tissue. A pair of RF tracking coils individually identified as 1112, 1114, and which can be configured to be functionally equivalent to coils 82c of FIGS. 2-3, are positioned upstream from the ablation tip 1110, as illustrated. The illustrated catheter distal end portion 1106 includes a second pair of RF tracking coils 1122, 1124 in spaced apart relationship, as illustrated. The illustrated catheter distal end portion 1106 includes a pair of EGM (electrogram) sensing electrodes 1082 positioned between the first and second tracking coils 1112, 1114, and a sensing electrode 1082 positioned between the tracking coil 1114 and the tracking coil 1122.

The catheter 80 can include at least the following features for reducing undesired heating caused by RF-induced current: a) a "billabong" cable assembly 1200 for the RF conductor $C_1$ to the ablation electrode 1110e, and optionally for the electrical conductors (e.g., coaxial cables) $C_2$ to the tracking coils 1112, 1114, 1122, 1124, and the electrical conductors $C_3$ to the sensing electrodes 1082; b) high impedance resistors 1300 in communication with the sensing electrodes 1082; and c) self-resonant cable traps 1400 in communication with the tracking coil 1112, 1114, 1122, 1124 connections.

The billabong cable assembly 1200 can include at least the RF conductor $C_1$ and may also include the various cables/conductors (i.e., $C_2$, $C_3$) extending through the lumen of the catheter shaft 1102 and connected to the various components of the ablation catheter 80. In some embodiments, the billabong cable assembly 1200 can include a series of pre-formed back and forth segments 1202 in a serpentine shape (e.g., the various conductors $C_2$, $C_3$ and RF wire $C_1$ turn on themselves in a lengthwise direction a number of times along its length). The term "serpentine" refers to a curvilinear shape of pre-formed back and forth turns of a conductor as a subset of a length of the conductor, such as, for example, in an "s" or "z" like shape, including, but not limited to at least one flattened "s" or "z" like shape, including a connected series of "s" or "z" like shapes or with additional sub-portions of same or other curvilinear shapes to define forward and backward sections of a conductor. The upper and lower (and any intermediate) lengthwise extending segments of a serpentine shape may have substantially the same or different physical lengths.

Figure 64:
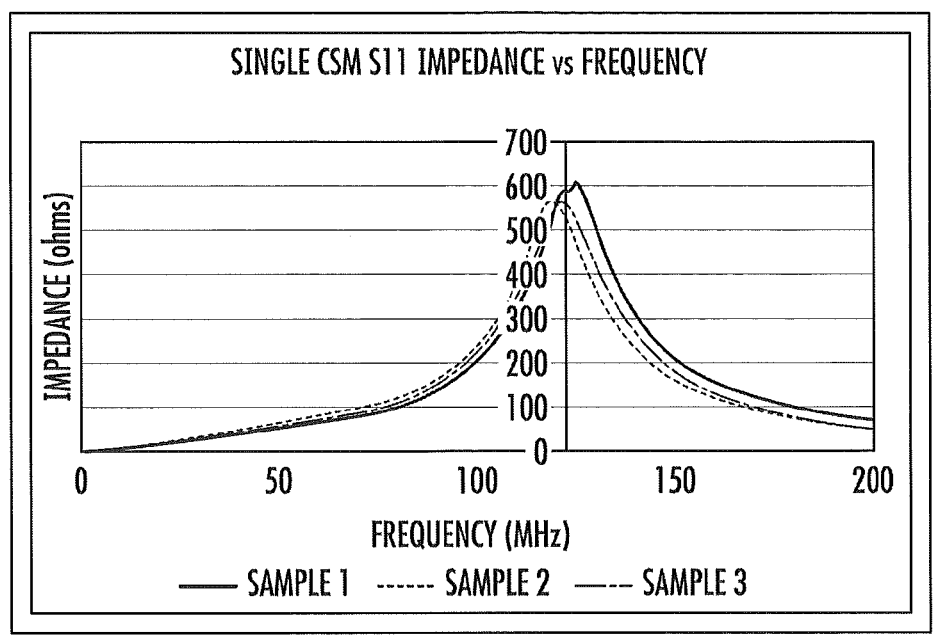
FIGS. 64-65 are graphs illustrating RF safety performance of a billabong assembly, according to some embodiments of the present invention.
Figure 65:
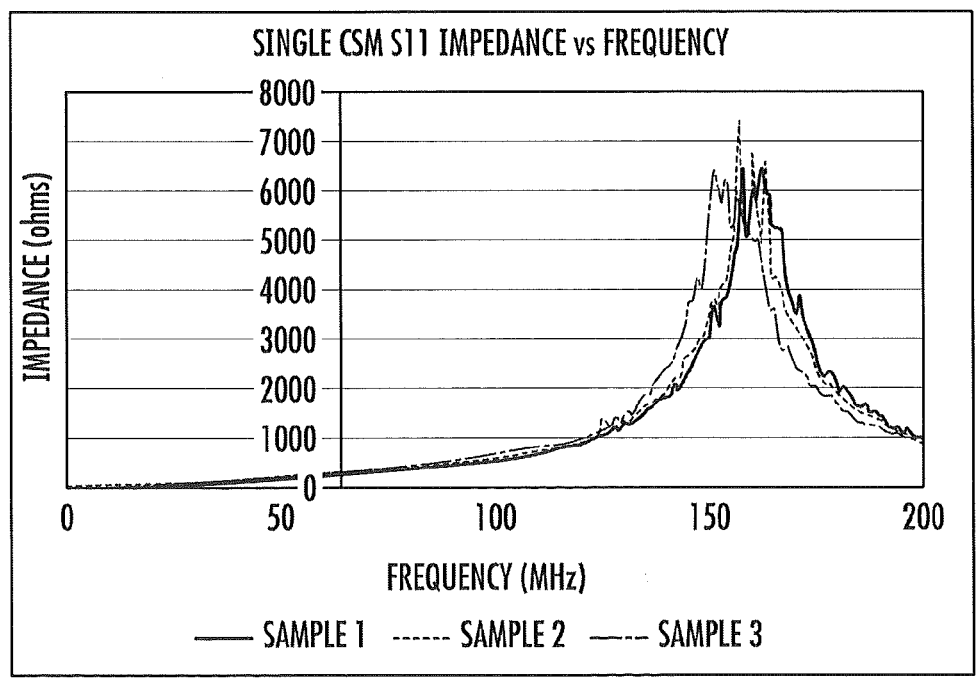
Figure 66:
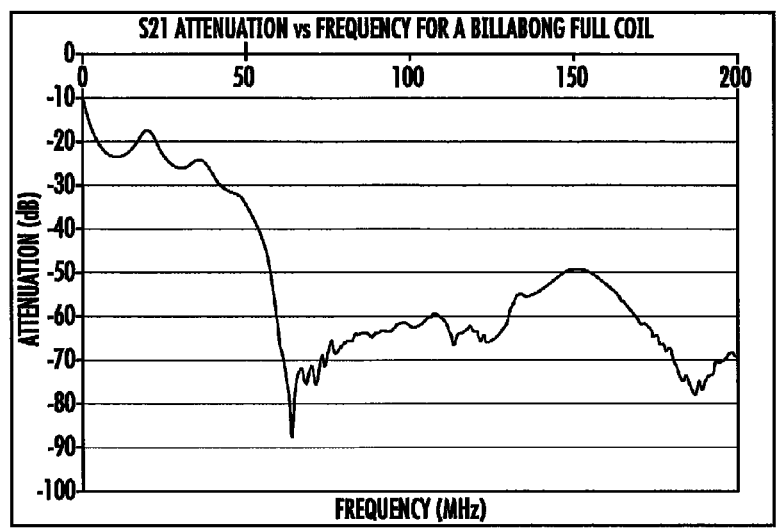
FIG. 66 is a graph illustrating broad spectrum, high attenuation of a billabong assembly, according to some embodiments of the present invention.

Each of the back and forth segments 1202 are referred to as current suppression modules (CSMs). The individual CSMs 1202 have frequency responses dependent on length, pitch, and diameter. Responses from different configurations having good RF safety performance are illustrated in FIGS. 64 and 65. A Billabong coil (composed of many CSMs 1202) can be configured to deliver broad spectrum high attenuation as illustrated in FIG. 66.

Figure 67:
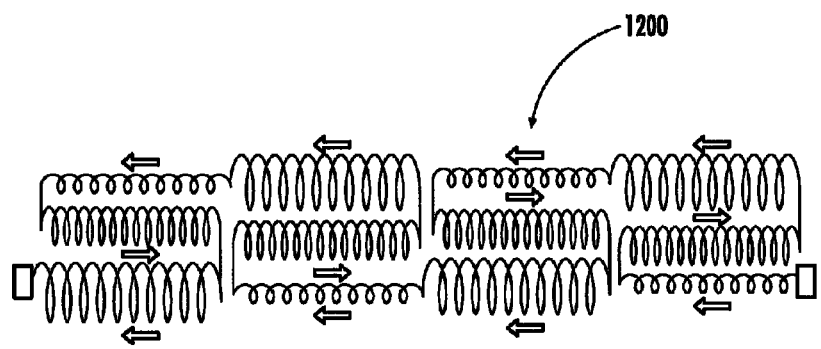
FIG. 67 is a schematic illustration of a single layer billabong assembly, according to some embodiments of the present invention.

FIG. 67 illustrates an alternative billabong cable 1200 configured with CSMs having a series of coiled segments coiled in opposite directions.

The billabong cable assembly 1200 has a unique property of self-cancelling any induced RF current that wants to flow on the cable assembly 1200. At the same time, the billabong cable assembly 1200 provides a low loss path for the 500 KHz ablation current which can reach about 800 mA.

The billabong cable assembly 1200 may perform heat management by a combination of mechanisms. For example, each CSM 1202 can have a high impedance and short length (with respect to the wavelength at MRI frequencies), thus reducing coupling to the local E fields. A CSM's characteristic impedance can also provide tank circuit characteristics, as illustrated in FIGS. 64 and 65. The back and forth winding of each CSM 1202 results in an increased self inductance of the conductor and a build up of parasitic capacitance between the various winds. This self inductance and stray capacitance cause each CSM 1202 to electrically resonate at a particular frequency. Resonating frequency can be chosen to be equal to frequency at which an MRI scanner transmits RF energy. FIG. 64 shows the impedance of a billabong design in which a CSM 1202 resonates at approximately 123 MHz, which is the frequency of operation of a 3 T MRI scanner. Design of a CSM 1202 controls the magnitude of the impedance as well as the resonance frequency. FIG. 65 shows the impedance developed by a CSM 1202 that is in the range of 6,000 ohm.

Multiple CSMs 1202 in series along the length of the device cancel propagating current by phase cancellation between alternate CSMs 1202. Also, multiple CSM billabong conductor/transmission lines have a low pass filter characteristics, such as shown in FIG. 66 (e.g., attenuates RF transmission of frequencies>50 MHz). In addition, the alternating layers of a CSM 1202 coiled in opposite directions provide cancellation of common mode current deposited on the CSM conductors. For the billabong design, the coil diameter, pitch and parasitic capacitance resulting from the wound wires affects electrical properties (impedance and peak frequency) for a given CSM length.

In some embodiments, the billabong cable assembly 1200 is a single layer billabong assembly, as illustrated in FIG. 67. The illustrated billabong assembly is a conductor having a plurality of closely spaced conductor portions in a serpentine shape.

EGM signals are detected by the sensing electrodes 1082 that are in close proximity to cardiac tissue. High impedance (e.g., 5 Kohm or greater) resistors 1300 are used to isolate the sensing electrodes 1082 from the conductor that connects the electrode assembly to ECG amplifiers. Exemplary resistors 1300 are nonmagnetic thick or thin film surface mount types of resistors. ECG amplifiers have very high input impedance (1 MegaOhm), therefore there is negligible signal loss due to 5 Kohm resistors. However, resistors 1300 at the sensing electrodes 1082 provide significant impedance to any RF induced current that might want to flow through the sensing electrodes 1082 to the surrounding tissue.

The tracking coils 1112, 1114, 1122, 1124 detect MRI signals in the RF signals. In order to preserve the integrity of a detected MRI signal, the MRI signal is transmitted down the catheter shaft 1102 using, for example, 50 ohm coaxial cables. In some embodiments, a tracking coil coaxial cable has a 46 AWG, 50 ohm conductive center conductor surrounded by a dielectric layer, and a conductive shield enclosed by an insulating jacket. The coaxial cables $C_2$ isolate the RF signal transmitted via the coaxial cables $C_2$ by concentrating the RF signal between the center conductor and the enclosing shield of a respective coaxial cable $C_2$. The center conductor of a respective coaxial cable $C_2$ is isolated from outside effects, but the shield of the coaxial cable is susceptible to conducting induced RF currents. As such, according to some embodiments of the present invention, self-resonant cable traps 1400 are utilized with the conductors $C_2$.

Figure 59:
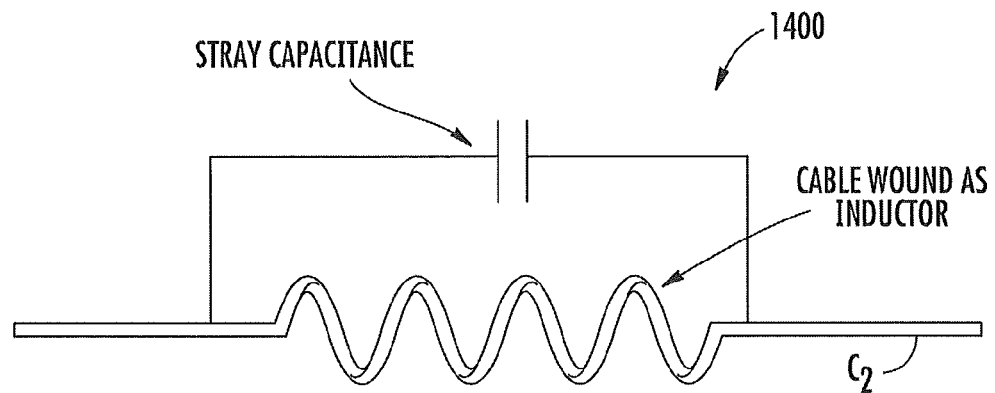
FIG. 59 is a schematic illustration of a self-resonant cable trap that may be utilized by the ablation catheter of FIG. 58, according to some embodiments of the present invention.

Referring to FIG. 59, an example of a self-resonant cable trap 1400 is illustrated in more detail. A high impedance point on a coaxial cable shield is created by winding the coaxial cable $C_2$ as a solenoid such that the inductance of the shield increases to a point where the stray capacitance and the inductance self-resonate at the scanner frequency of operation, which is 128 MHz for a 3 T MRI scanner. In some embodiments, each self-resonant cable trap 1400 is a 60 turn inductor. The 60 turn inductor has the frequency response of a low pass filter. However, other numbers of turns are possible, typically between about 20-100 turns; according to embodiments of the present invention.

Winding the coaxial cable $C_2$ as a solenoid (e.g., 60 turns) develops inductance on the shield of the coaxial cable $C_2$ while the signals traveling inside the coaxial cable $C_2$ do not see any change. This external inductance prevents RF currents from flowing externally on the shield of the coaxial cable $C_2$ through the tracking coils (1112, 1114, 1122, 1124) thereby reducing local heating around the tracking coils (1112, 1114, 1122, 1124).

Figure 60:
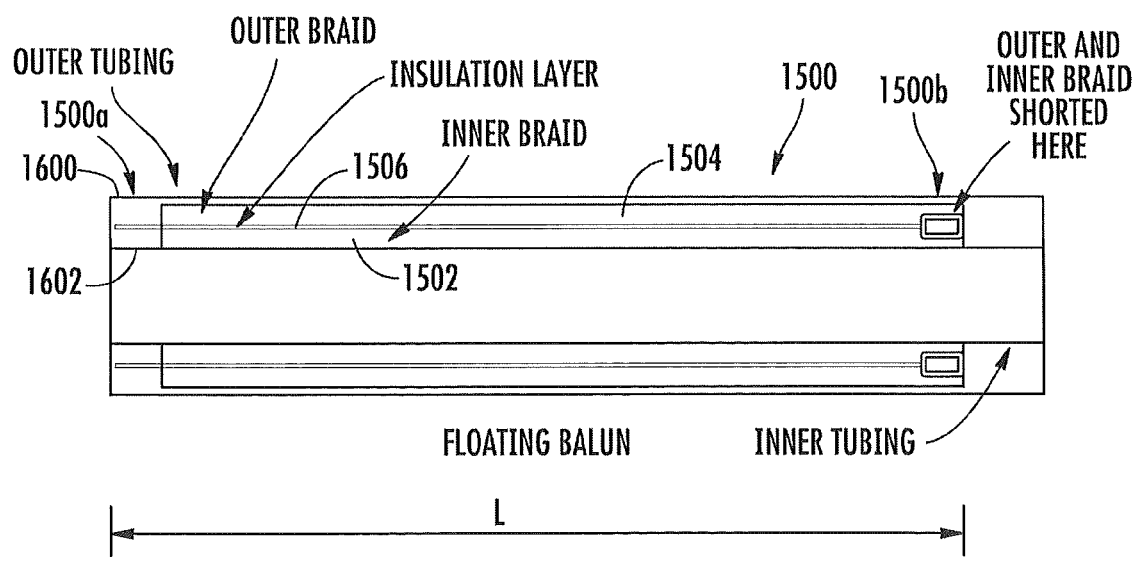
FIG. 60 is a cross-sectional view of a sheath with an integrated RF shield disposed therewithin for use with the ablation catheter of FIG. 58, according to some embodiments of the present invention.
Figure 61:
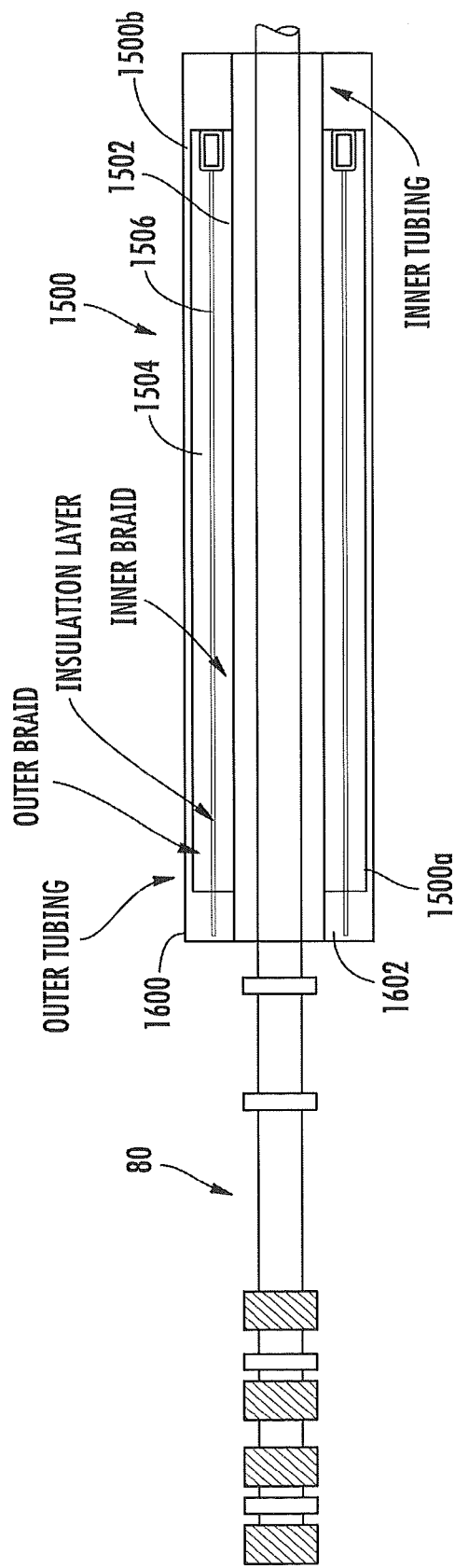
FIG. 61 is a partial side view of the distal end of an ablation catheter with a portion in a sheath, such as that shown in FIG. 60.

In order to further isolate the conductors (e.g., $C_1$, $C_2$, $C_3$) in an ablation catheter 80 from RF currents induced by the MRI coil, a floating balun or RF shield 1500 (FIG. 60) may be embedded within a sheath 1600, such as an introducer sheath. An ablation catheter 80 can be then fed through the lumen 1602 of the sheath 1600, as illustrated in FIG. 61. The illustrated RF shield 1500 includes an inner electrical conductor 1502 (e.g., a conductive braid) and an outer electrical conductor 1504 (e.g., a conductive braid), separated by a dielectric insulator 1506. At one end 1500b of the RF shield 1500, the inner and outer conductors 1502, 1504 are shorted (i.e., electrically connected). At the other end 1500a, the inner and outer conductors 1502, 1504 are not connected (i.e., the inner and outer conductors 1502, 1504 are open circuited).

In some embodiments of the present invention, the length L of the RF shield 1500 is selected to equal one quarter lambda (¼λ) wavelength of the MRI scanner frequency of operation. Taking into account the effect of electrical insulation on top of the outer conductor 1504 and the thickness of the dielectric insulator 1506 between the inner and outer conductors 1502, 1504, the length L is approximately forty eight centimeters (48 cm) for a sheath having an inside diameter of ten French (10 F).

Because the inner and outer conductors 1502, 1504 are shorted at one end 1500b and open circuited at the opposite end 1500a, induced RF currents encounter high impedance at the shorted end and cannot flow on the outer conductor 1504. Moreover, because the outer conductor 1504 is electrically conductive, RF currents are prevented from penetrating through to the inner conductor 1502 and the central lumen of the sheath 1600. As such, the RF shield 1500 isolates the portion of conductors (e.g., $C_1$, $C_2$, $C_3$) within an ablation catheter 80 that are surrounded by the RF shield 1500.

Figure 62A:
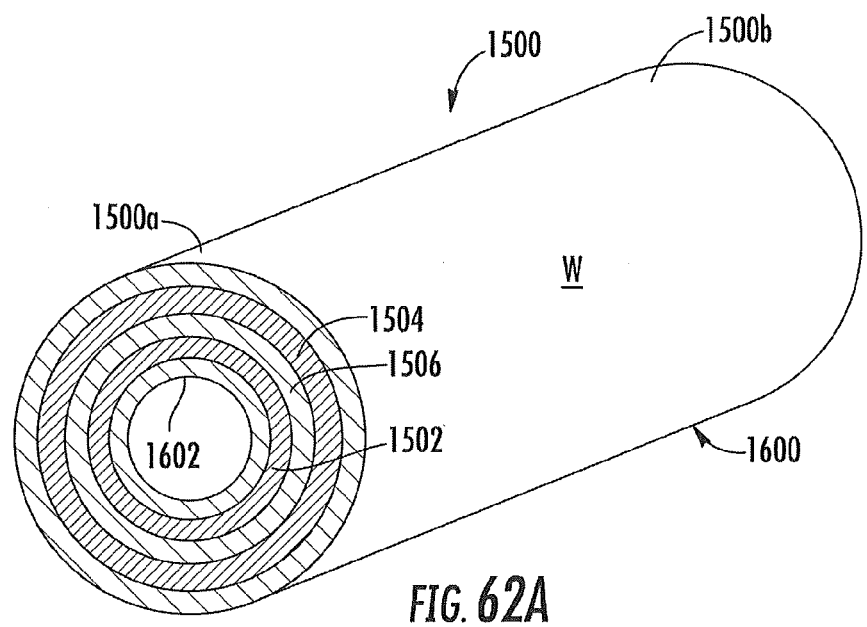
FIG. 62A is a greatly enlarged perspective view of an RF shield disposed within a sheath, according to some embodiments of the present invention.
Figure 62B:
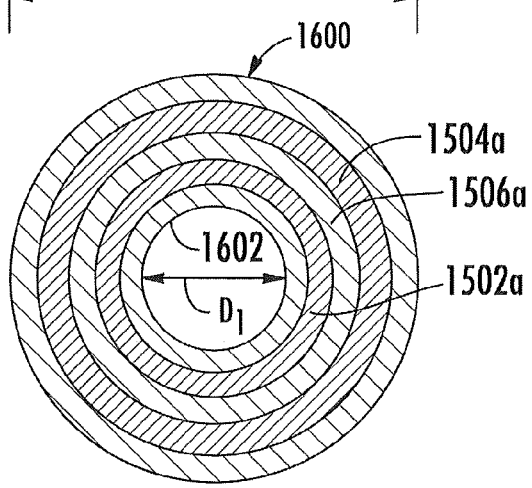
FIGS. 62B and 62C are respective opposite end views of the RF shield of FIG. 62A.
Figure 62C:
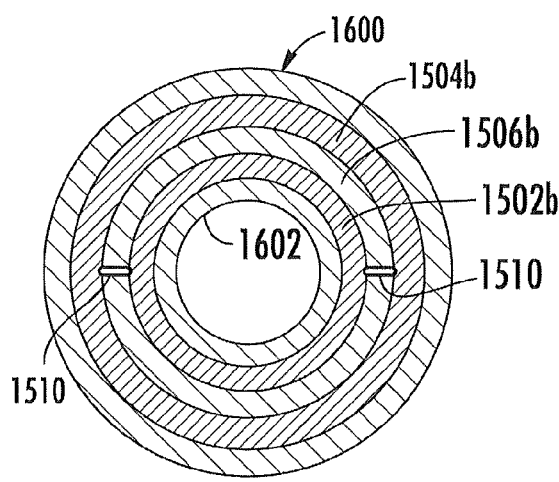

An exemplary RF shield 1500, according to some embodiments of the present invention, is illustrated in more detail in FIGS. 62A-62C. The illustrated RF shield 1500 is embedded within a wall W of a sheath 1600 and has opposite end portions 1500a, 1500b. FIG. 62A is a perspective view of the RF shield 1500, and FIGS. 62B and 62C are respective end views of the RF shield 1500. The illustrated RF shield 1500 includes an elongated inner tubular conductor 1502 having opposite end portions 1502a, 1502b. An elongated dielectric layer 1506 coaxially surrounds the inner tubular conductor 1502, and an elongated outer tubular conductor 1504 coaxially surrounds the dielectric layer 1506 and has opposite end portions 1504a, 1504b. The inner and outer tubular conductors 1502, 1504 are electrically connected to each other (i.e., shorted) at only one of the end portions. The opposite respective end portions are electrically isolated from each other. In the illustrated embodiment, the inner and outer tubular conductors 1502, 1504 are electrically connected to each other at adjacent end portions 1502b, 1504b. End portions 1502a, 1504a are electrically isolated from each other.

In some embodiments, the internal diameter $D_1$ of the sheath 1600 may range from between about 0.170 inch and about 0.131 inch; however, other diameters are possible. An outer diameter $D_2$ of the sheath 1600 may range from between about 0.197 inch and about 0.158 inch, and typically between about 5 French and about 12 French (0.066 inch-0.158 inch); however, other diameters are possible. Exemplary thicknesses of the inner and outer conductors 1502, 1504 may be between about 0.01 inch and about 0.05 inch; however, other thicknesses are possible. Exemplary thicknesses of the dielectric layer 1506 may be between about 0.005 inch and about 0.1 inch; however, other thicknesses are possible.

The thickness of the sheath wall W can be relatively thin, such as between about 0.01 inches and about 0.03 inches; however, other thicknesses are possible. The diameter and length of the sheath 1600 may vary depending upon the patient and/or the procedure for which the catheter 80 is being utilized. Embodiments of the present invention are not limited to any particular sheath size, length, or wall thickness of a medical interventional device. The sheath 1600 can comprise MRI compatible material, such as flexible polymeric material. Various types of polymeric materials may be utilized and embodiments of the present invention are not limited to the use of any particular type of MRI-compatible material. In some embodiments, the sheath proximal end 1500b may be connected to a hemostasis valve (not shown) that is configured to prevent or reduce blood loss and the entry of air, as would be understood by those skilled in the art of the present invention.

The inner and outer tubular conductors 1502, 1504 may be electrically connected in various ways known to those skilled in the art of the present invention. In the illustrated embodiment, the inner and outer tubular conductors 1502, 1504 are electrically connected via a pair of jumper wires (or other conductive elements) 1510 (FIG. 62C). Jumper wires 1510 may be braided wires (e.g., copper wire, copper-plated silver wire, etc.) in some embodiments of the present invention. In other embodiments, the inner and outer tubular conductors 1502, 1504 may be electrically connected by allowing one of the adjacent end portions 1502a, 1504a or 1502b, 1504b to contact each other.

The inner and outer tubular conductors 1502, 1504 may be formed from various types of non-paramagnetic, conductive material including, but not limited to, conductive foils and conductive braids. In some embodiments, the inner and outer conductors 1502, 1504 can be formed as thin-film foil layers of conductive material on opposite sides of a thin film insulator (e.g., a laminated, thin flexible body). An exemplary conductive foil is aluminum foil and an exemplary conductive braid is a copper braid. In some embodiments, the inner and outer tubular conductors 1502, 1504 may be formed from a film having a conductive surface or layer. An exemplary film is Mylar® brand film, available from E.I. DuPont de Nemours and Company Corporation, Wilmington Del.

Figure 63:
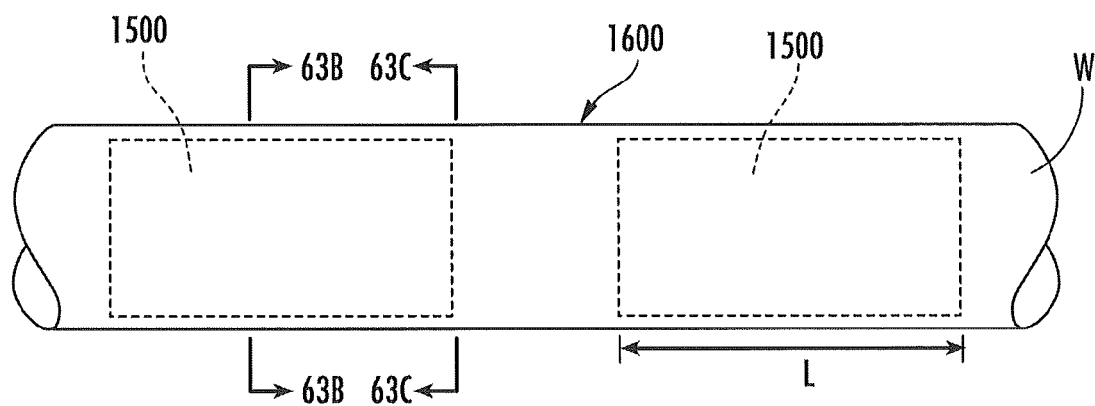
FIG. 63 is a partial side view of a sheath including multiple RF shields in end-to-end spaced-apart relationship, according to some embodiments of the present invention.

Referring now to FIG. 63, the sheath 1600 of FIG. 61 may include a plurality of RF shields 1500 coaxially disposed within the wall W thereof in end-to-end spaced-apart relationship. Although a pair of RF shields 1500 are illustrated in FIG. 63, it is understood that many additional RF shields 1500 may be coaxially disposed within the elongated sheath wall W in end-to-end spaced-apart relationship. Only two RF shields 1500 are shown for ease of illustration. The RF shields 1500 are spaced-apart sufficiently to allow articulation of the sheath 1600 and without any stiff points. In some embodiments, adjacent RF shields 1500 may be spaced-apart between about 0.1 inches and about 1.0 inches. For example, adjacent RF shields 1500 may be spaced apart 0.1 inch, 0.15 inch, 0.20 inch, 0.25 inch, 0.30 inch, 0.35 inch, 0.40 inch, 0.45 inch, 0.50 inch, 0.55 inch, 0.60 inch, 0.65 inch, 0.70 inch, 0.75 inch, 0.80 inch, 0.85 inch, 0.90 inch, 0.95 inch, 1.0 inch, etc. Moreover, all adjacent RF shields 1500 may not be spaced apart by the same amount in some embodiments of the present invention. In addition, embodiments of the present invention are not limited to the range of 0.1 inch to 1.0 inch. Other ranges are possible according to some embodiments of the present invention.

In some embodiments of the present invention, one or more RF shields 1500, as described above, may be coaxially disposed within the elongated flexible shaft 1102 of the catheter 80.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An MRI-compatible catheter, comprising:
   an elongated flexible shaft having a distal end portion, and an opposite proximal end portion;
   an electrical connector interface held by the flexible shaft and configured to be in electrical communication with an MRI scanner;
   an ablation tip at the flexible shaft distal end portion, wherein an RF conductor extends longitudinally within the flexible shaft to the electrical connector interface and connects the ablation tip to an RF generator, wherein the RF conductor includes a series of back and forth segments along its length;
   at least one RF tracking coil positioned adjacent the distal end portion of the flexible shaft, wherein the at least one tracking coil includes a conductive lead extending between the at least one RF tracking coil and the electrical connector interface and configured to electrically connect the at least one tracking coil to the MRI scanner;
   at least one self-resonant cable trap in communication with the at least one RF tracking coil;

at least one sensing electrode at the shaft distal end portion; and at least one high impedance resistor in communication with the at least one sensing electrode.

2. The catheter of claim 1, wherein the conductive lead includes a series of pre-formed back and forth segments along its length.

3. The catheter of claim 1, wherein the conductive lead is a coaxial cable.

4. The catheter of claim 1, wherein the at least one RF tracking coil comprises a plurality of tracking coils, each attached to a separate conductive lead, and wherein each conductive lead includes a series of back and forth segments along its length.

5. The catheter of claim 1, wherein the at least one self-resonant cable trap comprises an inductor having between about twenty (20) turns and about one-hundred (100) turns.

6. The catheter of claim 1, wherein the conductive lead has a length sufficient to define an odd harmonic/multiple of a quarter wavelength of an operational frequency of the MRI Scanner.

7. The catheter of claim 1, wherein the ablation tip comprises platinum.

8. The catheter of claim 1, wherein the at least one RF tracking coil comprises between 1-10 coil turns.

9. The catheter of claim 1, wherein the at least one RF tracking coil has a length along a longitudinal direction of the catheter of between about 0.25 mm and about 4 mm.

10. The catheter of claim 1, further comprising at least one fluid exit port at the flexible shaft distal end portion, wherein the at least one fluid exit port is in fluid communication with an irrigation lumen that extends longitudinally through the flexible shaft from the at least one fluid exit port.

11. The catheter of claim 1, wherein the at least one RF tracking coil comprises a plurality of tracking coils, each attached to a separate conductive lead, and wherein each conductive lead has a length sufficient to define an odd harmonic/multiple of a quarter wavelength of an operational frequency of the MRI Scanner.

12. The catheter of claim 1, wherein the at least one RF tracking coil is in communication with a circuit configured to stabilize a tracking signal generated by the at least one RF tracking coil.

13. The catheter of claim 12, further comprising a handle attached to the flexible shaft proximal end portion, and wherein the circuit is located within the handle.

14. The catheter of claim 1, further comprising a sheath surrounding at least a portion of the elongated flexible shaft, wherein the sheath includes at least one RF shield coaxially disposed therewithin, the at least one RF shield comprising:

elongated inner and outer conductors, each having respective opposite first and second end portions; and an elongated dielectric layer of MRI compatible material sandwiched between the inner and outer conductors and surrounding the inner conductor, wherein only the respective first end portions of the inner and outer conductors are electrically connected, and wherein the second end portions are electrically isolated.

15. The catheter of claim 14, wherein the inner and outer conductors comprise conductive foil, conductive braid, or a film with a conductive surface.

16. The catheter of claim 14, wherein the at least one RF shield comprises a plurality of RF shields in end-to-end spaced-apart relationship.

17. The catheter of claim 1, further comprising at least one RF shield coaxially disposed within the flexible shaft, the at least one RF shield comprising:

elongated inner and outer conductors, each having respective opposite first and second end portions; and an elongated dielectric layer of MRI compatible material sandwiched between the inner and outer conductors and surrounding the inner conductor, wherein only the respective first end portions of the inner and outer conductors are electrically connected, and wherein the second end portions are electrically isolated.

18. The catheter of claim 17, wherein the inner and outer conductors comprise conductive foil, conductive braid, or a film with a conductive surface.

19. The catheter of claim 17, wherein the at least one RF shield comprises a plurality of RF shields in end-to-end spaced-apart relationship.

\* \* \* \* \*

UNITED STATES PATENT AND TRADEMARK OFFICE
CERTIFICATE OF CORRECTION

PATENT NO.        : 8,825,133 B2                                        Page 1 of 1
APPLICATION NO.   : 13/749351
DATED             : September 2, 2014
INVENTOR(S)       : Jenkins et al.

It is certified that error appears in the above-identified patent and that said Letters Patent is hereby corrected as shown below:

On Title Page 2, Item (56), References Cited, U.S. PATENT DOCUMENTS: Please add the following U.S. reference:

5,908,445    6/1999    Whayne et al.

Signed and Sealed this
Twenty-fourth Day of February, 2015

Michelle K. Lee
*Deputy Director of the United States Patent and Trademark Office*